(12) United States Patent
Matsunami et al.

(10) Patent No.: US 7,879,565 B2
(45) Date of Patent: *Feb. 1, 2011

(54) MODULATORS THAT PROMOTE CELL SURFACE EXPRESSION OF ODORANT RECEPTORS

(75) Inventors: Hiroaki Matsunami, Durham, NC (US); Momoka Matsunami, Durham, NC (US); Harumi Saito, Durham, NC (US); Hanyi Zhuang, Durham, NC (US)

(73) Assignee: Duke University, Durham, NC (US)

( * ) Notice: Subject to any disclaimer, the term of this patent is extended or adjusted under 35 U.S.C. 154(b) by 79 days.

This patent is subject to a terminal disclaimer.

(21) Appl. No.: 12/207,102

(22) Filed: Sep. 9, 2008

(65) Prior Publication Data

US 2009/0092997 A1 Apr. 9, 2009

Related U.S. Application Data

(63) Continuation of application No. 11/156,516, filed on Jun. 20, 2005, now Pat. No. 7,425,445.

(60) Provisional application No. 60/581,087, filed on Jun. 18, 2004, provisional application No. 60/582,011, filed on Jun. 22, 2004.

(51) Int. Cl.
*G01N 33/566* (2006.01)
*C07K 14/705* (2006.01)

(52) U.S. Cl. .......................... 435/7.2; 435/7.21; 436/501

(58) Field of Classification Search ....................... None
See application file for complete search history.

(56) References Cited

U.S. PATENT DOCUMENTS

| 5,993,778 | A | 11/1999 | Firestein |
| 2002/0048812 | A1 | 4/2002 | Ronnett |
| 2005/0233418 | A1 | 10/2005 | Baum |

FOREIGN PATENT DOCUMENTS

| WO | 01/75067 | 10/2001 |
| WO | 03/025130 | 3/2003 |
| WO | WO 03/098221 | 11/2003 |

OTHER PUBLICATIONS

Adler et al. (2000), "A Novel Family of Mammalian Taste Receptors," Cell 100,693-702.
Angers, S., et al. (2002), "Dimerization: An Emerging Concept for G Protein-Coupled Receptor Ontogeny and Function," Annu Rev Pharmacol Toxicol 42,409-435.
Axel R., (1995), "The Molecular Logic of Smell . . . ", Sci Am 1273, 154-159.
Baker, E.K., et al. (1994), "The Cyclophilini homolog NinaA functions as a chaperone, forming a stable complex in vivo with its protein target rhodopsin," Embo J 13,4886-4895.
Belluscio, L., et al. (1998), "Mice Deficient in Golf Are Anosmic," Neuron 20,69-81.
Bozza T., et al., "Odorant Receptor Expression Defines Functional Units in the Mouse Olfactory System," (2002) J Neurosci 22,3033-3043.
Brady, A.E and Limbird, L.E. (2002), "G protein-coupled receptor interacting proteins: Emerging roles in localization and signal transduction," Cell Signal 14,297-309.
Brady, G., and Iscove, N.N. (1993), "Construction of cDNA Libraries from Single Cells," Methods Enzymol 225,611-623.
Brands, A., and Ho, T.H. (2002), "Function of a Plant Stress-Induced Gene, HVA22. Synthetic Enhancement Screen with Its Yeast Homolog Reveals Its Role in Vesicular Traffic," Plant Physiol 130,1121-1131.
Buck L., and Axel R. (1991), "A Novel Multigene Family May Encode Odorant Receptors: A Molecular Basis for Odor Recognition," Cell 65, 175-187.
Calero, M, (2001), "Yop1p, the Yeaste Homolog of the Polyposis Locus Protein 1, Interacts with Yip1p and Negatively Regulates Cell Growth," J Biol Chem 276,12100-12112.
Chandrashekar, J., et al (2000), "T2Rs Function as Bitter Taste Receptors," Cell 100,703-711.
Chen, C.N., et al. (2002), "AtHVA22 gene family in Arabibopsis: phylogenetic relationship, ABA and stress regulation, and tissue-specific expression," Plant Mol Biol 49,633-644.
Database UniProt (online) Jun. 1, 2003, "Receptor-transporting protein 2." XP002471384 retrieved from EBI accession No. UniProt: Q80Z1s.
Database UniProt (online) Mar. 1, 2001, "Receptor expression-enhancing protein 1." XP002471382 retrieved from EBI accession No. UniProt:Q9H902.
Database UniProt (online) Mar. 1, 2003, "Receptor expression-enhancing protein 1," XP002471381, retrieved from EBI accession No. UniPot:Q8BGH4.
Database UniProt (online) Mar. 1, 2003, "Receptor-transporting protein 1." XP002471383 retrieved from EBI accession No. UniProt: Q8C8C1, Database accession No. Q8C8C1.
Dulac, C., and Axel R. (1995), "A Novel Family of Genes Encoding Putative Pheromone Receptors in Mammals," Cell 83, 195-206.
Dwyer, N.D., et al. (1998), "Odorant Receptor Localization to Olfactory Cilia is Mediated by ODR-4, a Novel Membrane-Associated Protein," Cell 93,445-466.
Dwyer, N.D., et al., (2001), "Polarized Dendritic Transport and the AP-1 µ9 Clathrin Adaptor UNC-101 Localize Odorant Receptors to Olfactory Cilia," Neuron 31, 277-287.

(Continued)

Primary Examiner—John D Ulm
(74) Attorney, Agent, or Firm—Casimir Jones SC

(57) ABSTRACT

The present invention relates to polypeptides capable of promoting odorant receptor cell surface localization and odorant receptor functional expression. The present invention further provides assays for the detection of ligands specific for various odorant receptors. Additionally, the present invention provides methods of screening for odorant receptor accessory protein polymorphisms and mutations associated with disease states, as well as methods of screening for therapeutic agents, ligands, and modulators of such proteins.

7 Claims, 70 Drawing Sheets

OTHER PUBLICATIONS

Evans et al., "An engineered poliovirus chimaera elecits broadly reactive HIV-1 neturalizing antibodies," Nature 339:385 (1989).
Ferreira, P.A., et al., (1996), "Cyclophilin-related protein RanBP2 acts as chaperone for red/green opsin," Nature 383,637-640.
Firestein, S. (2001), "How the olfactory system makes sense of scents," Nature 413, 211-218.
Gaillard, I., et al., (2002), "A single olfactory receptor specifically binds a set of odorant molecules," Eur Neurosci 15,409-418.
Gimelbrant, A. A., et al., (2001), "Olfactory Receptor Trafficking Involves Conserved Regulatory Steps," J Biol Chem 276,7285-7290.
Glusman, G., et al. (2001), "The Complete Human Olfactory Subgnome," Genome Res 11,685-702.
Griff, I.C. , and Reed, R.R. (1995), "The Genetic Basis for Specific Anosmia to Isovaleric Acid in the Mouse," Cell 83, 407-414.
Hatt, H. et al., "Cloning, Functional Expression and Characterization of a Human Olfactory Receptor," (1999) Cell Mol Biol 45,285-291.
Huang et al., "Vaccinia Virus Recombinants Expressing an 11-Kilodalton β-Galactosidase Fusion Protein Incorporate Active β-Galactosidase in Virus Particles," J. Virol., 62:3855 (1988).
Hurt, C.M. et al. (2000), "Cell-type Specific Targeting of the α2c-Adrenoceptor," J Biol Chem 275,35424-35431.
International Search Report dated Apr. 10, 2007 for PCT/US2005/021921 (WO2006/002161).
Jones, D.T., and Reed, R.R. (1989), "Golf: An Olfactory Neuron Specific-G Protein Involved in Odorant Signal Transduction," Science 244,790-795.
Jones, K.A., et al. (1998), "GABAβ receptors function as a heteromeric assembly of the subunits GABAβR1 and GABAβR2," Nature 396,674-679.
Kajiya, K. et al., (2001), "Molecular Bases of Odor Discrimination: Reconstitution of Olfactory Receptors that Recognize Overlapping Sets of Odorants," J Neurosci 21,6018-6025.
Katada et al., "Odorant Response Assays for a Heterologously Expressed Olfactory Receptor," Biochemical and Biophysical Research Communications, Jun. 13, 2003, vol. 305, No. 4, pp. 964-969.
Kaupmann, K., et al. (1998), "GABAβ-receptor subtypes assemble into functional heteromeric complexes," Nature 396, 683-687.
Kinzler, K.W., et al. (1991), "Identification of FAP Locus Genese from Chromosome 5q21," Science 253,661-665.
Krautwurst D., et al., (1998), "Identification of Ligands for Olfactory Receptors by Functional Expression of a Receptor Library," Cell 95, 917-926.
Laird, D.W., and Molday, R.S. (1988), "Evidence Against the Role of Phodopsin in Rod Outer Segment Binding to RPE Cells," Invest Ophthalmol Vis Sci 29,419-428.
Lewcock, J.W., and Reed, R. R. (2004), "A Feedback Mechanism Regulates Monoallelic Odorant Receptor Expression," Proc Natl Acad Sci USA.
Loconto, J., et al., (2003), "Functional Expression of Murine V2R Pheromone Receptors Involves Selective Association . . . ", Cell 112,607-618.
Lu, M., et al., (2003), "Endoplasmic Reticulum Retention, Degradation, and . . . ", Traffic 4,416-433.
Malnic, B. et al., (1999), "Combinatorial Receptor Codes for Odors," Cell 96, 713-723.
Matsunami, H., and Buck, L.B. (1997), "A Multigene Family Encoding a Diverse Array of Putative Pheromone Receptors in Mammals," Cell 90,755-784.
Matsunami, H., et al. (2000), "A family of candidate taste receptors in human and mouse," Nature 404,601-604.
McClintock, T.S. (1997), "Functional expression of olfactory-adrenergic receptor . . . ", Brain Res Mol Brain Res 48,270-278.
McClintock, T.S., and Sammeta, N. (2003), "Trafficking prerogatives of olfactory receptors," Neuroreport 14,1547-1552.
McLatchie, L.M. et al., (1998), "RAMPs regulate the transport and ligand specificity of the calcitonin-receptor-like receptor," Nature 393,333-339.
Mombaerts, P. (1999), "Molecular Biology of Odorant Receptors in Vertebrates," Annu Rev Neurosci 22, 487-509.
Mombaerts, P., (1996), "Visualizing an Olfactory Sensory Map," Cell 87, 675-686.
Nardelli et al., "A Chemically Defined Synthetic Vaccine Model for HIV-1," J. Immunol., 148:914 (1992).
Parmentier, M., et al. (1992), "Expression of members of the putative olfactory receptor gene family in mammalian germ cells," Nature 355,453-455.
Posnett et al., "A Novel Method for Producing Anti-peptide Antibodies," J. Biol. Chem., 263:1719 (1988).
Prieschl, E., et al. (1996), "The murine homolog of TB2/DP1, a gene of the familial adenomatous polyposis (FAP) locus," Gene 169,215-218.
Raming, K., et al., (1993), "Cloning and expression of odorant receptors," Nature 361,353-356.
Saha, S., et al., (2002), "Using the transcriptome to annotate the genome," Nat Biotechnol 20,508-512.
Saito Harumi et al., "RTP family members induce functional expression of mammalian odorant receptors," Cell, Cell Press, Cambridge, NA, US, vol. 119, No. 5, Nov. 24, 2004, pp. 679-691.
Schaeren-Wiemers, N., and Gerfin-Moser, A. (1993), "A Single protocol to detect transcripts of various types and . . . ", Histochemistry 100,431-440.
Schlienger et al., "Human Immunodeficiency Virus Type 1 . . . ", J. Virol., 66:2 (1992).
Serizawa, S. et al., (2003), "Negative Feedback Regulation Ensures the One Receptor-One Olfactory Neuron Rule in Mouse," Science 302, 2088-2094.
Shen, Q., et al. (1993), "Hormone Response Complex in a Novel Abscisic Acid and Cycloheximide-inducible Barley Gene," J Biol Chem 268,23652-23660.
Shieh, B.H., et al., (1989), "The ninaA gene required for visual transduction in *Drosophila* encodes a homologue of cyclosporin A—binding protein," Nature 338,67-70.
Spehr, M., et al (2003), "Identification of a Testicular Odorant Receptor Mediating Human Sperm Chemotaxis," Science 299,2054-2058.
Supplementary European Search Report, EP Application No. EP05792749 dated Mar. 4, 2008.
Touhara, K., et al. (1999), "Functional identification and reconstitution of oan odorant receptor in single olfactory neurons," Proc Natl Acad Sci USA 96,4040-4045.
Wang F., et al., (1998), "Odorant Receptors Govern the Formation of a Precise Topographic Map," Cell 93, 47-60.
Watanabe, S., et al. (1995), "Stable Production of Mutant Mice from Double Gene Converted ES Cells with Puromycin and Neomycin," Biochem Biophys Res Commun 213,130-137.
White, J.H., et al. (1998), "Heterodimerization is required for the formation of a functional GABAβ receptor," Nature 396,679-682.
Young, J.M., et al. (2002), "Different evolutionary processes shaped the mouse and human olfactory receptor gene families," Hum Mol Genet 11,535-546.
Yu, R., and Hinkle, P.M. (1997), "Effect of Cell Type on the Subcellular Localization of the Thyrotropin-Releasing Hormone Receptor," Mol Pharmacol 51,785-793.
Zawistowski, J.S., et al. (2002), "KRIT1 association with the integrin-binding . . . ", Hum Mol Genet 11,389-396.
Zhang, X., and Firestein, S. (2002), "The olfactory receptor gene superfamily of the mouse," Nat Neurosci 5,124-133.
Zhao, et al., (1998), "Functional Expression of a Mammalian Odorant Receptor," Science 279,237-242.
Zozulya, S., et al. (2001), "The human olfactory receptor repertoire," Genome Biol 2,18.
CA Patent Application No. 2,571,080, Office Action dated Oct. 1, 2009.

Number of Labelled cells (%)

| | Untransfected | Adr-R only | Receptor | +RTP1 | +RTP2 | +REEP1 | +RTP1,REEP1 | +RTP1,2 | +RTP2,REEP1 | +RTP1,2,REEP1 |
|---|---|---|---|---|---|---|---|---|---|---|
| MOR203-1+, Adr-R+ | 0.06 | 0.14 | 0.5 | 4.8 | 0.75 | 0.86 | | | | 5.9 |
| Adr-R+ | 1.05 | 23.62 | 17.83 | 18.41 | 17.38 | 18.55 | | | | 18.21 |
| Ratio | | 0.006 | 0.028 | 0.261 | 0.043 | 0.051 | | | | 0.324 |
| OREG+, Adr-R+ | 0.08 | 0.36 | 1.46 | 11.09 | 6.08 | 1.85 | | | | 7.45 |
| Adr-R | 2.37 | 50.55 | 57.48 | 62.89 | 51.27 | 63.72 | | | | 47.74 |
| Ratio | | 0.007 | 0.025 | 0.176 | 0.119 | 0.029 | | | | 0.156 |
| OR-S46+, Adr-R+ | 0.31 | 0.75 | 6.17 | 12.28 | 8.05 | 5.17 | | | | 9.23 |
| Adr-R | 3.85 | 13.91 | 17.32 | 19.41 | 21.67 | 18.57 | | | | 18.56 |
| Ratio | | 0.054 | 0.356 | 0.633 | 0.371 | 0.278 | | | | 0.497 |
| Olfr62+, Adr-R+ | 0.11 | 0.3 | 3.43 | 15.23 | 11.23 | 2.96 | 11.62 | 11.94 | 8.02 | 12.64 |
| Adr-R | 1.77 | 31.53 | 22.2 | 27.68 | 27.22 | 20.19 | 20.84 | 20.87 | 20.32 | 19.11 |
| Ratio | 0.06 | 0.009 | 0.13 | 0.557 | 0.425 | 0.133 | 0.559 | 0.583 | 0.39 | 0.657 |
| VR4(V2R)+, Adr-R+ | 0.05 | 0.08 | 0.64 | 0.49 | 1.22 | 1.89 | | | | 1.68 |
| Adr-R | 3.09 | 41.5 | 44.17 | 44.66 | 40.61 | 42.71 | | | | 38.54 |
| Ratio | | 0.002 | 0.014 | 0.011 | 0.03 | 0.044 | | | | 0.043 |
| mT2R5+, Adr-R+ | 0.18 | 0.45 | 21.59 | 20.89 | 18.24 | 20.74 | | | | 16.83 |
| Adr-R | 2.41 | 27.79 | 26.32 | 24.37 | 23.18 | 25.09 | | | | 22.15 |
| Ratio | | 0.021 | 0.822 | 0.85 | 0.784 | 0.813 | | | | 0.754 |

Mean of Labelled cells (A.U.)

| | Untransfected | Adr-R only | Receptor | +RTP1 | +RTP2 | +REEP1 | +RTP1,REEP1 | +RTP1,2 | +RTP2,REEP1 | +RTP1,2,REEP1 |
|---|---|---|---|---|---|---|---|---|---|---|
| MOR203-1+, Adr-R+ | 15.58 | 17.25 | 19.29 | 24.41 | 19.25 | 24.78 | | | | 24.43 |
| Adr-R | 42.76 | 57.73 | 45.09 | 41.66 | 42.5 | 39.69 | | | | 44.63 |
| OREG+, Adr-R+ | 24.2 | 22.84 | 27.07 | 48.59 | 45.15 | 26.66 | | | | 50.4 |
| Adr-R | 23 | 79.49 | 77.78 | 83.59 | 58.58 | 81.47 | | | | 62.41 |
| OR-S46+, Adr-R+ | 13.85 | 13.97 | 19.02 | 31.02 | 19.84 | 18.24 | | | | 23.19 |
| Adr-R | 26.96 | 49.14 | 38.84 | 43.82 | 37.78 | 44.51 | | | | 39.58 |
| Olfr62+, Adr-R+ | 18.94 | 20.65 | 22.67 | 42.11 | 35.59 | 25.82 | 38.38 | 45.95 | 32.67 | 46.61 |
| Adr-R | 38.08 | 69.4 | 53.57 | 62.25 | 54.79 | 52.1 | 53.4 | 53.31 | 49.33 | 52.36 |
| VR4(V2R)+, Adr-R+ | 23.22 | 29.22 | 31.14 | 31.81 | 32.66 | 28.86 | | | | 26.31 |
| Adr-R | 23.59 | 85.74 | 59.78 | 63.33 | 51.56 | 59.7 | | | | 47.11 |
| m T2R5+, Adr-R+ | 20.26 | 20.08 | 65.81 | 71.79 | 61.14 | 64.25 | | | | 58.48 |
| Adr-R | 26.14 | 61.82 | 44.88 | 48.81 | 44.76 | 44.05 | | | | 44.95 |

FIGURE 5

A REEP1  SEQ ID NO: 21

<u>MVSWIISRLVVLIFGTLYPAYYSYKAVKSKDIKEYVK</u><u>WMM</u>  40
     TM/SS

<u>YWIIFALFTTAETFTDIFLCWFPFYYELKIAFVAWLLSPY</u>  80
          TM

TKGSSLLYRKFVHPTLSSKEKEIDDCLVQAKDRSYDALVH  120

FGKRGLNVAATAAVMAASKGQGALSERLRSFSMQDLTTIR  160

GDGAPAPSGPPPPGTGRSSGKHSQPKMSRSASESAGSSGT  200

A---------------------------------------  201

B

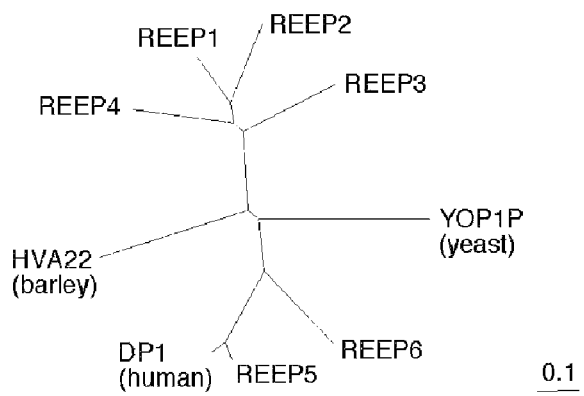

C  (RTP1 - SEQ ID NO: 33)  (RTP2 - SEQ ID NO: 34)

```
RTP1  MRIFRPWRLRCPALHLPSFPTFSIKCSLPPLPTDEDNCKS  40
RTP2  ------------------------------------MSTS  4

RTP1  VTTGEWKKVFYEKMEEVKPADSWDFIIDPNLKHNVLAPGW  80
RTP2  LTTCEWKKVFYEKMEVAKPADSWELIIDPTLKPNELGPGW  44

RTP1  KQYLELEASGRFHCSWCWHTWQSPHVVILFHMYLDKAQRA  120
RTP2  KQYLEQEASGRFHCSWCWHTWQSANVVILFHMHLDRAQRV  84

RTP1  GSVRMRVFKQLCYECGTARLDESSMLEENIESLVDNLITS  160
RTP2  GSVRMRVFKQLCYQCGTSRLDESSMLEENIEGLVDNLITS  124

RTP1  LREQCYGERGGHYRIHVASRQDNRRHRGEFCEACQEGIVH  200
RTP2  LREQCYDEDGGQYRIHVASRPDSGLHRSEFCEACQEGIVH  164

RTP1  WKPSEKLLEEEATTYTFSRAPSPTKPQAETGSGCNFCSIP  240
RTP2  WKPSEKLLEEDAAYTDAS------KKKGQAGFISSEFSFR  198

RTP1  WCLFWATVLMLIIYLQFSFRTSV----------------  263
RTP2  WCLFWGILCLVIVYLQFFRGRSGFL--------------  223
       TM
```

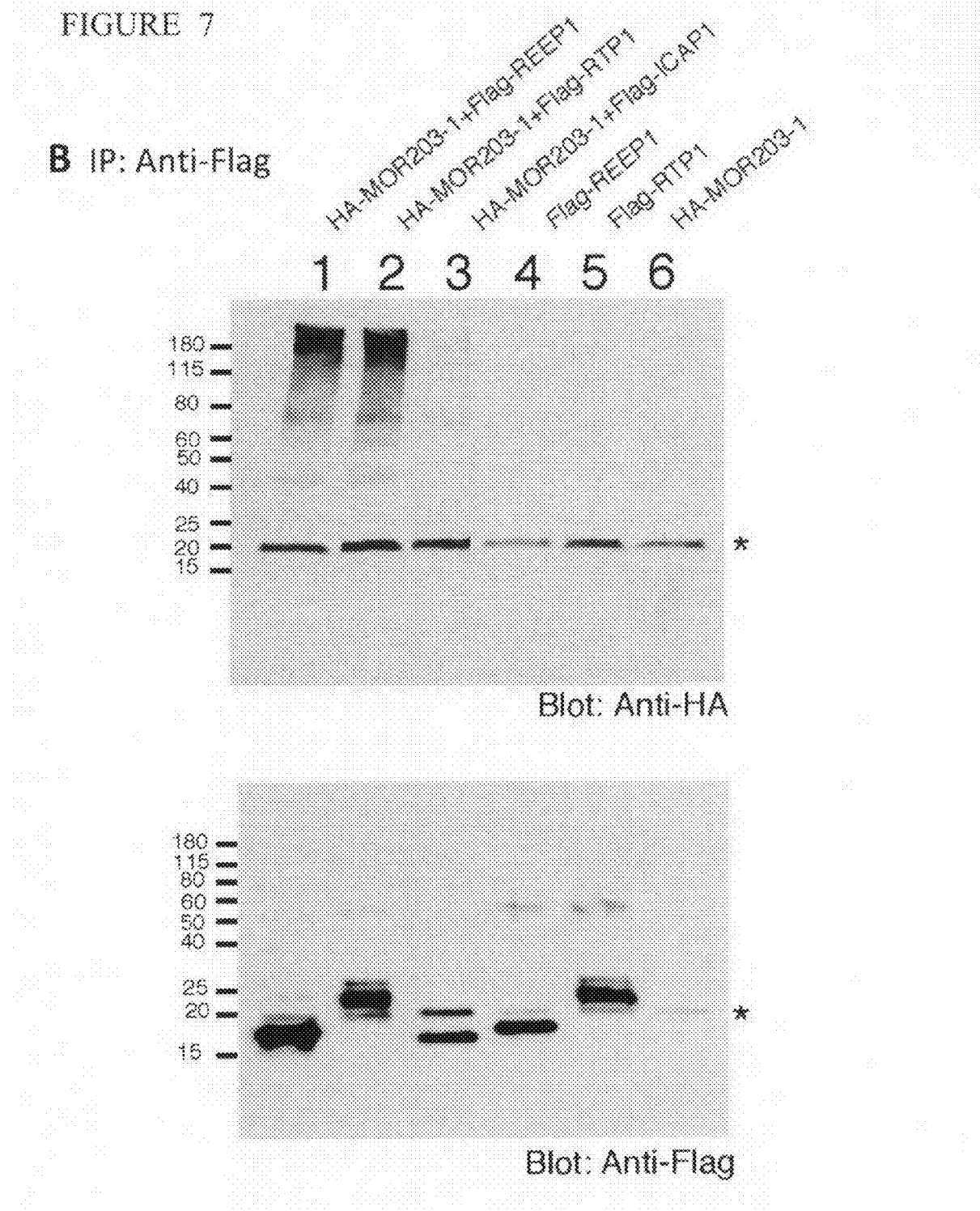

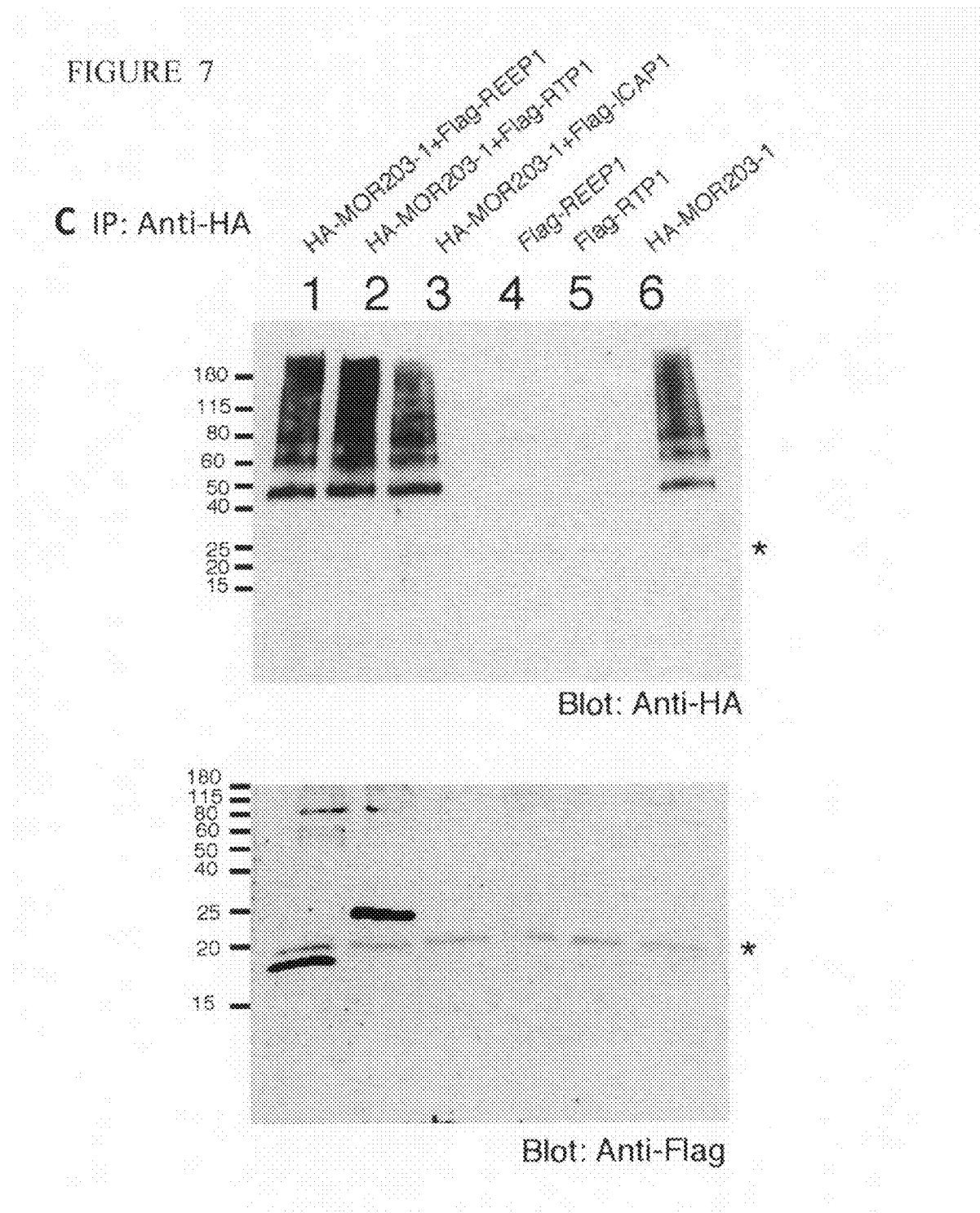

FIGURE 8
A 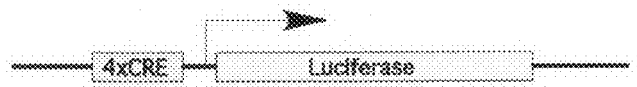
B 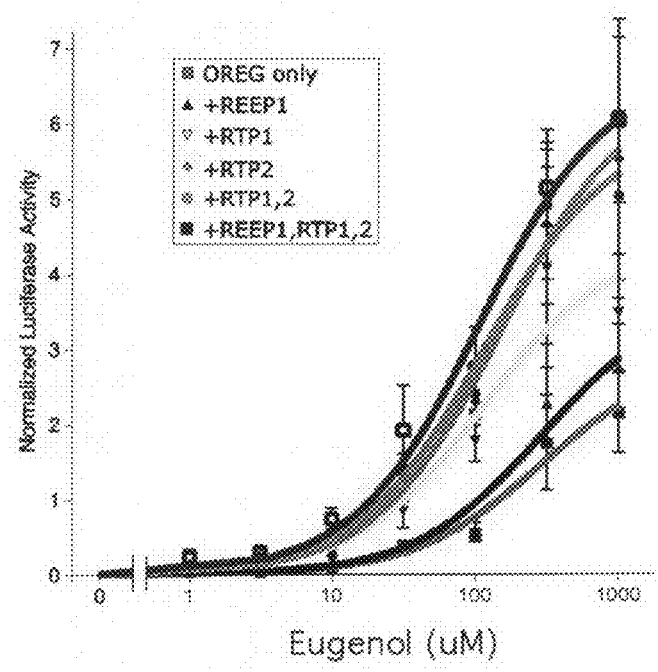

FIGURE 11
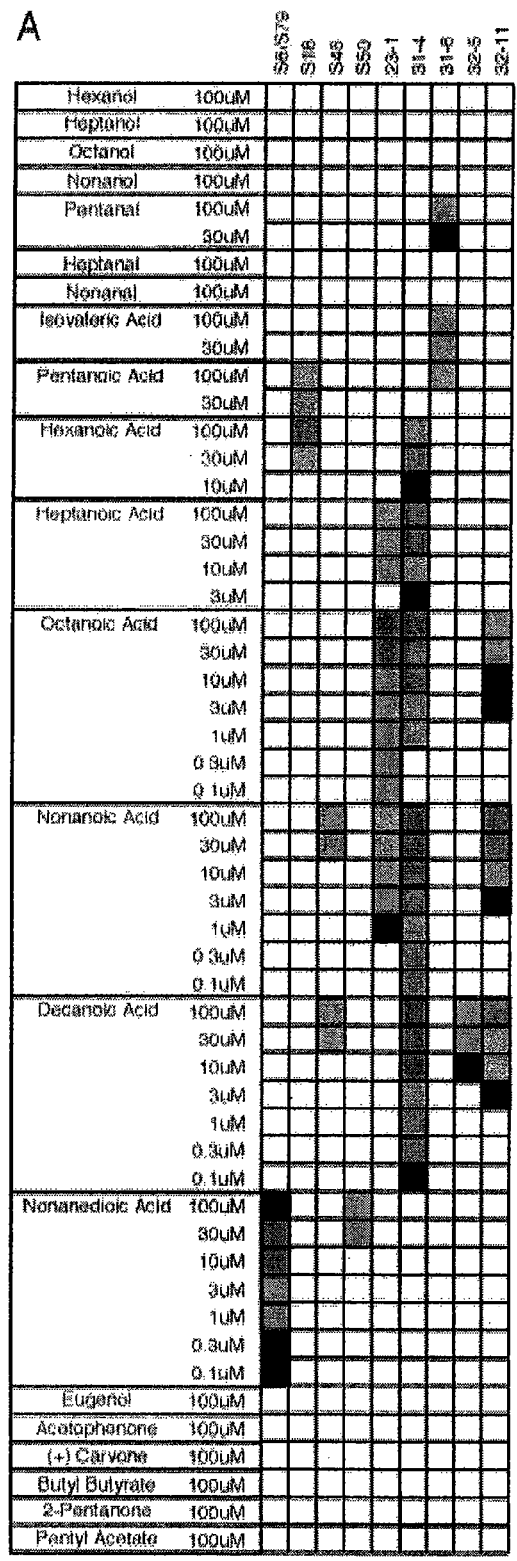
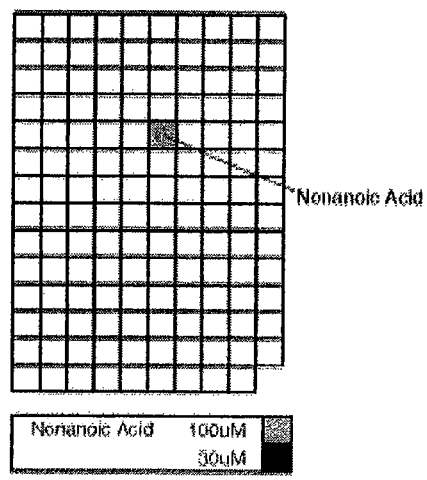
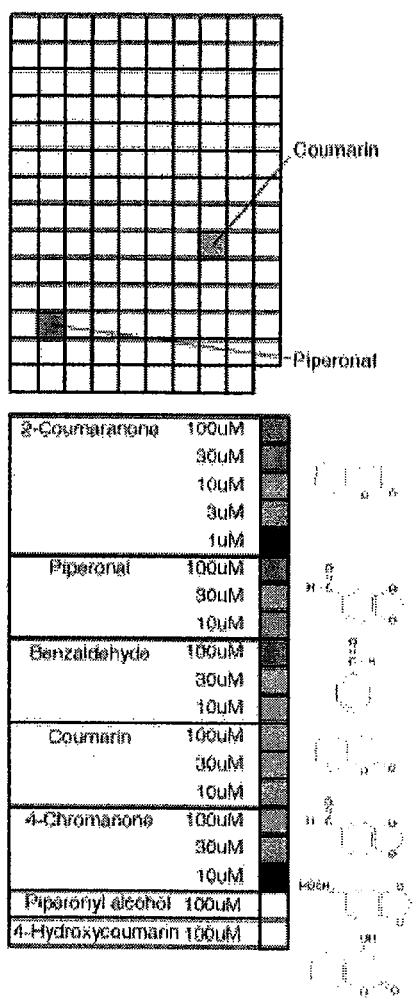

FIGURE 12
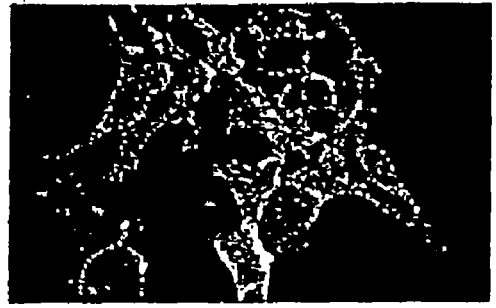
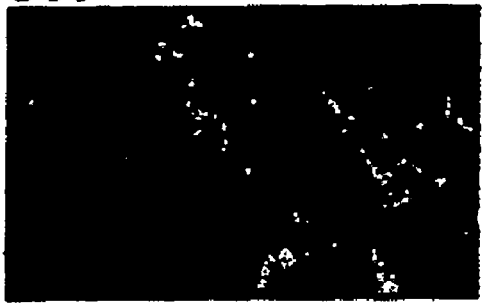

FIGURE 14

SEQ ID NO: 1 (murine REEP1 nucleic acid sequence)
ATGGTGTCGTGGATCATCTCCAGGCTGGTGGTGCTTATATTTGGCACCCTTTA
TCCTGCATATTATTCATACAAGGCTGTGAAGTCCAAGGACATTAAAGAATAT
GTCAAATGGATGATGTATTGGATTATATTTGCCCTCTTCACCACGGCAGAGAC
GTTCACAGACATCTTCCTTTGCTGGTTTCCATTCTATTATGAACTAAAAATAG
CGTTTGTAGCCTGGCTGCTGTCTCCCTATACAAAAGGATCCAGCCTCCTGTAC
AGGAAGTTTGTTCATCCCACATTGTCTTCAAAAGAAAAGGAAATCGATGACT
GCCTGGTCCAAGCAAAAGATCGAAGCTATGACGCCCTTGTGCACTTTGGGAA
GCGGGGCTTGAATGTGGCAGCCACTGCAGCTGTGATGGCTGCCTCCAAGGGA
CAGGGTGCCTTGTCAGAGAGACTCCGGAGCTTCAGCATGCAGGACCTCACCA
CCATCAGGGGTGATGGTGCTCCTGCTCCCTCGGGCCCTCCTCCACCAGGGACT
GGGCGGTCCAGCGGCAAACACAGCCAGCCCAAGATGTCCAGGAGTGCTTCTG
AGAGTGCCGGCAGCTCGGGCACCGCCTAG SEQ ID NO: 21 (murine REEP1 amino acid sequence)
MVSWIISRLVVLIFGTLYPAYYSYKAVKSKDIKEYVKWMMYWIIFALFTTAETFT
DIFLCWFPFYYELKIAFVAWLLSPYTKGSSLLYRKFVHPTLSSKEKEIDDCLVQAK
DRSYDALVHFGKRGLNVAATAAVMAASKGQGALSERLRSFSMQDLTTIRGDGA
PAPSGPPPPGTGRSSGKHSQPKMSRSASESAGSSGTA

FIGURE 15

SEQ ID NO: 2 (murine REEP2 nucleic acid sequence)
ATGGTGTCCTGGATCATCTCTCGCCTGGTGGTGCTCATCTTTGGCACCCTGTA
CCCAGCCTATTCTTCCTACAAGGCCGTGAAGACCAAAAACGTGAAGGAATAC
GTAAAATGGATGATGTATTGGATAGTCTTCGCCTTCTTCACCACAGCTGAGAC
ACTTACAGATATAATACTGTCCTGGTTCCCCTTCTACTTTGAGCTCAAGATTG
CCTTTGTGATATGGCTGTTGTCCCCTTACACCAAGGGCTCCAGTGTCCTCTAC
CGCAAGTTCGTGCACCCAACACTGTCCAACAAGGAAAAGGAGATCGACGAA
TACATCACACAAGCTCGAGACAAGAGCTATGAGACGATGATGAGGGTGGGC
AAGAGGGGCCTGAACCTGGCTGCCAATGCTGCAGTCACAGCTGCTGCCAAGG
GCCAGGGGGTGCTGTCGGAAAAGCTGCGGAGCTTCAGCATGCAGGACCTGAC
TCTCATTCGAGATGAGGATGCGTTACCGCTGCAGGGGCCAGATGGCCGCCTC
CAACCCGGCCCCGTGGGTCTCCTGGACACTATTGAGGACTTAGGAGATGAGC
CTGCCCTAAGTCTAAGGTCTAGCACAAGCCAGCCAGATCCCCGGACAGAGAC
CTCAGAAGATGACCTGGGAGACAAGGCACCCAAGAGGACCAAACCTATCAA
AAAAGTACCCAGAGCTGAGCCGCCGGCTTCCAAGACACTGAAGACCCGGCCC
AAGAAGAAGAGTTCTGGAGGGGGCGACTCAGCATGA SEQ ID NO: 22 (murine REEP2 amino acid sequence)
MVSWIISRLVVLIFGTLYPAYSSYKAVKTKNVKEYVKWMMYWIVFAFFTTAETL
TDIILSWFPFYFELKIAFVIWLLSPYTKGSSVLYRKFVHPTLSNKEKEIDEYITQAR
DKSYETMMRVGKRGLNLAANAAVTAAAKGQGVLSEKLRSFSMQDLTLIRDEDA
LPLQGPDGRLQPGPVGLLDTIEDLGDEPALSLRSSTSQPDPRTETSEDDLGDKAPK
RTKPIKKVPRAEPPASKTLKTRPKKKSSGGGDSA

FIGURE 16

SEQ ID NO: 3 (murine REEP3 nucleic acid sequence)
ATGGTGTCCTGGATGATCTCCCGAGCCGTGGTGCTGGTGTTTGGAATGCTCTA
TCCAGCGTACTATTCCTACAAAGCCGTGAAGACGAAAAACGTCAAGGAATAC
GTTCGCTGGATGATGTATTGGATCGTCTTTGCCCTCTACACTGTCATTGAAAC
GGTGGCCGATCAGACACTTGCATGGTTTCCCCTGTACTATGAGCTGAAGATTG
CCTTCGTCATTTGGCTGCTGTCGCCCTACACTAGAGGGGCGAGTTTAATCTAT
AGAAAGTTCCTTCATCCCCTGCTGTCATCAAAGGAAAGGGAAATTGATGATT
ATATTGTCCAAGCCAAAGAAAGAGGCTATGAGACAATGGTGAATTTTGGACG
GCAAGGTTTGAATTTAGCAGCTGCAGCCGCCGTCACTGCAGCAGTGAAGAGC
CAAGGAGCAATAACGGAGCGTCTGCGAAGTTTCAGCATGCATGATCTGACAG
CTATCCAAGGGGATGAGCCCGTGGGACACAGACCCTACCAGACTTTGCCAGA
AGCAAAGAGGAAAGGCAAACAAGCCACCGAGTCACCAGCCTATGGAATTCC
ACTGAAAGATGGAAGTGAGCAGACAGACGAAGAAGCGGAGGGGCCATTCTC
CGATGACGAGATGGTGACTCACAAGGCGCTGAGGCGATCCCAGAGCATGAA
ATCTGTCAAGACCATCAAAGGCCGCAAAGAGGTGCGGTATGGCTCACTAAAA
TATAAAGTGAAGAAGAGACCGCAAGTGTATTTTAG SEQ ID NO: 23 (murine REEP3 amino acid sequence)
MVSWMISRAVVLVFGMLYPAYYSYKAVKTKNVKEYVRWMMYWIVFALYTVIE
TVADQTLAWFPLYYELKIAFVIWLLSPYTRGASLIYRKFLHPLLSSKEREIDDYIV
QAKERGYETMVNFGRQGLNLAAAAAVTAAVKSQGAITERLRSFSMHDLTAIQG
DEPVGHRPYQTLPEAKRKGKQATESPAYGIPLKDGSEQTDEEAEGPFSDDEMVT
HKALRRSQSMKSVKTIKGRKEVRYGSLKYKVKKRPQVYF

FIGURE 17

SEQ ID NO: 4 (murine REEP4 nucleic acid sequence)
ATGGTGTCCTGGATGATCTGTCGCCTGGTAGTGCTCATATTTGGCATGCTGTA
TCCTGCGTATGCTTCCTACAAGGCCGTGAAGAGCAAGAACATTCGAGAATAT
GTACGGTGGATGATGTATTGGATTGTCTTTGCGATCTTCATGGCAGCAGAAAC
CTTCACAGACATCTTCATTTCCTGGTTCCCGTTTTATTACGAGTTCAAGATGGC
TTTTGTGCTGTGGCTGCTCTCACCTTACACCAAGGGGGCCAGCCTGCTTTACC
GAAAGTTTGTCCACCCATCCCTATCCCGCCATGAGAAGGAGATCGACGCGTG
TATCGTGCAGGCAAAGGAGCGCAGCTATGAAACCATGCTCAGTTTTGGGAAG
CGGAGCCTCAACATCGCTGCCTCAGCTGCTGTGCAGGCTGCTACCAAGAGTC
AAGGCGCTCTAGCTGGAAGGCTGCGGAGTTTCTCTATGCAAGACCTGCGCTC
TATCCCTGACACCCCTGTCCCCACCTACCAAGATCCCCTCTACCTGGAAGACC
AGGTACCCCGACGTAGACCCCCTATTGGATACCGGCCAGGCGGCCTGCAGGG
CAGTGACACAGAGGATGAGTGTTGGTCAGACAATGAGATCGTCCCCCAGCCA
CCTGTTCGGCCCCGAGAGAAGCCTCTAGGCCGCAGCCAGAGCCTTCGGGTGG
TCAAGAGGAAGCCATTGACTCGAGAGGGCACCTCACGCTCCCTGAAGGTCCG
AACCCGGAAAAAGGCCATGCCCTCAGACATGGACAGCTAG SEQ ID NO: 24 (murine REEP4 amino acid sequence)
MVSWMICRLVVLIFGMLYPAYASYKAVKSKNIREYVRWMMYWIVFAIFMAAET
FTDIFISWFPFYYEFKMAFVLWLLSPYTKGASLLYRKFVHPSLSRHEKEIDACIVQ
AKERSYETMLSFGKRSLNIAASAAVQAATKSQGALAGRLRSFSMQDLRSIPDTPV
PTYQDPLYLEDQVPRRRPPIGYRPGGLQGSDTEDECWSDNEIVPQPPVRPREKPL
GRSQSLRVVKRKPLTREGTSRSLKVRTRKKAMPSDMDS

FIGURE 18

SEQ ID NO: 5 (murine REEP5 nucleic acid sequence)
ATGTCCGCAGCCATGAGGGAGAGGTTCGACCGGTTCCTGCACGAGAAGAACT
GCATGACTGATCTCCTCGCCAAGCTCGAGGCCAAGACCGGAGTGAACCGGAG
CTTCATCGCGCTCGGTGTCATCGGACTGGTGGCTTTGTATCTGGTGTTCGGTT
ATGGAGCCTCTCTCCTCTGCAACCTGATAGGTTTCGGATACCCAGCCTACATC
TCAATGAAAGCCATCGAGAGTCCCAACAAAGATGATGACACCCAGTGGCTGA
CGTACTGGGTGGTATATGGTGTGTTCAGCATTGCCGAATTCTTCTCCGATCTC
TTCCTGTCCTGGTTCCCCTTCTACTACATGCTGAAGTGTGGCTTCCTGCTGTGG
TGCATGGCCCCCAGCCCGGCTAATGGGGCTGAGATGCGCTACAGGCGAATCA
TCCGTCCTATCTTCCTCAAGCACGAGTCCCAGGTAGACAGTGTGGTGAAGGA
CGTGAAGGACAAAGCCAAAGAGACTGCAGATGCCATCAGCAAAGAAGTCAA
GAAAGCTACAGTGAACTTGCTGGGCGATGAGAAGAAGAGCACCTGA SEQ ID NO: 25 (murine REEP5 amino acid sequence)
MRERFDRFLHEKNCMTDLLAKLEAKTGVNRSFIALGVIGLVALYLVFGYGASLL
CNLIGFGYPAYISMKAIESPNKDDDTQWLTYWVVYGVFSIAEFFSDLFLSWLPFY
YMLKCGFLLWCMAPSPANGAEMLYRRIIRPIFLRHESQVDSVVKDVKDKAKETA
DAISKEVKKATVNLLGDVKKST

FIGURE 19

SEQ ID NO: 6 (murine REEP6 nucleic acid sequence)
ATGGACGGTCTGCGCCAGCGCTTCGAACGTTTTCTGGAACAGAAGAACGTGG
CCACCGAAGCGCTCGGGGCGCTCGAAGCAAGGACCGGTGTAGAGAAGCGGT
ATCTCGCCGCGGGAGCCCTCGCCCTTCTAGGCCTGTATCTTCTGTTCGGTTAC
GGGGCCTCTCTACTGTGCAATGTCATCGGATTTGTATACCCCGCATATGCTTC
AGTCAAAGCTATCGAGAGCCCAAGCAAGGAAGACGACACTGTGTGGCTAAC
CTACTGGGTGGTGTACGCCCTGTTCGGTCTGGTCGAATTCTTCAGCGATCTAC
TCCTGTTCTGGTTCCCTTTCTACTACGCGGGCAAGTGCGCCTTCCTGTTATTTT
GCATGACGCCCGGACCCTGGAACGGGGCATTACTACTATACCATCGCGTCAT
AAGACCACTCTTTCTAAAGCACCACATGGCTCTAGACAGCGCCGCGAGCCAG
CTAAGCGGAAGAGCATTGGACCTAGCAGCTGGGATAACCCGGGACGTACTTC
AGGCCTTGGCTCGGGGCCGGGCTCTCGTCACCCCAGCATCAACATCGGAACC
CCCAGCCGCTCTGGAACTGGACCCCAAGTAA SEQ ID NO: 26 (murine REEP6 amino acid sequence)
MDGLRQRFERFLEQKNVATEALGALEARTGVEKRYLAAGALALLGLYLLFGYG
ASLLCNVIGFVYPAYASVKAIESPSKEDDTVWLTYWVVYALFGLVEFFSDLLLF
WFPFYYAGKCAFLLFCMTPGPWNGALLLYHRVIRPLFLKHHMALDSAASQLSG
RALDLAAGITRDVLQALARGRALVTPASTSEPPAALELDPK

FIGURE 20

SEQ ID NO: 7 (human REEP1 nucleic acid sequence)
ATGGTGTCATGGATCATCTCCAGGCTGGTGGTGCTTATATTTGGCACCCTTTA
CCCTGCGTATTATTCCTACAAGGCTGTGAAATCAAAGGACATTAAGGAATAT
GTCAAATGGATGATGTACTGGATTATATTTGCACTTTTCACCACAGCAGAGAC
ATTCACAGACATCTTCCTTTGTTGGTTTCCATTCTATTATGAACTAAAAATAG
CATTTGTAGCCTGGCTGCTGTCTCCCTACACAAAAGGCTCCAGCCTCCTGTAC
AGGAAGTTTGTACATCCCACACTATCTTCAAAAGAAAAGGAAATCGATGATT
GTCTGGTCCAAGCAAAAGACCGAAGTTACGATGCCCTTGTGCACTTCGGGAA
GCGGGGCTTGAACGTGGCCGCCACAGCGGCTGTGATGGCTGCTTCCAAGGGA
CAGGGTGCCTTATCGGAGAGACTGCGGAGCTTCAGCATGCAGGACCTCACCA
CCATCAGGGGAGACGGCGCCCTGCTCCCTCGGGCCCCCCACCACCGGGGTC
TGGGCGGGCCAGCGGCAAACACGGCCAGCCTAAGATGTCCAGGAGTGCTTCT
GAGAGCGCTAGCAGCTCAGGCACCGCCTAG SEQ ID NO: 27 (human REEP1 amino acid sequence)
MVSWIISRLVVLIFGTLYPAYYSYKAVKSKDIKEYVKWMMYWIIFALFTTAETFT
DIFLCWFPFYYELKIAFVAWLLSPYTKGSSLLYRKFVHPTLSSKEKEIDDCLVQAK
DRSYDALVHFGKRGLNVAATAAVMAASKGQGALSERLRSFSMQDLTTIRGDGA
PAPSGPPPPGSGRASGKHGQPKMSRSASESASSSGTA

FIGURE 21

SEQ ID NO: 8 (human REEP2 nucleic acid sequence)
ATGGTGTCCTGGATCATCTCTCGCCTGGTGGTGCTCATCTTTGGCACCCTGTA
CCCAGCCTATTCTTCCTACAAGGCCGTGAAGACAAAAAACGTGAAGGAATAT
GTGAAATGGATGATGTACTGGATCGTCTTTGCCTTCTTCACCACGGCCGAGAC
GCTCACGGATATAGTGCTCTCCTGGTTCCCCTTCTACTTTGAACTGAAGATCG
CCTTCGTGATATGGCTGCTGTCCCCTTACACCAAGGGCTCCAGCGTGCTCTAC
CGCAAGTTCGTGCACCCAACGCTGTCCAACAAGGAGAAGGAGATCGACGAG
TACATCACGCAGGCCCGAGACAAGAGCTATGAGACCATGATGAGGGTGGGC
AAGAGGGGCCTGAACCTTGCCGCCAATGCTGCAGTCACAGCTGCCGCCAAGG
GGGTGCTGTCAGAGAAGCTCCGCAGCTTCAGCATGCAGGACCTGACCCTGAT
CCGGGACGAGGACGCACTGCCCCTGCAGAGGCCTGACGGCCGCCTCCGACCC
AGCCCTGGCAGCCTCCTGGACACCATCGAGGACTTAGGAGATGACCCTGCCC
TGAGTCTAAGGTCCAGCACAAACCCGGCAGATTCCCGGACAGAGGCTTCTGA
GGATGACATGGGAGACAAAGCTCCCAAGAGGGCCAAACCCATCAAAAAAGC
GCCCAAAGCTGAGCCACTGGCTTCCAAGACACTGAAGACCCGGCCCAAGAA
GAAGACCTCTGGCGGGGGCGACTCAGCTTGA SEQ ID NO: 28 (human REEP2 amino acid sequence)
MVSWIISRLVVLIFGTLYPAYSSYKAVKTKNVKEYVKWMMYWIVFAFFTTAETL
TDIVLSWFPFYFELKIAFVIWLLSPYTKGSSVLYRKFVHPTLSNKEKEIDEYITQAR
DKSYETMMRVGKRGLNLAANAAVTAAAKGVLSEKLRSFSMQDLTLIRDEDALP
LQRPDGRLRPSPGSLLDTIEDLGDDPALSLRSSTNPADSRTEASEDDMGDKAPKR
AKPIKKAPKAEPLASKTLKTRPKKKTSGGGDSA

FIGURE 22

SEQ ID NO: 9 (human REEP3 nucleic acid sequence)
ATGGTGTCCTGGATGATCTCCAGAGCCGTGGTGCTGGTGTTTGGAATGCTTTA
TCCTGCATATTATTCATACAAAGCTGTGAAAACAAAAAACGTGAAGGAATAT
GTTCGATGGATGATGTACTGGATTGTTTTGCTCTCTATACTGTGATTGAAAC
AGTAGCCGATCAAACAGTTGCTTGGTTTCCCCTGTACTATGAGCTGAAGATTG
CTTTTGTCATATGGCTGCTTTCTCCCTATACCAAAGGAGCAAGTTTAATATAT
AGAAAATTCCTTCATCCACTTCTTTCTTCAAAGGAAAGGGAGATTGATGATTA
TATTGTACAAGCAAAGGAACGAGGCTATGAAACCATGGTAAACTTTGGACGG
CAAGGTTTAAACCTTGCAGCTACTGCTGCTGTTACTGCAGCAGTAAAGGTAAT
TGTTCATTTACCTTTTTAA SEQ ID NO: 29 (human REEP3 amino acid sequence)
MVSWMISRAVVLVFGMLYPAYYSYKAVKTKNVKEYVRWMMYWIVFALYTVIE
TVADQTVAWFPLYYELKIAFVIWLLSPYTKGASLIYRKFLHPLLSSKEREIDDYIV
QAKERGYETMVNFGRQGLNLAATAAVTAAVKVIVHLPF

FIGURE 23

SEQ ID NO: 10 (human REEP4 nucleic acid sequence)
ATGGTGTCCTGGATGATCTGTCGCCTGGTGGTGCTGGTGTTTGGGATGCTGTG
TCCAGCTTATGCTTCCTATAAGGCTGTGAAGACCAAGAACATTCGTGAATATG
TGCGGTGGATGATGTACTGGATTGTTTTTGCACTCTTCATGGCAGCAGAGATC
GTTACAGACATTTTTATCTCCTGGTTCCCTTTCTACTATGAGATCAAGATGGC
CTTCGTGCTGTGGCTGCTCTCACCCTACACCAAGGGCGCCAGCCTGCTTTACC
GCAAGTTTGTCCACCCGTCCCTGTCCCGCCATGAGAAGGAGATCGACGCGTA
CATCGTGCAGGCCAAGGAGCGCAGCTACGAGACCGTGCTCAGCTTCGGGAAG
CGGGGCCTCAACATTGCCGCCTCCGCTGCTGTGCAGGCTGCCACCAAGAGTC
AGGGGGCGCTGGCCGGCAGGCTGCGGAGCTTCTCCATGCAGGACCTGCGCTC
CATCTCTGACGCACCTGCCCCTGCCTACCATGACCCCCTCTACCTGGAGGACC
AGGTGTCCCACCGGAGGCCACCCATTGGGTACCGGGCCGGGGGCCTGCAGGA
CAGCGACACCGAGGATGAGTGTTGGTCAGATACTGAGGCAGTCCCCCGGGCG
CCAGCCCGGCCCCGAGAGAAGCCCCTAATCCGCAGCCAGAGCCTGCGTGTGG
TCAAGAGGAAGCCACCGGTGCGGGAGGGCACCTCGCGCTCCCTGAAGGTTCG
GACGAGGAAAAAGACTGTGCCCTCAGACGTGGACAGCTAG SEQ ID NO: 30 (human REEP4 amino acid sequence)
MVSWMICRLVVLVFGMLCPAYASYKAVKTKNIREYVRWMMYWIVFALFMAA
EIVTDIFISWFPFYYEIKMAFVLWLLSPYTKGASLLYRKFVHPSLSRHEKEIDAYIV
QAKERSYETVLSFGKRGLNIAASAAVQAATKSQGALAGRLRSFSMQDLRSISDA
PAPAYHDPLYLEDQVSHRRPPIGYRAGGLQDSDTEDECWSDTEAVPRAPARPRE
KPLIRSQSLRVVKRKPPVREGTSRSLKVRTRKKTVPSDVDS

FIGURE 24

SEQ ID NO: 11 (human REEP5 nucleic acid sequence)
ATGTCTGCGGCCATGAGGGAGAGGTTCGACCGGTTCCTGCACGAGAAGAACT
GCATGACTGACCTTCTGGCCAAGCTCGAGGCCAAAACCGGCGTGAACAGGAG
CTTCATCGCTCTTGGTGTCATCGGACTGGTGGCCTTGTACCTGGTGTTCGGTT
ATGGAGCCTCTCTCCTCTGCAACCTGATAGGATTTGGCTACCCAGCCTACATC
TCAATTAAAGCTATAGAGAGTCCCAACAAAGAAGATGATACCCAGTGGCTGA
CCTACTGGGTAGTGTATGGTGTGTTCAGCATTGCTGAATTCTTCTCTGATATCT
TCCTGTCATGGTTCCCCTTCTACTACATGCTGAAGTGTGGCTTCCTGTTGTGGT
GCATGGCCCCGAGCCCTTCTAATGGGGCTGAACTGCTCTACAAGCGCATCAT
CCGTCCTTTCTTCCTGAAGCACGAGTCCCAGATGGACAGTGTGGTCAAGGAC
CTTAAAGACAAGGCCAAAGAGACTGCAGATGCCATCACTAAAGAAGCGAAG
AAAGCTACCGTGAATTTACTGGGTGAAGAAAAGAAGAGCACCTAA SEQ ID NO: 31 (human REEP5 amino acid sequence)
MSAAMRERFDRFLHEKNCMTDLLAKLEAKTGVNRSFIALGVIGLVALYLVFGY
GASLLCNLIGFGYPAYISIKAIESPNKEDDTQWLTYWVVYGVFSIAEFFSDIFLSW
FPFYYMLKCGFLLWCMAPSPSNGAELLYKRIIRPFFLKHESQMDSVVKDLKDKA
KETADAITKEAKKATVNLLGEEKKST

FIGURE 25

SEQ ID NO: 12 (human REEP6 nucleic acid sequence)
ATGGACGGCCTGAGGCAGCGCGTGGAGCACTTCCTGGAGCAAAGGAACCTG
GTCACCGAAGTGCTGGGGGCGCTGGAGGCCAAGACCGGGGTGGAGAAGCGG
TATCTGGCTGCAGGAGCCGTCACTCTGCTAAGCCTGTATCTGCTGTTCGGCTA
CGGAGCGTCTCTGCTGTGCAATCTCATCGGATTTGTGTACCCCGCATATGCCT
CAATCAAAGCTATCGAGAGCCCAAGCAAGGACGACGACACTGTGTGGCTCAC
CTACTGGGTGGTGTACGCCCTGTTTGGGCTGGCCGAGTTCTTCAGCGATCTAC
TCCTGTCCTGGTTCCCTTTCTACTACGTGGGCAAGTGCGCCTTCCTGTTGTTCT
GCATGGCTCCCAGGCCCTGGAACGGGGCTCTCATGCTGTATCAGCGCGTCGT
GCGTCCGCTGTTCCTAAGGCACCACGGGGCCGTAGACAGAATCATGAACGAC
CTCAGCGGGCGAGCCCTGGACGCGGCGGCCGGAATAACCAGGAACGTCAAG
CCAAGCCAGACCCCGCAGCCGAAGGACAAGTGA SEQ ID NO: 32 (human REEP6 amino acid sequence)
MDGLRQRVEHFLEQRNLVTEVLGALEAKTGVEKRYLAAGAVTLLSLYLLFGYG
ASLLCNLIGFVYPAYASIKAIESPSKDDDTVWLTYWVVYALFGLAEFFSDLLLSW
FPFYYVGKCAFLLFCMAPRPWNGALMLYQRVVRPLFLRHHGAVDRIMNDLSGR
ALDAAAGITRNVKPSQTPQPKDK

FIGURE 26

SEQ ID NO: 13 (murine RTP1 nucleic acid)
ATGAGGATTTTTAGACCGTGGAGACTGCGCTGCCCTGCCTTACACTTACCCTC
TTTCCCCACGTTCTCTATAAAGTGTAGTTTGCCTCCTCTTCCCACTGACGAAG
ACATGTGTAAGAGTGTGACCACAGGTGAGTGGAAGAAGGTCTTCTACGAGAA
GATGGAGGAGGTGAAGCCAGCGGACAGCTGGGACTTCATCATAGACCCCAA
CCTCAAGCACAATGTGTTGGCCCCTGGCTGGAAGCAGTACCTGGAACTTCAT
GCCTCAGGCAGGTTCCACTGTTCCTGGTGCTGGCACACCTGGCAGTCACCCCA
TGTAGTCATCCTCTTCCACATGTACCTGGACAAGGCTCAGCGCGCTGGTTCGG
TGCGCATGCGTGTGTTCAAGCAGCTCTGCTACGAGTGCGGTACAGCACGGCT
GGATGAGTCCAGCATGCTGGAGGAGAACATCGAAAGCCTGGTGGACAACCTC
ATCACCAGTTTGCGAGAGCAGTGCTACGGGGAGCGTGGTGGCCACTACCGCA
TCCATGTGGCCAGCCGGCAGGACAACCGGCGACACCGCGGAGAGTTCTGCGA
GGCCTGCCAGGAAGGCATCGTGCACTGGAAGCCCAGTGAGAAGCTGCTGGA
GGAGGAGGCGACCACCTACACCTTCTCCCGTGCTCCCAGCCCCACCAAACCG
CAGGCTGAAACAGGCTCAGGCTGCAACTTCTGCTCCATTCCCTGGTGCTTATT
TTGGGCCACGGTTTTGATGCTCATCATCTACCTGCAATTCTCCTTCCGTACTTC
TGTCTAA SEQ ID NO: 33 (murine RTP1 amino acid sequence)
MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGHYRIHVASRQDNRRHRGEFCEACQEGIVHWKPSEKLLEEEATTYT
FSRAPSPTKPQAETGSGCNFCSIPWCLFWATVLMLIIYLQFSFRTSV

FIGURE 27

SEQ ID NO: 14 (murine RTP2 nucleic acid sequence)
ATGTCCACCAGCCTGACCACTTGTGAGTGGAAGAAGGTCTTCTACGAGAAGA
TGGAGGTGGCCAAGCCAGCGGACAGCTGGGAGCTCATCATAGACCCCACCCT
CAAGCCCAATGAGCTGGGCCCTGGCTGGAAGCAGTACCTGGAGCAACATGCC
TCAGGCAGGTTCCACTGTTCCTGGTGTTGGCACACATGGCAATCTGCCAATGT
CGTCATTCTCTTCCACATGCACCTGGACCGTGCCCAGCGTGTTGGCTCAGTGC
GCATGCGCGTGTTCAAGCAGCTGTGCTATCAGTGCGGCACGTCGCGGCTGGA
CGAGTCCAGCATGCTGGAGGAGAATATCGAGGGCCTGGTGGACAACCTCATC
ACCAGTCTGCGCGAGCAGTGTTACGATGAGGATGGTGGCCAGTACCGCATCC
ACGTAGCCAGCCGGCCAGACAGCGGATTGCACCGCAGTGAGTTCTGCGAGGC
CTGCCAGGAAGGCATCGTGCACTGGAAGCCCAGCGAAAAGCTGCTGGAGGA
GGATGCCGCCTATACCGATGCCTCCAAGAAGAAGGGCCAGGCTGGTTTTATC
TCCAGCTTCTTCTCATTTCGTTGGTGCCTGTTCTGGGGCACCCTCTGCCTGGTC
ATTGTCTACCTGCAGTTCTTCCGAGGCCGCTCTGGCTTCCTTTAG SEQ ID NO: 34 (murine RTP2 amino acid sequence)
MSTSLTTCEWKKVFYEKMEVAKPADSWELIIDPTLKPNELGPGWKQYLEQHASG
RFHCSWCWHTWQSANVVILFHMHLDRAQRVGSVRMRVFKQLCYQCGTSRLDE
SSMLEENIEGLVDNLITSLREQCYDEDGGQYRIHVASRPDSGLHRSEFCEACQEGI
VHWKPSEKLLEEDAAYTDASKKKGQAGFISSFFSFRWCLFWGTLCLVIVYLQFF
RGRSGFL

FIGURE 28

SEQ ID NO: 15 (murine RTP3 nucleic acid sequence)
ATGATGGAAGAAGACATAGGAGACACAGAGCAATGGCGACATGTGTTCCAG
GAGCTAATGCAAGAGGTGAAACCCTGGCACAAATGGACCCTCATACCAGAC
AAGAACCTTCTTCCCAACGTTTTGAAGCCAGGATGGACGCAATACCAGCAAA
AGACCTTTGCTAGGTTCCACTGTCCTTCCTGCTCTCGAAGTTGGGCATCTGGC
CGAGTTCTGATAGTCTTCCACATGCGGTGGTGTGAGAAGAAGGCCAAGGGGT
GGGTGAAGATGAGGGTGTTTGCTCAGAGATGTAATCAGTGCCCCGAGCCTCC
ATTTGCAACTCCAGAAGTCACTTGGGACAACATCTCAAGGATCTTAACAAC
CTGCTCTTCCAAATTCTGAAGAAGTGCTATAAAGAAGGATTTAAGCAAATGG
GTGAGATTCCTTTGCTAGGGAACACCAGTCTCGAAGGGCCACATGACAGCAG
CAACTGTGAGGCCTGTCTCCTGGGCTTTTGTGCTCAGAATGACTTAGGCCAAG
CCTCAAAACCACCAGCACCCCCATTATCTCCTACCTCCTCAAAGTCAGCCAGG
GAGCCCAAGGTCACTGCCACCTGTAGCAACATTTCCTCCTCACAGCCCTCCTC
TAAAGTACAGATGCCCCAAGCATCAAAAGCGAACCCCCAAGCCAGTAACCCT
ACCAAAAATGACCCCAAAGTTAGCTGCACCTCAAAACCACCAGCACCCCCAT
TATCTCCTACCTCCTTAAAGTCAGCCAGGGAGCCTAAGGTCACTGTCACCTGT
AGCAACATTTCCTCCTCGCGGTCCTCCTCTAAAGTACAGATGCCCCAAGCATC
AAAAGTGAACCCCCAAACCAGTAATCCTACCAAAAATGACCCCAAGATTAGC
TGTACCTCAAAACCATCAACTACTCCAAGACTGACAATACAACAGCTGTCAG
TAGTAAGCCCACCTGCCCCTGCCCCTACATGTGTCATTCAAATGCCTTCTCCC
ACTCCCATCGACGGCAGCAGAGCAGCAGATGTAGCAAAGGAGAACACCAGA
TCCAAGACCCCAAAGGCATTGCTCTCATCCCCTTTATACGTCCCACCCACTTC
CTCCTATGTCCCACCCACTTCCTCCTATGTCCCACCCACTTCCTCCTATGTCCC
GCCCACTTCCTCTTATGTCCCACCCACTTCCTCCTCAGTTATTGTGCCCATTTC
CTCCTCGTGGAGACTACCAGAAAACACTATTTGCCAAGTAGAGAGAAACAGT
CATATCCACCCGCAAAGCCAGTCTTCCTGCTGTGGGGCCTGCTGCGAGTCCTG
GTGTGAGATCTTCAGGTACTCATGCTGTGAGGCCGCCTGTAATTGCATGTCAC
AGAGTCCACTGTGTTGCTTGGCCTTTCTAATCTTGTTCTTATTGCTGTGGTATT
TATTATAA SEQ ID NO: 35 (murine RTP3 amino acid sequence)
MMEEDIGDTEQWRHVFQELMQEVKPWHKWTLIPDKNLLPNVLKPGWTQYQQK
TFARFHCPSCSRSWASGRVLIVFHMRWCEKKAKGWVKMRVFAQRCNQCPEPPF
ATPEVTWDNISRILNNLLFQILKKCYKEGFKQMGEIPLLGNTSLEGPHDSSNCEAC
LLGFCAQNDLGQASKPPAPPLSPTSSKSAREPKVTVTCSNISSSRPSSKVQMPQAS
KVNPQASNPTKNDPKVSCTSKPPAPPLSPTSLKSAREPKVTVTCSNISSSRPSSKV
QMPQASKV

FIGURE 29

SEQ ID NO: 16 (murine RTP4 nucleic acid sequence)
ATGCTGTTCCCCGATGACTTCAGTACTTGGGAGCAGACATTTCAAGAACTGAT
GCAGGAGGAGAAGCCCGGGGCCAAGTGGAGCCTGCATTTGGATAAGAACAT
TGTACCAGATGGTGCAGCCCTGGGATGGAGGCAGCACCAGCAGACAGTGCTT
GGCAGGTTCCAGTGTTCCAGATGCTGCAGAAGTTGGACCTCTGCTCAGGTGA
TGATCTTGTGCCACATGTACCCGGACACTTTGAAATCGCAGGGCCAGGCACG
CATGAGGATCTTTGGTCAGAAGTGCCAGAAGTGTTTTGGATGTCAATTTGAG
ACTCCCAAGTTCTCCACAGAGATCATCAAAAGAATTCTGAATAACCTAGTTA
ATTATATTCTGCAGAGATACTATGGACACAGGAAGATAGCATTGACCTCGAA
TGCATCTTTGGGTGAGAAGGTGACTTTGGATGGGCCCCACGACACACGCAAT
TGTGAGGCATGCAGTCTAAACTCTCATGGAAGATGTGCCCTTGCACACAAAG
TAAAACCACCCAGATCTCCATCTCCATTACCAAATAGTTCCTCCCCATCAAAG
AGCTGCCCTCCTCCGCCTCAGACCCGGAATACGGATTTTGGGAATAAAACTC
TTCAGGATTTTGGGAATAGAACTTTTCAGGGATGCAGAGAGCCCCCCCAACG
TGAAATAGAGCCACCACTATTTCTGTTTTGTCTATTGCTGCATTTGCCCTTTT
TAGTCTTTTCACTAGATAA SEQ ID NO: 36 (murine RTP4 amino acid sequence)
MLFPDDFSTWEQTFQELMQEEKPGAKWSLHLDKNIVPDGAALGWRQHQQTVG
RFQCSRCCRSWTSAQVMILCHMYPDTLKSQGQARMRIFGQKCQKCFGCQFETPK
FSTEIIKRILNNLVNYILQRYYGHRKIALTSNASLGEKVTLDGPHDTRNCEACSLN
SHGRCALAHKVKPPRSPSPLPNSSSPSKSCPPPPQTRNTDFGNKTLQDFGNRTFQG
CREPPQREIEPPLFLFLSIAAFALFSLFTR

FIGURE 30

SEQ ID NO: 17 (human RTP1-A1 nucleic acid sequence)

```
ATGTGTAAAAGCGTGACCACAGATGAGTGGAAGAAAGTCTTCTATGAGAAGATGGAGGAGGCAAAGCCGGCTGACAG
CTGGGACCTCATCATAGACCCCAACCTCAAGCACAATGTGCTGAGCCCTGGTTGGAAGCAGTACCTGGAATTGCATG
CTTCAGGCAGGTTCCACTGCTCCTGGTGCTGGCACACCTGGCAGTCGCCCTACGTGGTCATCCTCTTCCACATGTTC
CTGGACCGCGCCCAGCGGGCGGGCTCGGTGCGCATGCGCGTCTTCAAGCAGCTGTGCTATGAGTGCGGCACGGCGCG
GCTGGACGAGTCCAGCATGCTGGAGGAGAACATCGAGGGCCTGGTGGACAACCTCATCACCAGCCTGCGCGAGCAGT
GCTACGGCGAGCGTGGCGGCCAGTACCGCATCCACGTGGCCAGCCGCCAGGACAACCGGCGGCACCGCGGAGAGTTC
TGCGAGGCCTGCCAGGAGGGCATCGTGCACTGGAAGCCCAGCGAGAAGCTGCTGGAGGAGGAGGCGACCACCTACAC
CTTCTCCCGGGCGCCCAGCCCCACCAAGTCGCAGGACCAGACGGGCTCAGGCTGGAACTTCTGCTCTATCCCCTGGT
GCTTGTTTTGGGCCACGGTCCTGCTGCTGATCATCTACCTGCAGTTCTCTTTCCGTAGCTCCGTATAA
```

SEQ ID NO: 37 (human RTP1 amino acid sequence)

```
MRIFRPWRLRCPALHLPSLSVFSLRWKLPSLTTDETMCKSVTTDEWKKVFYEKMEEAKPADSWDLIIDPNLK
HNVLSPGWKQYLELHASGRFHCSWCWHTWQSPYVVILFHMFLDRAQRAGSVRMRVFKQLCYECGTARLDE
SSMLEENIEGLVDNLITSLREQCYGERGGQYRIHVASRQDNRRHRGEFCEACQEGIVHWKPSEKLLEEEA
TTYTFSRAPSPTKSQDQTGSGWNFCSIPWCLFWATVLLLIIYLQFSFRSSV
```

FIGURE 31

SEQ ID NO: 18 (human RTP2 nucleic acid sequence)
ATGTGTACCAGCTTGACCACTTGTGAGTGGAAGAAAGTCTTCTATGAAGA
TGGAGGTGGCAAAGCCAGCGGACAGCTGGGAGCTCATCATAGACCCCAACCT
CAAGCCCAGTGAGCTGGCCCCTGGCTGGAAGCAGTACCTGGAGCAGCACGCC
TCAGGCAGGTTCCACTGCTCCTGGTGCTGGCACACCTGGCAGTCTGCCCATGT
GGTCATCCTCTTCCACATGTTCCTGGACCGCGCCCAGCGGGCGGGCTCGGTGC
GCATGCGCGTCTTCAAGCAGCTGTGCTATGAGTGCGGCACGGCGCGGCTGGA
CGAGTCCAGCATGCTGGAGGAGAACATCGAGGGCCTGGTGGACAACCTCATC
ACCAGCCTGCGCGAGCAGTGCTACGAGGAGGATGGTGGCCAGTACCGCATCC
ACGTGGCCAGCCGCCCGGACAGCGGGCCGCATCGTGCAGAGTTCTGTGAGGC
CTGCCAGGAGGGCATCGTTCACTGGAAGCCCAGCGAGAAGCTGCTGGAGGA
GGAGGTGACCACCTACACCTCTGAAGCCTCCAAGCCGAGGGCCCAGGCGGG
ATCCGGCTACAACTTCTTGTCTCTTCGCTGGTGCCTCTTCTGGGCCTCTCTCTG
CCTGCTCGTTGTTTACCTGCAGTTCTCCTTCCTCAGTCCTGCCTTCTTTTAG SEQ ID NO: 38 (human RTP2 amino acid sequence)
MCTSLTTCEWKKVFYEKMEVAKPADSWELIIDPNLKPSELAPGWKQYLEQHAS
GRFHCSWCWHTWQSAHVVILFHMFLDRAQRAGSVRMRVFKQLCYECGTARLD
ESSMLEENIEGLVDNLITSLREQCYEEDGGQYRIHVASRPDSGPHRAEFCEACQE
GIVHWKPSEKLLEEEVTTYTSEASKPRAQAGSGYNFLSLRWCLFWASLCLLVVY
LQFSFLSPAFF

FIGURE 32

SEQ ID NO: 19 (human RTP3 nucleic acid sequence)
ATGGCTGGGGACACAGAAGTGTGGAAGCAAATGTTTCAGGAGTTAATGCGGG
AGGTGAAGCCATGGCACAGGTGGACCCTGAGACCAGACAAGGGCCTTCTTCC
CAACGTCCTGAAGCCAGGCTGGATGCAATACCAGCAGTGGACCTTCGCCAGG
TTCCAGTGCTCCTCCTGCTCTCGTAACTGGGCCTCTGCCCAAGTTCTGGTCCTT
TTCCACATGAACTGGAGTGAGGAGAAGTCCAGGGGCCAGGTGAAGATGAGG
GTGTTTACCCAGAGATGTAAGAAGTGCCCCAACCTCTGTTTGAGGACCCTG
AGTTCACACAAGAGAACATCTCAAGGATCCTGAAAAACCTGGTGTTCCGAAT
TCTGAAGAAATGCTATAGAGGAAGATTTCAGTTGATAGAGGAGGTTCCTATG
ATCAAGGACATCTCTCTTGAAGGGCCACACAATAGTGACAACTGTGAGGCAT
GTCTGCAGGGCTTCTGTGCTGGGCCCATACAGGTTACAAGCCTCCCCCCATCT
CAGACCCCAAGAGTACACTCCATTTACAAGGTGGAGGAGGTAGTTAAGCCCT
GGGCCTCAGGAGAGAATGTCTATTCCTACGCATGCCAAAACCACATCTGTAG
GAACTTAAGCATTTTCTGCTGTTGTGTCATTCTCATTGTTATCGTGGTGATTGT
TGTAAAAACTGCTATATGA SEQ ID NO: 39 (human RTP3 amino acid sequence)
MAGDTEVWKQMFQELMREVKPWHRWTLRPDKGLLPNVLKPGWMQYQQWTF
ARFQCSSCSRNWASAQVLVLFHMNWSEEKSRGQVKMRVFTQRCKKCPQPLFED
PEFTQENISRILKNLVFRILKKCYRGRFQLIEEVPMIKDISLEGPHNSDNCEACLQG
FCAGPIQVTSLPPSQTPRVHSIYKVEEVVKPWASGENVYSYACQNHICRNLSIFCC
CVILIVIVVIVVKTAI

FIGURE 33

SEQ ID NO: 20 (human RTP4 nucleic acid sequence)
ATGGTTGTAGATTTCTGGACTTGGGAGCAGACATTTCAAGAACTAATCCAAG
AGGCAAAACCCCGGGCCACATGGACGCTGAAGTTGGATGGCAACCTTCAGCT
AGACTGCCTGGCTCAAGGGTGGAAGCAATACCAACAGAGAGCATTTGGCTGG
TTCCGGTGTTCCTCCTGCCAGCGAAGTTGGGCTTCCGCCAAGTTGCAGATTCT
GTGCCACACGTACTGGGAGCACTGGACATCCCAGGGTCAGGTGCGTATGAGG
CTCTTTGGCCAAAGGTGCCAGAAGTGCTCCTGGTCCCAATATGAGATGCCTG
AGTTCTCCTCGGATAGCACCATGAGGATTCTGAGCAACCTGGTGCAGCATAT
ACTGAAGAAATACTATGGAAATGGCATGAGGAAGTCTCCAGAAATGCCAGTA
ATCCTGGAAGTGTCCCTGGAAGGATCCCATGACACAGCCAATTGTGAGGCAT
GCACTTTGGGCATATGTGGACAGGGCTTAAAAAGCTACATGACAAAGCCGTC
CAAATCCCTACTCCCCCACCTAAAGACTGGGAATTCCTCACCTGGAATTGGTG
CTGTGTACCTCGCAAACCAAGCCAAGAACCAGTCAGATGAGGCAAAAGAGG
CTAAGGGGAGTGGGTATGAGAAATTAGGGCCCAGTCGAGACCCAGATCCACT
GAACATCTGTGTCTTTATTTTGCTGCTTGTATTTATTGTAGTCAAATGCTTTAC
ATCAGAATGA SEQ ID NO: 40 (human RTP4 amino acid sequence)
MVVDFWTWEQTFQELIQEAKPRATWTLKLDGNLQLDCLAQGWKQYQQRAFG
WFRCSSCQRSWASAKLQILCHTYWEHWTSQGQVRMRLFGQRCQKCSWSQYEM
PEFSSDSTMRILSNLVQHILKKYYGNGMRKSPEMPVILEVSLEGSHDTANCEACT
LGICGQGLKSYMTKPSKSLLPHLKTGNSSPGIGAVYLANQAKNQSDEAKEAKGS
GYEKLGPSRDPDPLNICVFILLLVFIVVKCFTSE

Figure 35.
mRTP1 
A 
B 
C 
D 
E 

Figure 36.
SEQ ID NO: 41 (murine amino acid sequence for RTP1-A)

MEEVKPADSWDFIIDPNLKHNVLAPGWKQYLELHASGRFHCSWCWHTWQSPH
VVILFHMYLDKAQRAGSVRMRVFKQLCYECGTARLDESSMLEENIESLVDNLIT
SLREQCYGERGGHYRIHVASRQDNRRHRGEFCEACQEGIVHWKPSEKLLEEEAT
TYTFSRAPSPTKPQAETGSGCNFCSIPWCLFWATVLMLIIYLQFSFRTSV

Figure 37.
SEQ ID NO: 42 (murine amino acid sequence for RTP1-B)
MYLDKAQRAGSVRMRVFKQLCYECGTARLDESSMLEENIESLVDNLITSLREQC
YGERGGHYRIHVASRQDNRRHRGEFCEACQEGIVHWKPSEKLLEEEATTYTFSR
APSPTKPQAETGSGCNFCSIPWCLFWATVLMLIIYLQFSFRTSV

Figure 38.
SEQ ID NO: 43 (murine amino acid sequence for RTP1-C)
MLEENIESLVDNLITSLREQCYGERGGHYRIHVASRQDNRRHRGEFCEACQEGIV
HWKPSEKLLEEEATTYTFSRAPSPTKPQAETGSGCNFCSIPWCLFWATVLMLIIYL
QFSFRTSV

Figure 39.
SEQ ID NO: 44 (murine amino acid sequence for RTP1-D)

MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGHYRIHVASRQDNRRHRGEFCEACQEGIVHWKPSEKLLEEEATTYT
FSRAPSPTKPQAETGSGC

Figure 40.
SEQ ID NO: 45 (murine amino acid sequence for RTP1-E)
MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGH

Figure 45.
SEQ ID NO: 46 (murine amino acid sequence for RTP1-A1)

MCKSVTTGEWKKVFYEKMEEVKPADSWDFIIDPNLKHNVLAPGWKQYLELHAS
GRFHCSWCWHTWQSPHVVILFHMYLDKAQRAGSVRMRVFKQLCYECGTARLD
ESSMLEENIESLVDNLITSLREQCYGERGGHYRIHVASRQDNRRHRGEFCEACQE
GIVHWKPSEKLLEEEATTYTFSRAPSPTKPQAETGSGCNFCSIPWCLFWATVLMLI
IYLQFSFRTSV

SEQ ID NO: 47 (human amino acid sequence for RTP1-A1)
```
  1 MRIFRPWRLR GPALHLPGLG VFGLRWKLPG LTTDETMCKS VTTDBWKKVF YEKMEEAKPA
 61 DSWDLIIDPN LKHNVLSPGW KQYLELHASG RFHCSWCWHT WQSPYVVILF HMFLDRAQRA
121 GSVRMRVFKQ LCYECGTARL.DESSMLEENI EGLVDNLITS LREQCYGERG GQYRIHVASR
181 QDNRRHRGEF CEACQEGIVH WKPSEKLLEE EATTYTFSRA PSPTKSQDQT GSGWNFCSIP
241 WCLFWATVLL LIIYLQFSFR SSV
```

Figure 46.
SEQ ID NO: 48 (murine amino acid sequence for RTP1-D1)

MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGHYRIHVASRQDNRRHRGEFCEACQEGIVHWKPSEKLLEEEA

Figure 47.
SEQ ID NO: 49 (murine amino acid sequence for RTP-D2)

MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGHYRIHVASRQDNRRHRGEFCEA

Figure 48.
SEQ ID NO: 50 (murine amino acid sequence for RTP-D3)

MRIFRPWRLRCPALHLPSFPTFSIKCSLPPLPTDEDMCKSVTTGEWKKVFYEKME
EVKPADSWDFIIDPNLKHNVLAPGWKQYLELHASGRFHCSWCWHTWQSPHVVI
LFHMYLDKAQRAGSVRMRVFKQLCYECGTARLDESSMLEENIESLVDNLITSLR
EQCYGERGGHYRIHVASRQDNRRHRGEFCEACQEGIVHWKPSEKLLEEEATTYT
FSRAPSPTKPQAETGSGCNFCSIPWCLFWATVLMLII

FIGURE 50
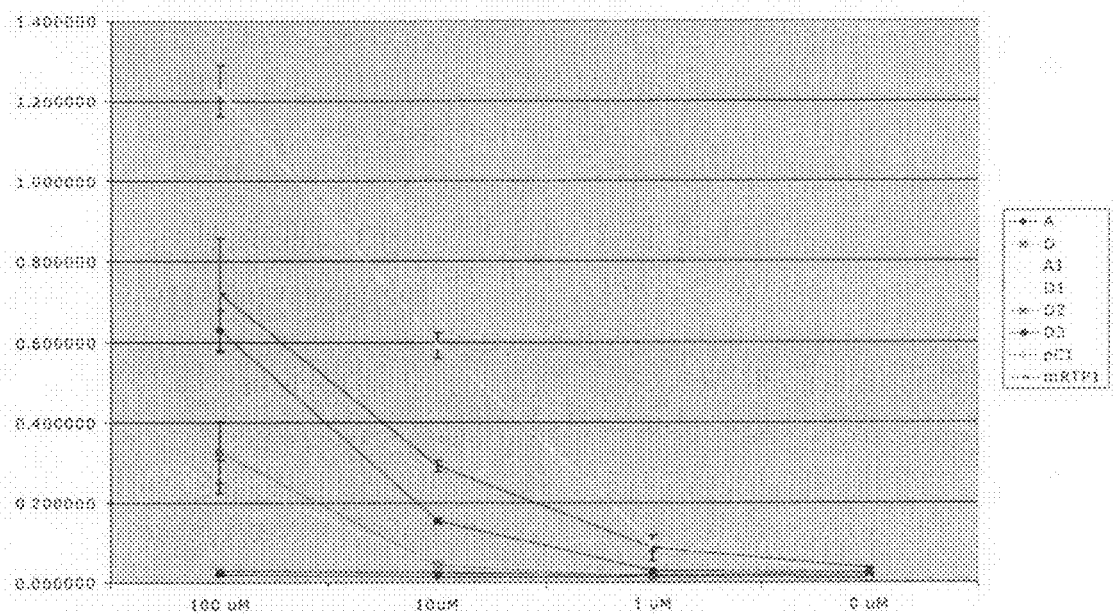
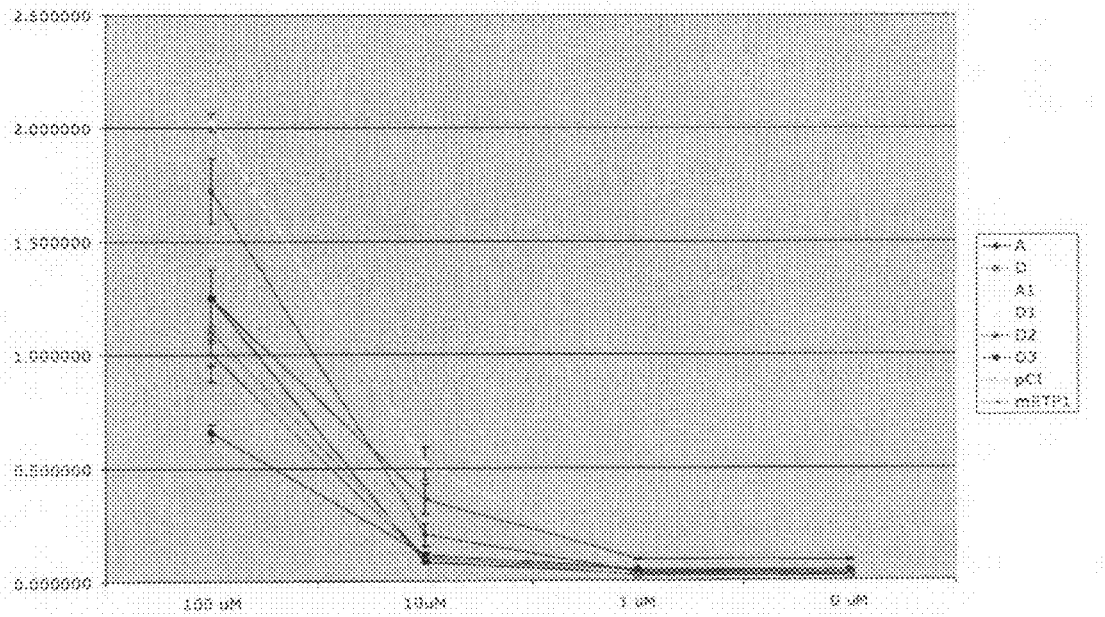

FIGURE 50
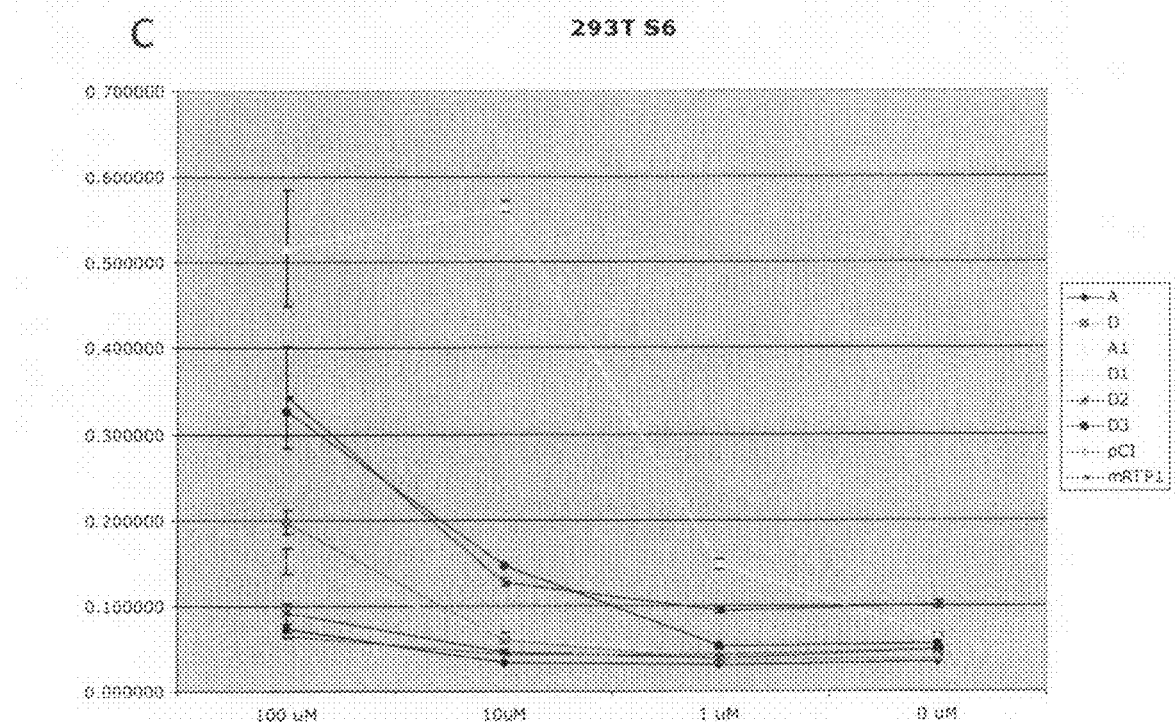
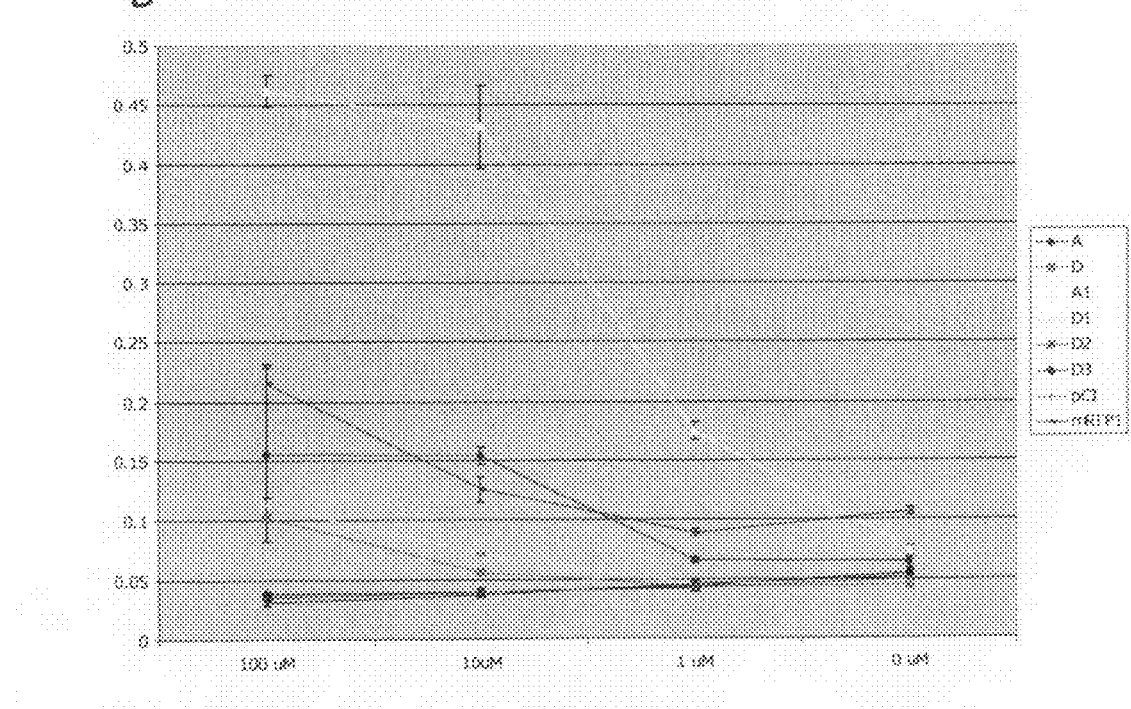

MODULATORS THAT PROMOTE CELL SURFACE EXPRESSION OF ODORANT RECEPTORS

CROSS REFERENCE TO RELATED APPLICATIONS

The present application is a continuation of allowed U.S. patent application Ser. No. 11/156,516, filed Jun. 20, 2005, which issued on Sep. 16, 2008 as U.S. Pat. No. 7,425,445, which claims priority to expired U.S. Provisional Application Ser. No. 60/581,087, filed Jun. 18, 2004, and expired U.S. Provisional Application Ser. No. 60/582,011, filed Jun. 22, 2004, each of which is herein incorporated by reference in their entireties.

STATEMENT REGARDING FEDERALLY SPONSORED RESEARCH OR DEVELOPMENT

This invention was made with government support under Grant No. DC05782 awarded by the National Institutes of Health. The government has certain rights in the invention.

FIELD OF THE INVENTION

The present invention relates to polypeptides capable of promoting odorant receptor cell surface localization and odorant receptor functional expression. The present invention further provides assays for the detection of ligands specific for various odorant receptors. Additionally, the present invention provides methods of screening for odorant receptor accessory protein polymorphisms and mutations associated with disease states, as well as methods of screening for therapeutic agents, ligands, and modulators of such proteins.

BACKGROUND OF THE INVENTION

Olfactory dysfunction arises from a variety of causes and profoundly influences a patient's quality of life. Approximately 2 million Americans experience some type of olfactory dysfunction. Studies show that olfactory dysfunction affects at least 1% of the population under the age of 65 years, and well over 50% of the population older than 65 years. The sense of smell determines the flavor of foods and beverages and serves as an early warning system for the detection of environmental hazards, such as spoiled food, leaking natural gas, smoke, or airborne pollutants. The losses or distortions of smell sensation can adversely influence food preference, food intake and appetite.

Olfactory disorders are classified as follows: 1) anosmia: inability to detect qualitative olfactory sensations (e.g., absence of smell function), 2) partial anosmia: ability to perceive some, but not all, odorants, 3) hyposmia or microsmia: decreased sensitivity to odorants, 4) hyperosmia: abnormally acute smell function, 5) dysosmia (cacosmia or parosmia): distorted or perverted smell perception or odorant stimulation, 6) phantosmia: dysosmic sensation perceived in the absence of an odor stimulus (a.k.a. olfactory hallucination), and 7) olfactory agnosia: inability to recognize an odor sensation.

Olfactory dysfunction is further classified as 1) conductive or transport impairments from obstruction of nasal passages (e.g., chronic nasal inflammation, polyposis, etc.), 2) sensorineural impairments from damage to neuroepithelium (e.g., viral infection, airborne toxins, etc.), 3) central olfactory neural impairment from central nervous system damage (e.g., tumors, masses impacting on olfactory tract, neurodegenerative disorders, etc.). These categories are not mutually exclusive. For example, viruses can cause damage to the olfactory neuroepithelium and they may also be transported into the central nervous system via the olfactory nerve causing damage to the central elements of the olfactory system.

Smelling abilities are initially determined by neurons in the olfactory epithelium, the olfactory sensory neurons (hereinafter "olfactory neurons). In olfactory neurons, odorant receptor (hereinafter "OR") proteins, members of the G-protein coupled receptor (hereinafter "GPCR") superfamily, are synthesized in the endoplasmic reticulum, transported, and eventually concentrated at the cell surface membrane of the cilia at the tip of the dendrite. Considering that ORs have roles in target recognition of developing olfactory axons, OR proteins are also present at axon terminals (see, e.g., Mombaerts, P., (1996) Cell 87, 675-686; Wang, F., et al. (1998) Cell 93, 47-60; each herein incorporated by reference in their entireties). In rodents, odorants are transduced by as many as 1000 different ORs encoded by a multigene family (see, e.g., Axel, R. (1995) Sci Am 1273, 154-159; Buck, L., and Axel, R. (1991) Cell 65, 175-187; Firestein, S. (2001) Nature 413, 211-218; Mombaerts, P. (1999) Annu Rev Neurosci 22, 487-509; Young, J. M., et al., (2002) Hum Mol Genet 11, 535-546; Zhang, X., and Firestein, S. (2002) Nat Neurosci 5, 124-133; each herein incorporated by reference in their entirety). Each olfactory neuron expresses only one type of the OR, forming the cellular basis of odorant discrimination by olfactory neurons (see, e.g., Lewcock, J. W., and Reed, R. R. (2004) Proc Natl Acad Sci USA; Malnic, B., et al., (1999) Cell 96, 713-723; Serizawa, S., et al., (2003) Science 302, 2088-2094; each herein incorporated by reference in their entirety).

What is needed is a better understanding of olfactory sensation. What is further needed is a better understanding of odorant receptor function.

SUMMARY OF THE INVENTION

The present invention relates to polypeptides capable of promoting odorant receptor cell surface localization and odorant receptor functional expression. The present invention further provides assays for the detection of ligands specific for various odorant receptors. Additionally, the present invention provides methods of screening for odorant receptor accessory protein polymorphisms and mutations associated with disease states, as well as methods of screening for therapeutic agents, ligands, and modulators of such proteins.

In preferred embodiments, the present invention provides a method for identifying an odorant receptor ligand, comprising the steps of a) providing i) a cell line or cell membranes thereof comprising an odorant receptor and a reporting agent, and ii) a test compound; b) exposing the test compound to the cell line; and c) measuring the activity of the reporting agent. In some embodiments, the cell line expresses REEP1, RTP1, RTP2, RTP1-A, RTP1-B, RTP1-C, RTP1-D, and RTP1-E, RTP1-A1, RTP1-D1, RTP-D2, and RTP1-D3. In some embodiments, the cell line is a heterologous cell line or a natural cell line. In some embodiments, the cell line is a 293T cell line. In preferred embodiments, the odorant receptor is a human odorant receptor. In other preferred embodiments, the test compound is an odiferous molecule. In even further embodiments, the reporting agent is regulated by a cAMP responsive element. In preferred embodiments, the cell line further comprises $G_{\alpha olf}$. In other embodiments, the odorant receptor is a murine odorant receptor. In other embodiments, the odorant receptor is a synthetic odorant receptor. In preferred embodiments, the odorant receptor comprises S6/79, S18, S46, S50, MOR23-1, MOR31-4, MOR31-6, MOR32-5 and/or MOR32-11. In other embodiments, the reporting agent is an illuminating agent. In even other embodiments, the illuminating agent is luciferase. In alternate embodiments, the method further comprises the step of detecting the presence or absence of an odorant receptor ligand based upon the reporting agent activity.

In preferred embodiments, the present invention provides a cell line expressing an odorant receptor, wherein the expression is localized to the cell surface. In preferred embodiments, the cell line comprises a heterologous gene. In preferred embodiments, the heterologous gene comprises one or more of REEP1, RTP1, and RTP2. In other preferred embodiments, the cell line is a 293T cell line. In some embodiments, the odorant receptor is a human odorant receptor. In preferred embodiments, the odorant receptor is tagged with a reporting agent. In some embodiments, the reporting agent is an illuminating reporting agent. In some embodiments, the illuminating reporting agent comprises glutathione-S-transferase (GST), c-myc, 6-histidine (6×-His), green fluorescent protein (GFP), maltose binding protein (MBP), influenza A virus haemagglutinin (HA), β-galactosidase, or GAL4. In preferred embodiments, the cell line further comprises $G_{\alpha olf}$ expression. In preferred embodiments, the odorant receptor is a murine odorant receptor. In some embodiments, the odorant receptor is a synthetic odorant receptor. In preferred embodiments, the odorant receptor comprises S6/79, S18, S46, S50, MOR23-1, MOR31-4, MOR31-6, MOR32-5 and MOR32-11.

The present invention further provides an isolated nucleic acid comprising a sequence encoding a protein comprising SEQ ID NOs: 21, 27, 33, 34, 37, 38, and 41-50, and variants thereof that are at least 80% identical to SEQ ID NOs: 21, 27, 33, 34, 37, 38, and 41-50. In preferred embodiments, the sequence is operably linked to a heterologous promoter. In preferred embodiments, the sequence is contained within a vector. In preferred embodiments, the vector is within a host cell.

The present invention also provides isolated and purified nucleic acid sequences that hybridize under conditions of high stringency to a nucleic acid comprising SEQ ID NOs: 1, 7, 13, 14, 17 and/or 18. In preferred embodiments, the sequence is operably linked to a heterologous promoter. In preferred embodiments, the sequence is contained within a vector. In some embodiments, the host vector is within a host cell. In further preferred embodiments, the host vector is expressed in a host cell. In preferred embodiments, the host cell is located in an organism, wherein the organism is a non-human animal. In preferred embodiments, the present invention provides a polynucleotide sequence comprising at least fifteen (e.g., 15, 18, 20, 21, 25, 50, 100, 1000, . . . ) nucleotides capable of hybridizing under stringent conditions to the isolated nucleotide sequence.

In preferred embodiments, the present invention provides a polypeptide encoded by a nucleic acid selected from the group consisting of SEQ ID NOs: 1, 7, 13, 14, 17 and 18 and variants thereof that are at least 80% identical to SEQ ID NOs: 1, 7, 13, 14, 17 and 18. In further embodiments, the protein is at least 90% identical to SEQ ID NOs: 1, 7, 13, 14, 17 and 18. In even further embodiments, the protein is at least 95% identical to SEQ ID NOs: 1, 7, 13, 14, 17 and 18.

In preferred embodiments, the present invention provides a composition comprising a nucleic acid that inhibits the binding of at least a portion of a nucleic acid selected from the group consisting of SEQ ID NOs: 1, 7, 13, 14, 17 and 18 to their complementary sequences.

In preferred embodiments, the present invention provides a method for detection of a variant REEP polypeptide in a subject, comprising providing a biological sample from a subject, wherein the biological sample comprises a REEP polypeptide; and detecting the presence or absence of a variant REEP polypeptide in the biological sample. In preferred embodiments, the biological sample is selected from the group consisting of a blood sample, a tissue sample, a urine sample, and an amniotic fluid sample. In further embodiments, the subject is selected from the group consisting of an embryo, a fetus, a newborn animal, and a young animal. In further embodiments, the animal is a human. In preferred embodiments, the detecting comprises differential antibody binding. In further embodiments, the detection comprises a Western blot. In some preferred embodiments, the variant REEP polypeptide is a variant REEP1 polypeptide. In further embodiments, the detecting comprises detecting a REEP1 nucleic acid sequence.

In preferred embodiments, the present invention provides a method for detection of a variant RTP polypeptide in a subject, comprising providing a biological sample from a subject, wherein the biological sample comprises a RTP polypeptide; and detecting the presence or absence of a variant RTP polypeptide in the biological sample. In preferred embodiments, the biological sample is selected from the group consisting of a blood sample, a tissue sample, a urine sample, and an amniotic fluid sample. In further embodiments, the subject is selected from the group consisting of an embryo, a fetus, a newborn animal, and a young animal. In further embodiments, the animal is a human. In preferred embodiments, the detecting comprises differential antibody binding. In further embodiments, the detection comprises a Western blot. In some preferred embodiments, the variant RTP polypeptide is a variant RTP1 and/or RTP2 polypeptide. In further embodiments, the detecting comprises detecting a RTP1 and/or RTP2 nucleic acid sequence. In preferred embodiments, the RTP1 variant is selected from the group consisting of RTP1-A1, RTP1-D1, and RTP1-D3.

In preferred embodiments, the present invention provides a kit comprising a reagent for detecting the presence or absence of a variant REEP polypeptide in a biological sample. In some embodiments, the kit further comprises instruction for using the kit for the detecting the presence or absence of a variant REEP polypeptide in a biological sample. In preferred embodiments, the REEP polypeptide is a REEP1 polypeptide. In other embodiments, the REEP polypeptide is selected from the group consisting of REEP1-6. In preferred embodiments, the instructions comprise instructions required by the U.S. Food and Drug Agency for in vitro diagnostic kits. In preferred embodiments, the reagent is one or more antibodies. In preferred embodiments, the biological sample is selected from the group consisting of a blood sample, a tissue sample, a urine sample, and an amniotic fluid sample. In preferred embodiments, the reagents are configured to detect a REEP1 nucleic acid sequence.

In preferred embodiments, the present invention provides a kit comprising a reagent for detecting the presence or absence of a variant RTP polypeptide in a biological sample. In some embodiments, the kit further comprises instruction for using the kit for the detecting the presence or absence of a variant RTP polypeptide in a biological sample. In preferred embodiments, the RTP polypeptide is a RTP1 and/or RTP2 polypeptide. In other embodiments, the RTP polypeptide is selected from the group consisting of RTP1-4. In preferred embodiments, the instructions comprise instructions required by the U.S. Food and Drug Agency for in vitro diagnostic kits. In preferred embodiments, the reagent is one or more antibodies. In preferred embodiments, the biological sample is selected from the group consisting of a blood sample, a tissue sample, a urine sample, and an amniotic fluid sample. In preferred embodiments, the reagents are configured to detect a RTP1 and/or RTP2 nucleic acid sequence. In preferred embodiments, the RTP1 polypeptide is a variant RTP1 polypeptide selected from the group consisting of RTP1-A1, RTP1-D1, and RTP1-D3.

In preferred embodiments, the present invention provides a method for screening compounds, comprising providing a sample expressing a heterologous REEP polypeptide and a test compound; and exposing the sample to the test compound and detecting a biological effect. In preferred embodiments, the REEP polypeptide is selected from the group consisting of REEP1-6. In preferred embodiments, the sample comprises a cell. In preferred embodiments, the sample comprises a tissue. In preferred embodiments, the sample is found in a subject. In some embodiments, the biological effect comprises a change in activity of REEP. In some embodiments, the biological effect comprises a change in expression of REEP.

In preferred embodiments, the present invention provides a method for screening compounds, comprising providing a sample expressing a heterologous RTP polypeptide and a test compound; and exposing the sample to the test compound and detecting a biological effect. In preferred embodiments, the RTP polypeptide is selected from the group consisting of RTP1-4 and RTP1-A1, RTP1-D1, and RTP1-D3. In preferred embodiments, the sample comprises a cell. In preferred embodiments, the sample comprises a tissue. In preferred embodiments, the sample is found in a subject. In some embodiments, the biological effect comprises a change in activity of RTP. In some embodiments, the biological effect comprises a change in expression of RTP.

DESCRIPTION OF THE FIGURES

FIG. 5 shows the REEP and the RTP families. (A) Deduced amino acid sequences of REEP1 (SEQ ID NO: 21). Solid bar indicates putative transmembrane region (TM). The first TM region could function as a signal peptide. (B) Unrooted phylogenetic tree of REEP family members. At least 6 REEP family members (REEP1-6) were identified on the mouse genome. Yeast YOP1P, barley HVA22, and human DPI are homologous to REEP proteins. (C) Deduced amino acid sequences of RTP1 (SEQ ID NO. 33) and RTP2 (SEQ ID NO: 34). Solid bar indicates putative transmembrane domain. Shaded amino acids are conserved between RTP1 and RTP2. There are two more members (RTP3 and 4) on the mouse genome.

(E) cAMP assays. Enhanced cAMP production to various concentrations of eugenol in Hana3A cells when OREG was transfected. In contrast, cAMP production was not different between Hana3A cells and 293T cells expressing $G_{\alpha olf}$ when β2 adrenergic receptor was transfected and isoproterenol was used.

Figure 9:
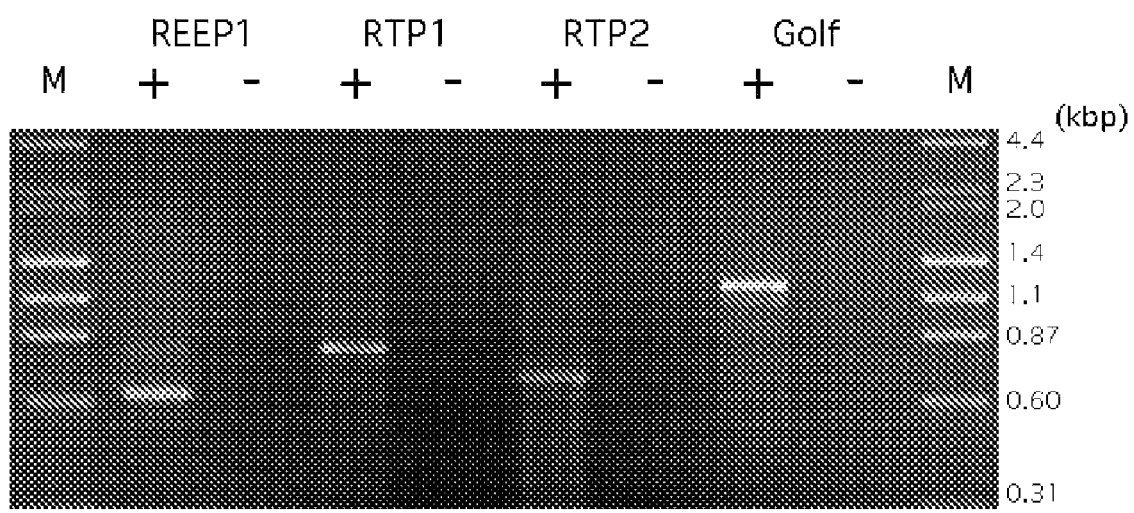

FIG. 9 shows RT-PCR analysis of Hana3A cells; + indicates PCR products using cDNA samples from Hana3A cells as template DNA; – indicates negative controls without reverse transcriptase; M indicates DNA marker.

Figure 10:
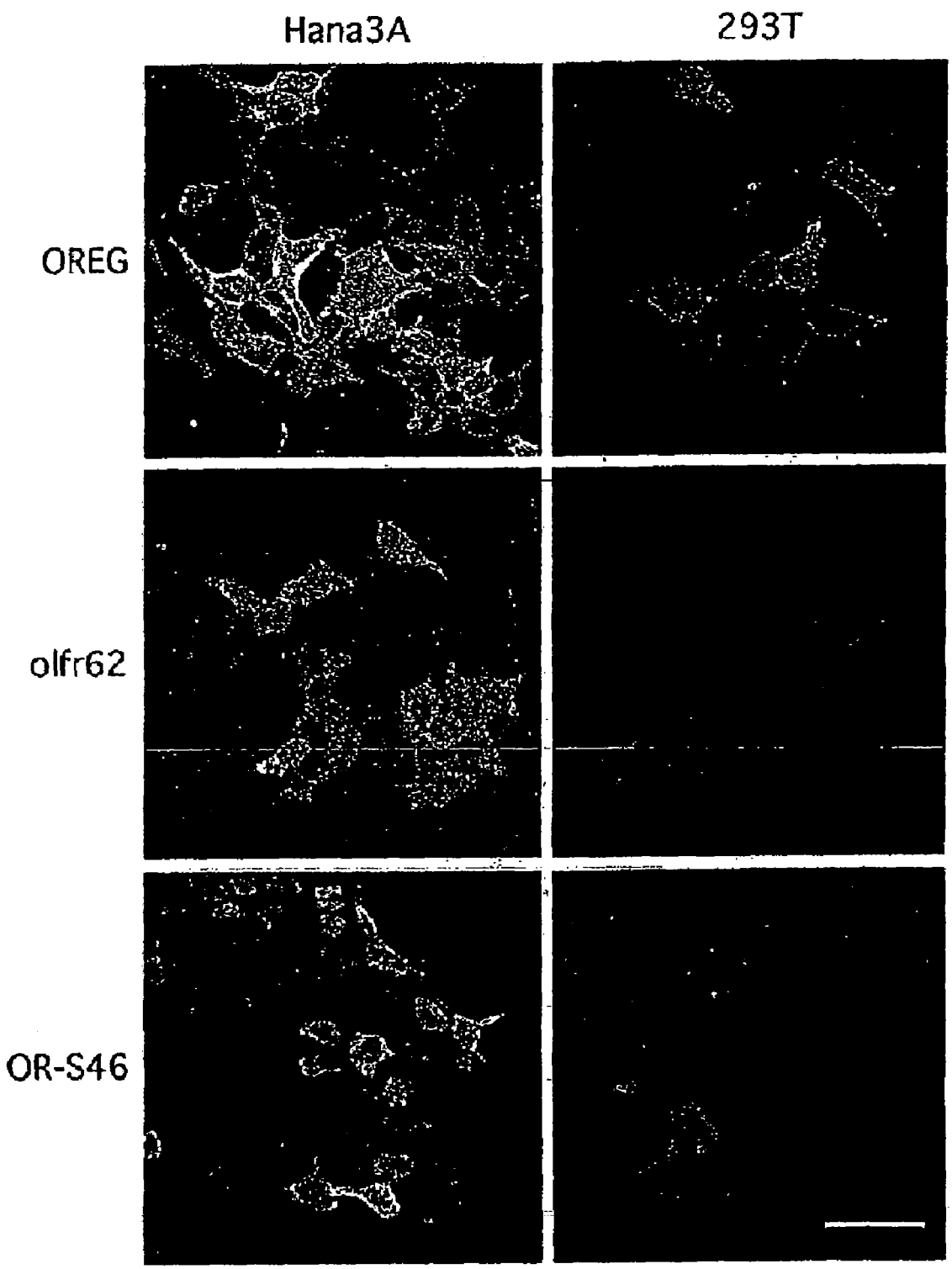

FIG. 10 shows cell-surface expression of odorant receptors in Hana3A and 293T cells. cDNAs encoding three ORs (OREG, olfr62 and OR-S46) were transfected into Hana3A cells or 293T cells. Increased cell-surface staining was seen in Hana3A cells. Scale bar equals to 50 um.

FIG. 11 shows recognition profiles of odorant receptors to odorants. (A) Test odorants are shown on the left. The color indicate relative luciferase activities (N=4). Each OR responded to different subset of odorants. (B) and (C) Normalized luciferase activities (N=4). 139 chemicals were used for initial ligand screening of MOR203-1 and olfr62. MOR203-1 responded to nonanoic acid. Olfr62 responded to five related aromatic compounds.

FIG. 12 shows cell-surface expression of 8 odorant receptors in Hana3A cells. Scale bar equals to 50 um.

Figure 13:
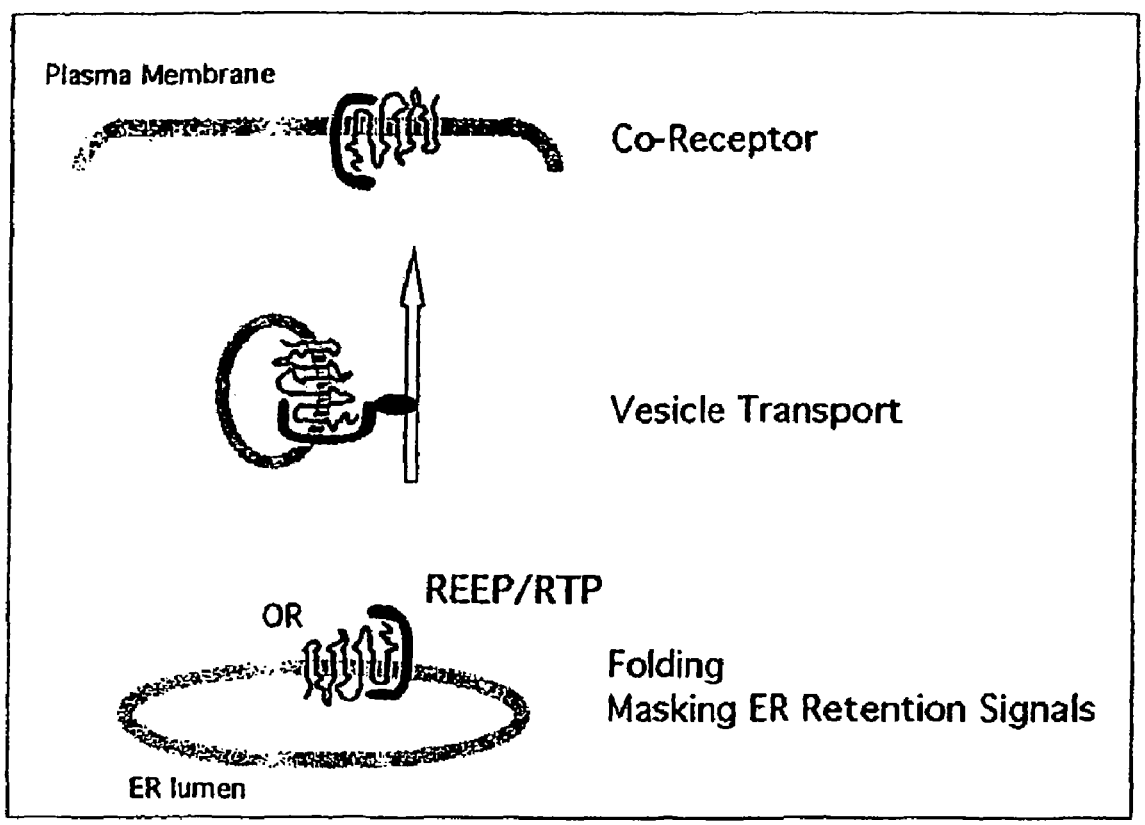

FIG. 13 shows models for the roles of REEP and/or RTP in odorant receptor expression.

FIG. 14 shows the nucleic acid (mRNA) sequence (SEQ ID NO: 1) and amino acid sequence (SEQ ID NO: 21) for murine REEP1.

FIG. 15 shows the nucleic acid (mRNA) sequence (SEQ ID NO: 2) and amino acid sequence (SEQ ID NO: 22) for murine REEP2.

FIG. 16 shows the nucleic acid (mRNA) sequence (SEQ ID NO: 3) and amino acid sequence (SEQ ID NO: 23) for murine REEP3.

FIG. 17 shows the nucleic acid (mRNA) sequence (SEQ ID NO: 4) and amino acid sequence (SEQ ID NO: 24) for murine REEP4.

FIG. 18 shows the nucleic acid (mRNA) sequence (SEQ ID NO: 5) and amino acid sequence (SEQ ID NO: 25) for murine REEP5.

FIG. 19 shows the nucleic acid (mRNA) sequence (SEQ ID NO: 6) and amino acid sequence (SEQ ID NO: 26) for murine REEP6.

FIG. 20 shows the nucleic acid (mRNA) sequence (SEQ ID NO: 7) and amino acid sequence (SEQ ID NO: 27) for human REEP1.

FIG. 21 shows the nucleic acid (mRNA) sequence (SEQ ID NO: 8) and amino acid sequence (SEQ ID NO: 28) for human REEP2.

FIG. 22 shows the nucleic acid (mRNA) sequence (SEQ ID NO: 9) and amino acid sequence (SEQ ID NO: 29) for human REEP3.

FIG. 23 shows the nucleic acid (mRNA) sequence (SEQ ID NO: 10) and amino acid sequence (SEQ ID NO: 30) for human REEP4.

FIG. 24 shows the nucleic acid (mRNA) sequence (SEQ ID NO: 11) and amino acid sequence (SEQ ID NO: 31) for human REEP5.

FIG. 25 shows the nucleic acid (mRNA) sequence (SEQ ID NO: 12) and amino acid sequence (SEQ ID NO: 32) for human REEP6.

FIG. 26 shows the nucleic acid (mRNA) sequence (SEQ ID NO: 13) and amino acid sequence (SEQ ID NO: 33) for murine RTP1.

FIG. 27 shows the nucleic acid (mRNA) sequence (SEQ ID NO: 14) and amino acid sequence (SEQ ID NO: 34) for murine RTP2.

FIG. 28 shows the nucleic acid (mRNA) sequence (SEQ ID NO: 15) and amino acid sequence (SEQ ID NO: 35) for murine RTP3.

FIG. 29 shows the nucleic acid (mRNA) sequence (SEQ ID NO: 16) and amino acid sequence (SEQ ID NO: 36) for murine RTP4.

FIG. 30 shows the nucleic acid (mRNA) sequence (SEQ ID NO: 17) for human RTP1-A1 and the amino acid sequence (SEQ ID NO: 37) for human RTP1.

FIG. 31 shows the nucleic acid (mRNA) sequence (SEQ ID NO: 18) and amino acid sequence (SEQ ID NO: 38) for human RTP2.

FIG. 32 shows the nucleic acid (mRNA) sequence (SEQ ID NO: 19) and amino acid sequence (SEQ ID NO: 39) for human RTP3.

FIG. 33 shows the nucleic acid (mRNA) sequence (SEQ ID NO: 20) and amino acid sequence (SEQ ID NO: 40) for human RTP4.

Figure 34:
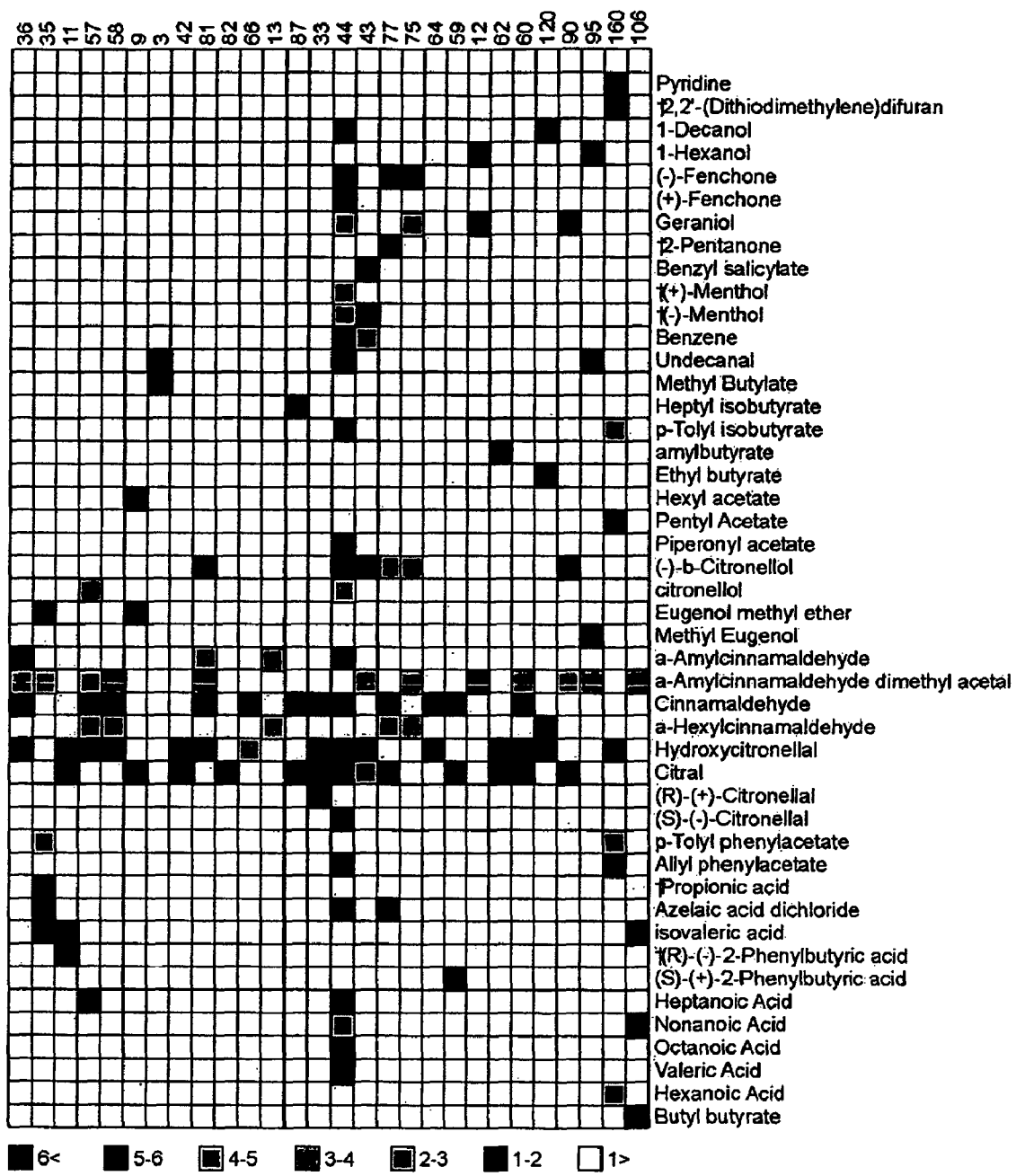

FIG. 34 shows the activation patterns of human odorant receptors in response to odiferous agent exposure.

FIG. 35 schematically shows amino acid segments of RTP1-A, RTP1-B, RTP1-C, RTP1-D, and RTP1-E in comparison to RTP1.

FIG. 36 shows the murine amino acid sequence for RTP1-A (SEQ ID NO: 41).

FIG. 37 shows the murine amino acid sequence for RTP1-B (SEQ ID NO: 42).

FIG. 38 shows the murine amino acid sequence for RTP1-C (SEQ ID NO: 43).

FIG. 39 shows the murine amino acid sequence for RTP1-D (SEQ ID NO: 44).

FIG. 40 shows the murine amino acid sequence for RTP1-E (SEQ ID NO: 45).

Figure 41:
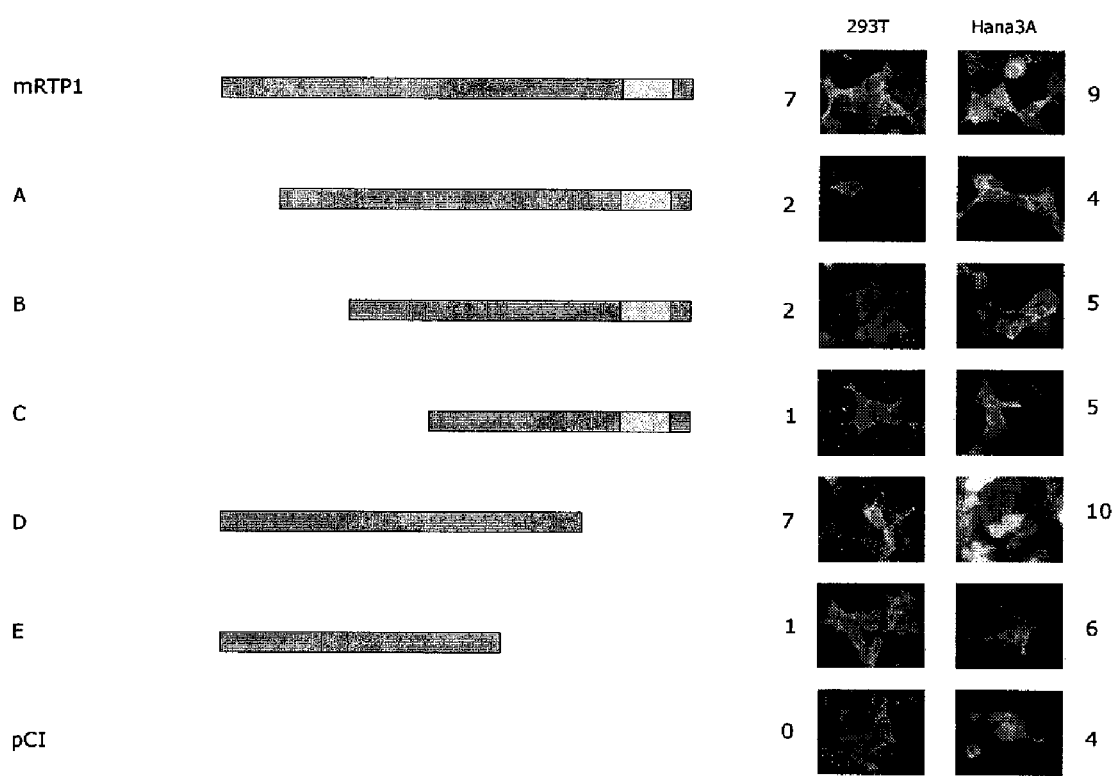

FIG. 41 shows cell-surface expression of OLFR62 in Hana3A and 293T cells. cDNAs encoding RTP1, RTP1-A, RTP1-B, RTP1-C, RTP1-D and RTP1-E were transfected into Hana3A cells or 293T cells. Increased cell-surface staining was seen in Hana3A cells and 239T cells expressing RTP1-D.

Figure 42:
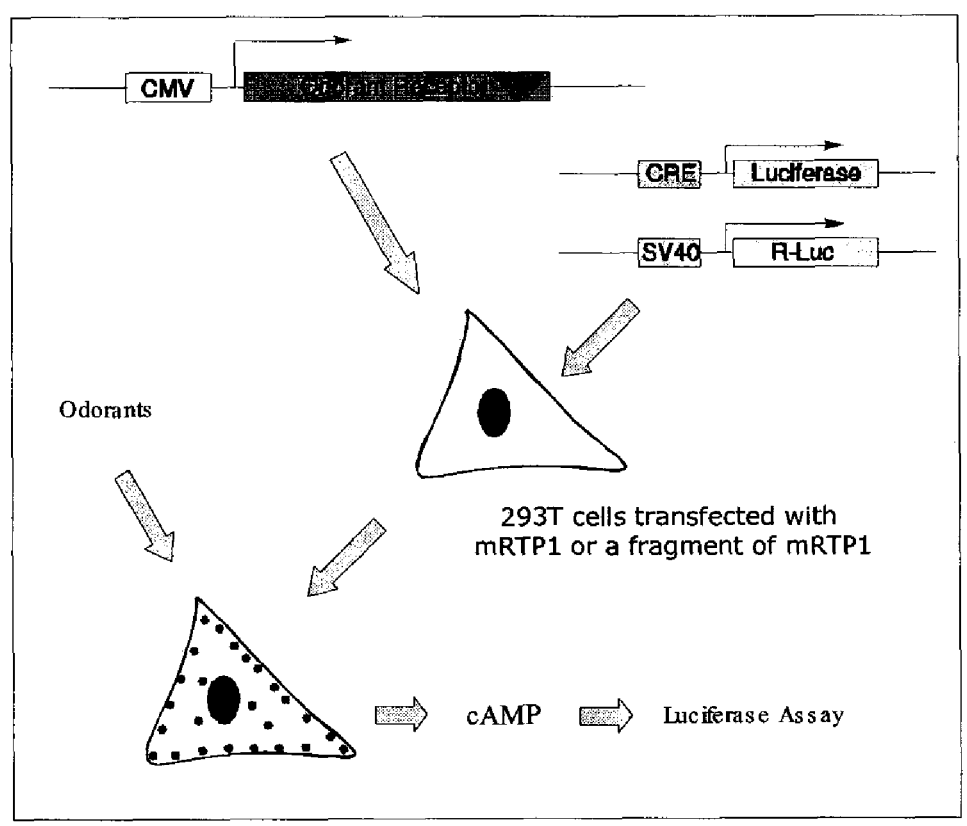

FIG. 42 schematically shows a luciferase assay used to monitor the activity of OLFR62 activity. cAMP responsive element (CRE) and luciferase was used to monitor activation of OLFR62. Activation of OLFR62 increases cAMP, which enhances the expression of luciferase reporter gene through the CRE.

Figure 43:
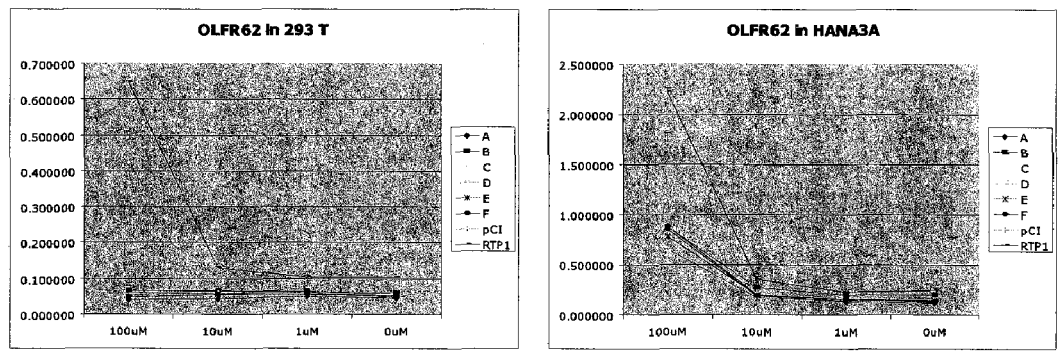

FIG. 43 shows OLFR62 activity as indicated by luciferase expression in Hana3A cells and 293T cells expressing RTP1, RTP1-A, RTP1-B, RTP1-C, RTP1-D, RTP1-E, and control pCI.

Figure 44:
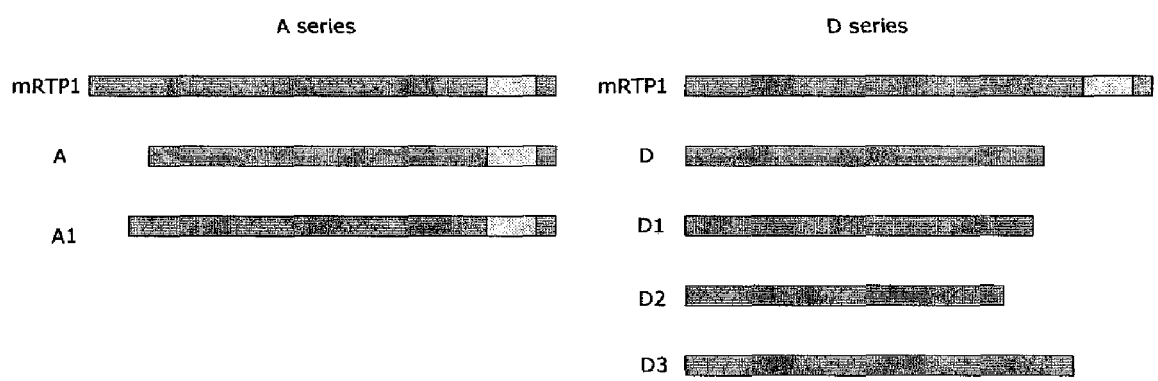

FIG. 44 schematically shows the amino acid segments of RTP1-A1, RTP1-D1, RTP1-D2, and RTP1-D3 in comparison to RTP1-A and RTP1-D, respectively.

FIG. 45 shows the murine amino acid sequence for RTP1-A1 (SEQ ID NO: 46), and the human amino acid sequence for RTP1-A1 (SEQ ID NO: 47).

FIG. 46 shows the murine amino acid sequence for RTP1-D1 (SEQ ID NO: 48).

FIG. 47 shows the murine amino acid sequence for RTP-D2 (SEQ ID NO: 49).

FIG. 48 shows the murine amino acid sequence for RTP-D3 (SEQ ID NO: 50).

Figure 49:
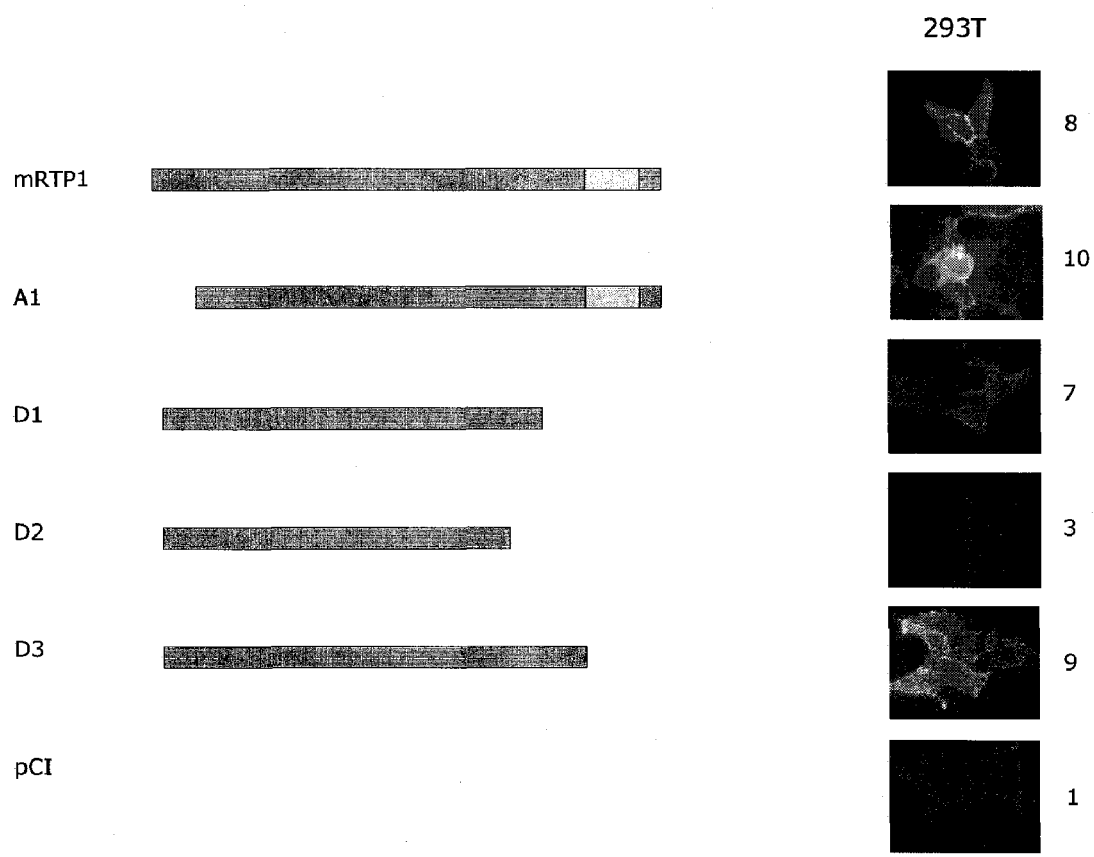

FIG. 49 shows cell-surface expression of OLFR62 in 293T cells. cDNAs encoding RTP1, RTP1-A1, RTP1-D1, RTP1-D2, and RTP1-D3, and control pCI were transfected into 293T cells. Increased cell-surface staining was seen in 239T cells expressing RTP1-A1, RTP1-D1 and RTP1-D3.

FIG. 50 shows OLFR62, OREG, S6, and 23-1 activity as indicated by luciferase expression in 293T cells expressing RTP1, RTP1-A1, RTP1-D1, RTP1-D2, and RTP1-D3, and control pCI.

Figure 51:
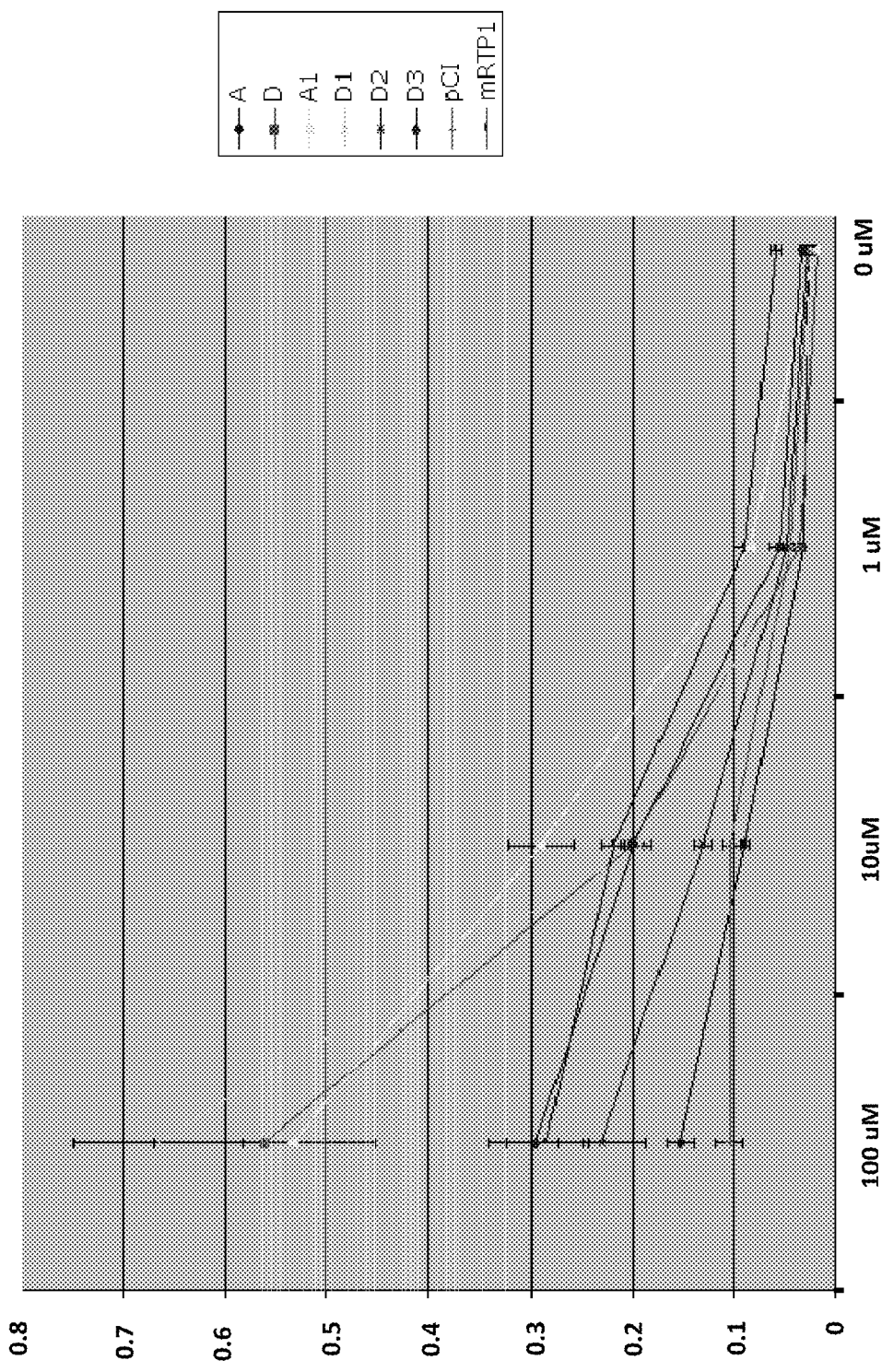
Figure 51:
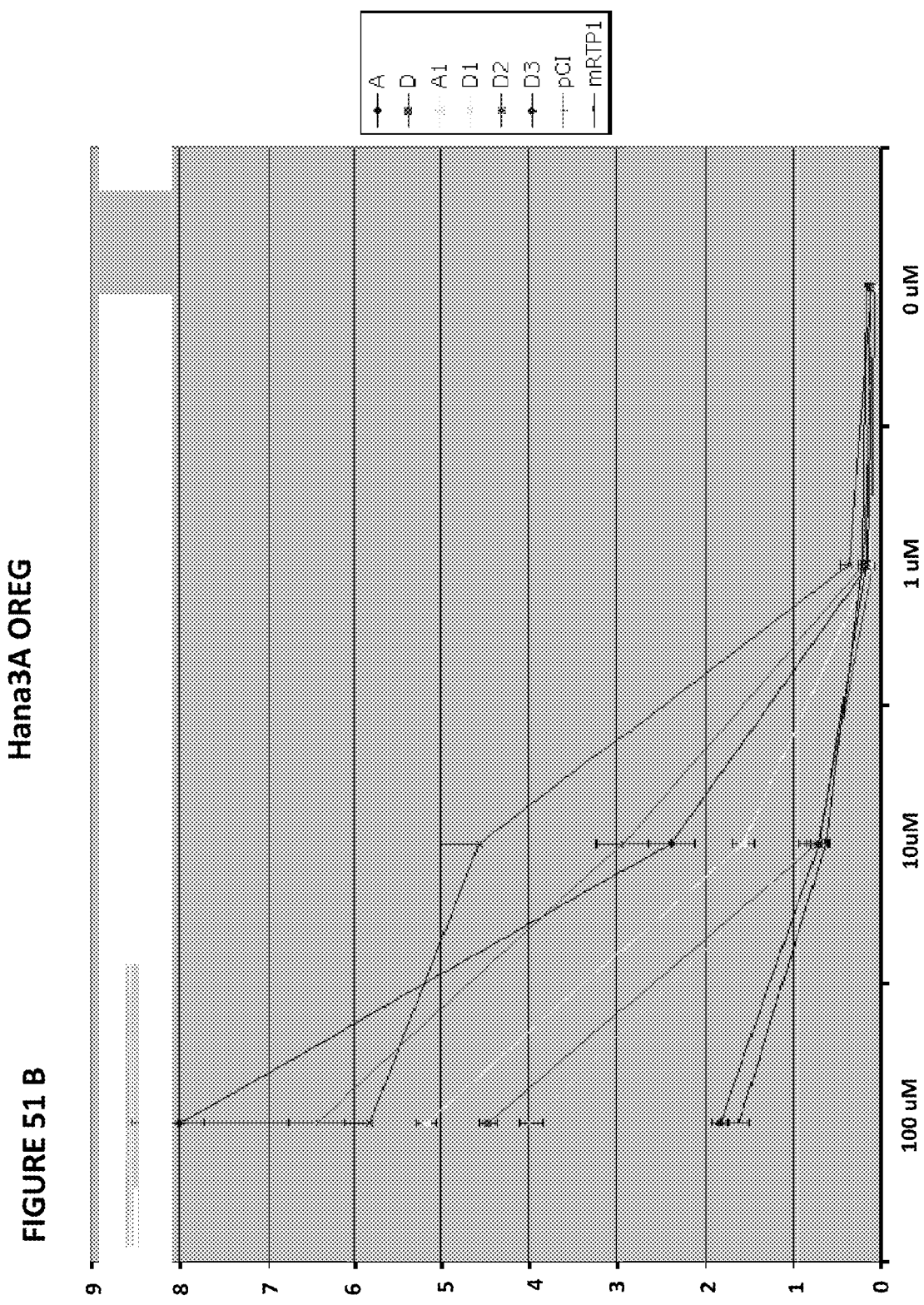
Figure 51:
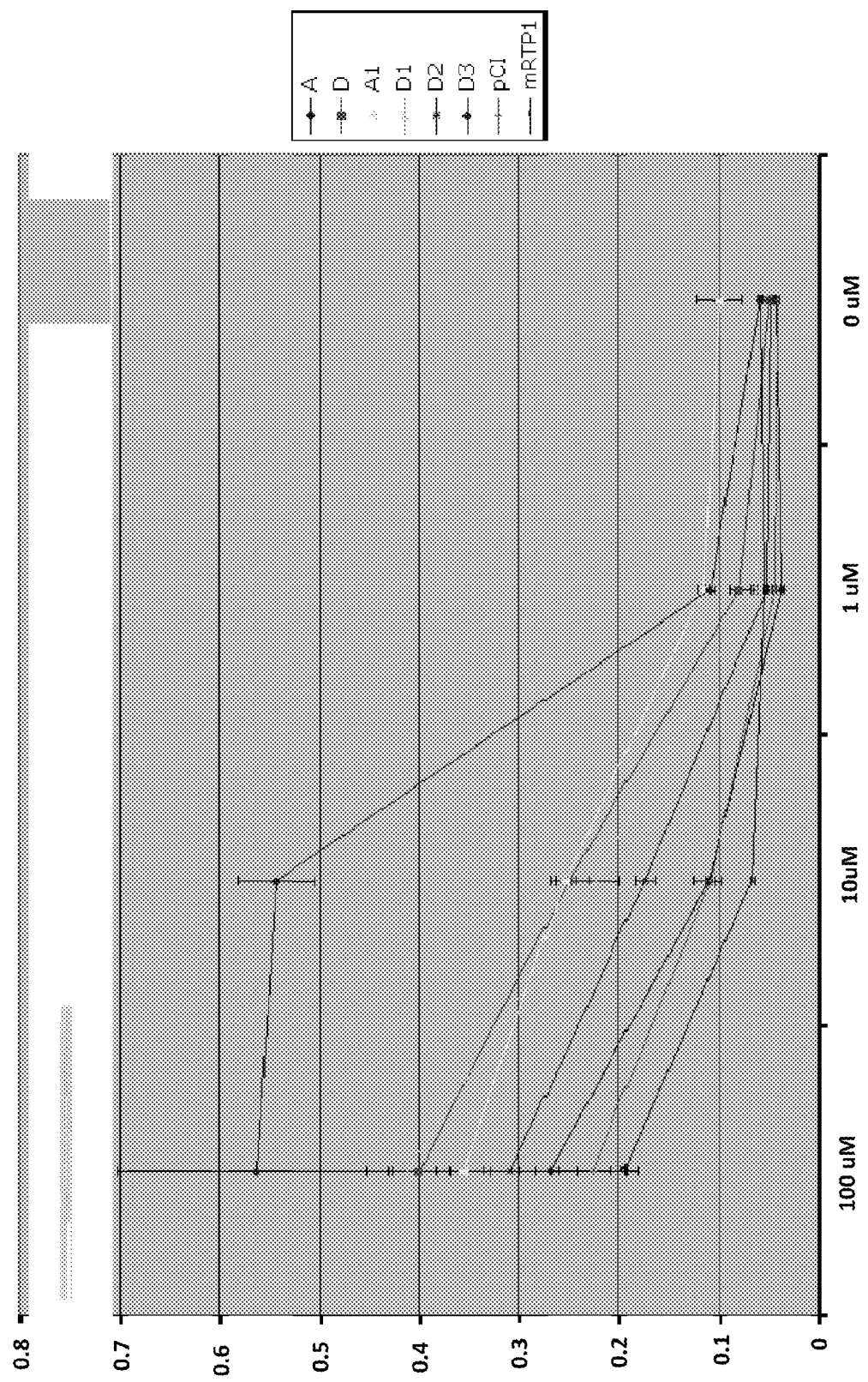
Figure 51:
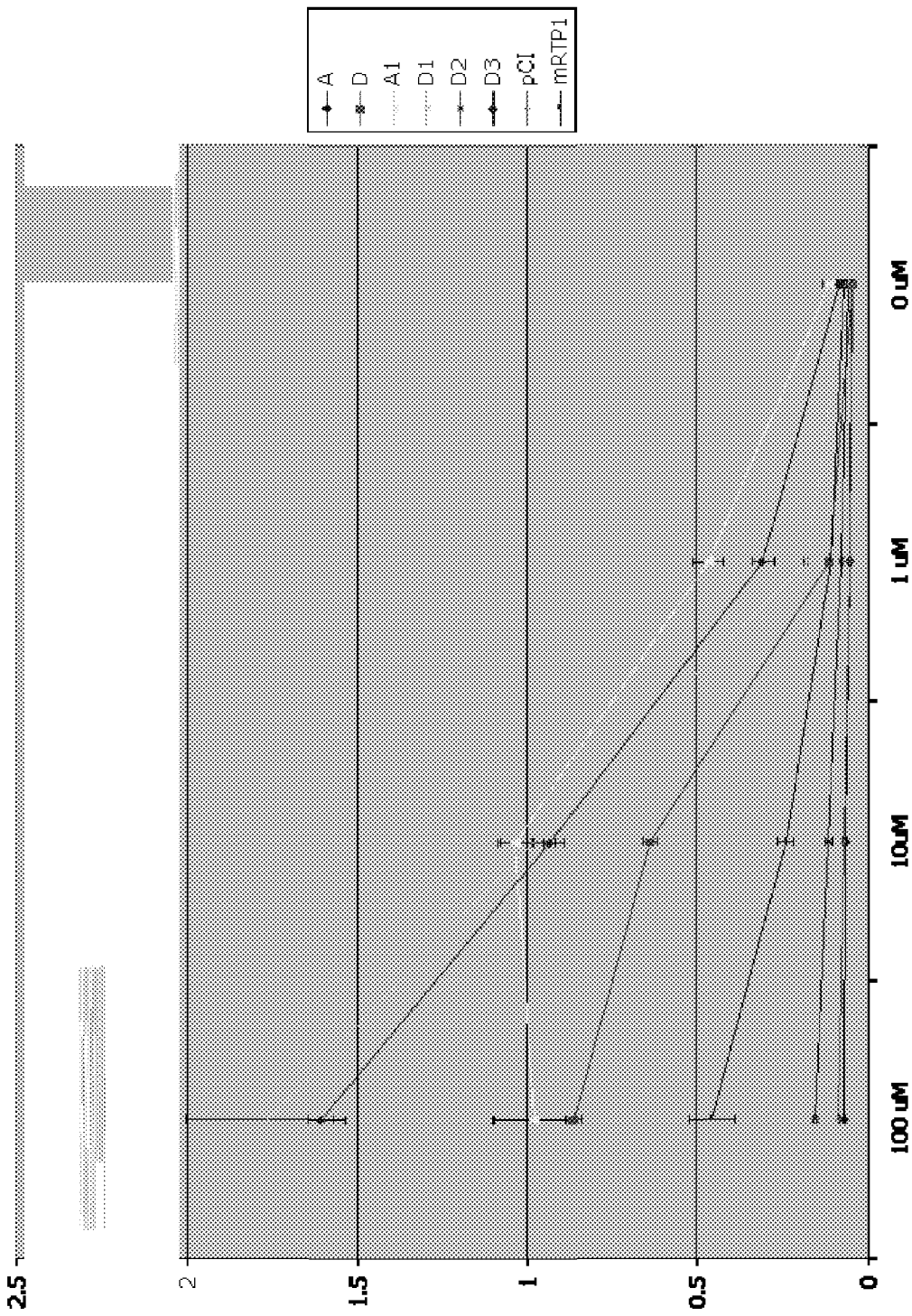

FIG. 51 shows OLFR62, OREG, S6, and 23-1 activity as indicated by luciferase expression in Hana3A cells expressing RTP1, RTP1-A1, RTP1-D1, RTP1-D2, and RTP1-D3, and control pCI.

Figure 52:
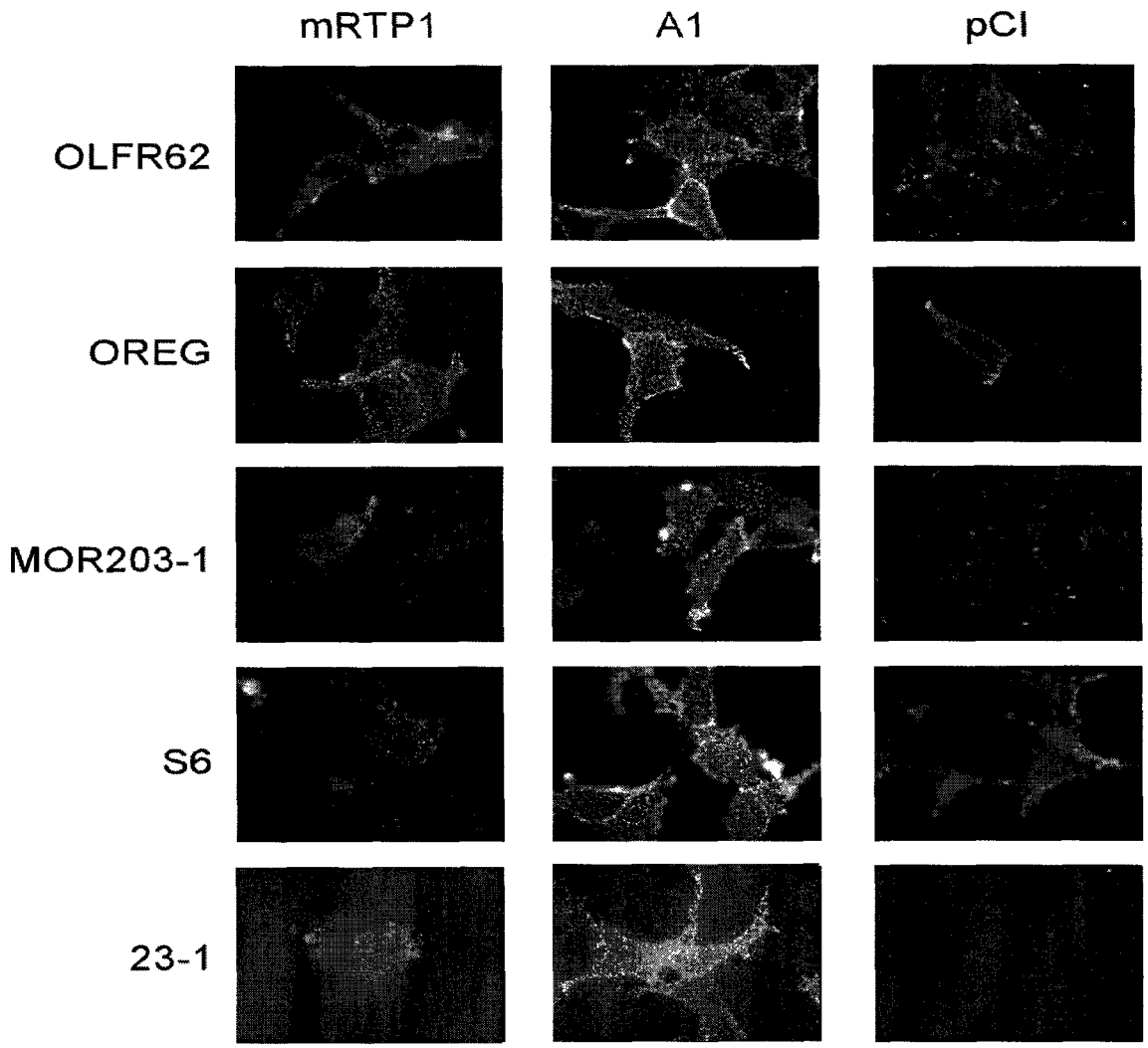

FIG. 52 shows cell-surface expression of OLFR62, OREG, MOR203-1, S6, and 23-1 in 293T cells co-transfected with either RTP1, RTP1-A1 or control pCI. cDNAs encoding RTP1, RTP1-A1, and control pCI were transfected into cells.

Figure 53:
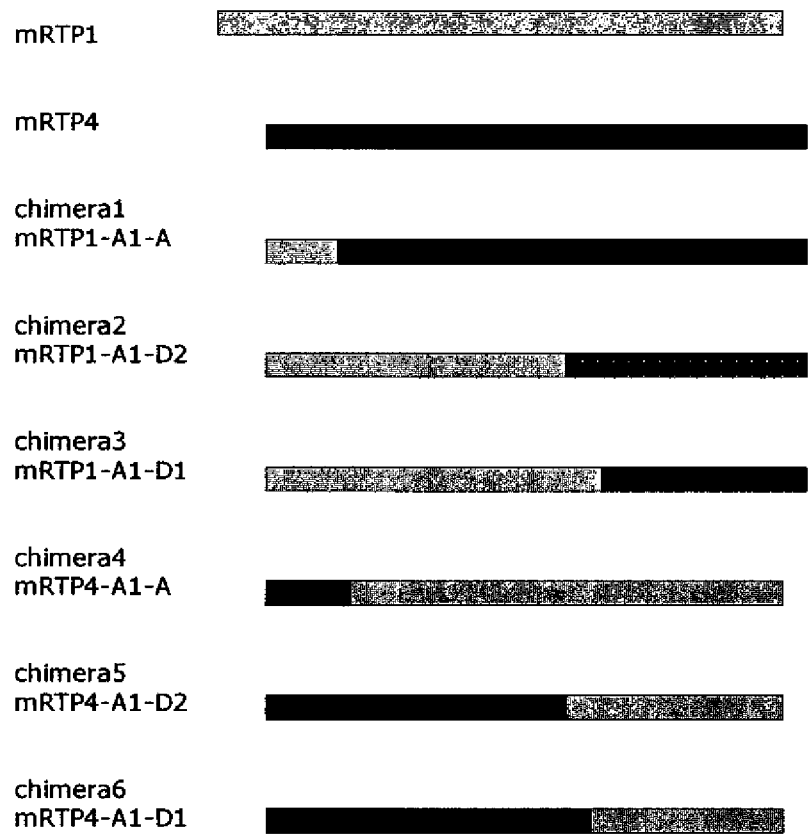

FIG. 53 schematically shows the amino acid segments of RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6).

Figure 54:
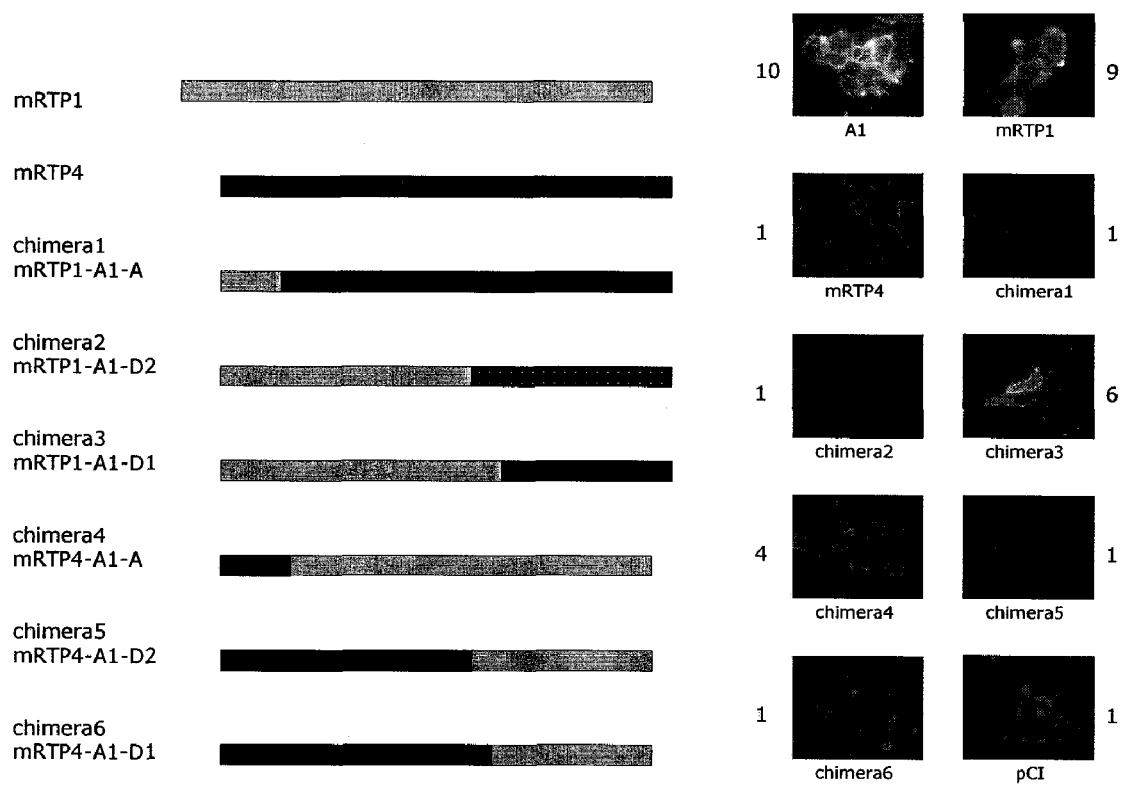

FIG. 54 shows cell-surface expression of an OR in cells expressing RTP1, RTP4, Chimera 1, Chimera 2, Chimera 3, Chimera 4, Chimera 5, Chimera 6, and control pCI. cDNAs encoding RTP1, RTP4, RTP1-A1, Chimera 1, Chimera 2, Chimera 3, Chimera 4, Chimera 5, Chimera 6, and control pCI were transfected into 293T cells.

Figure 55:
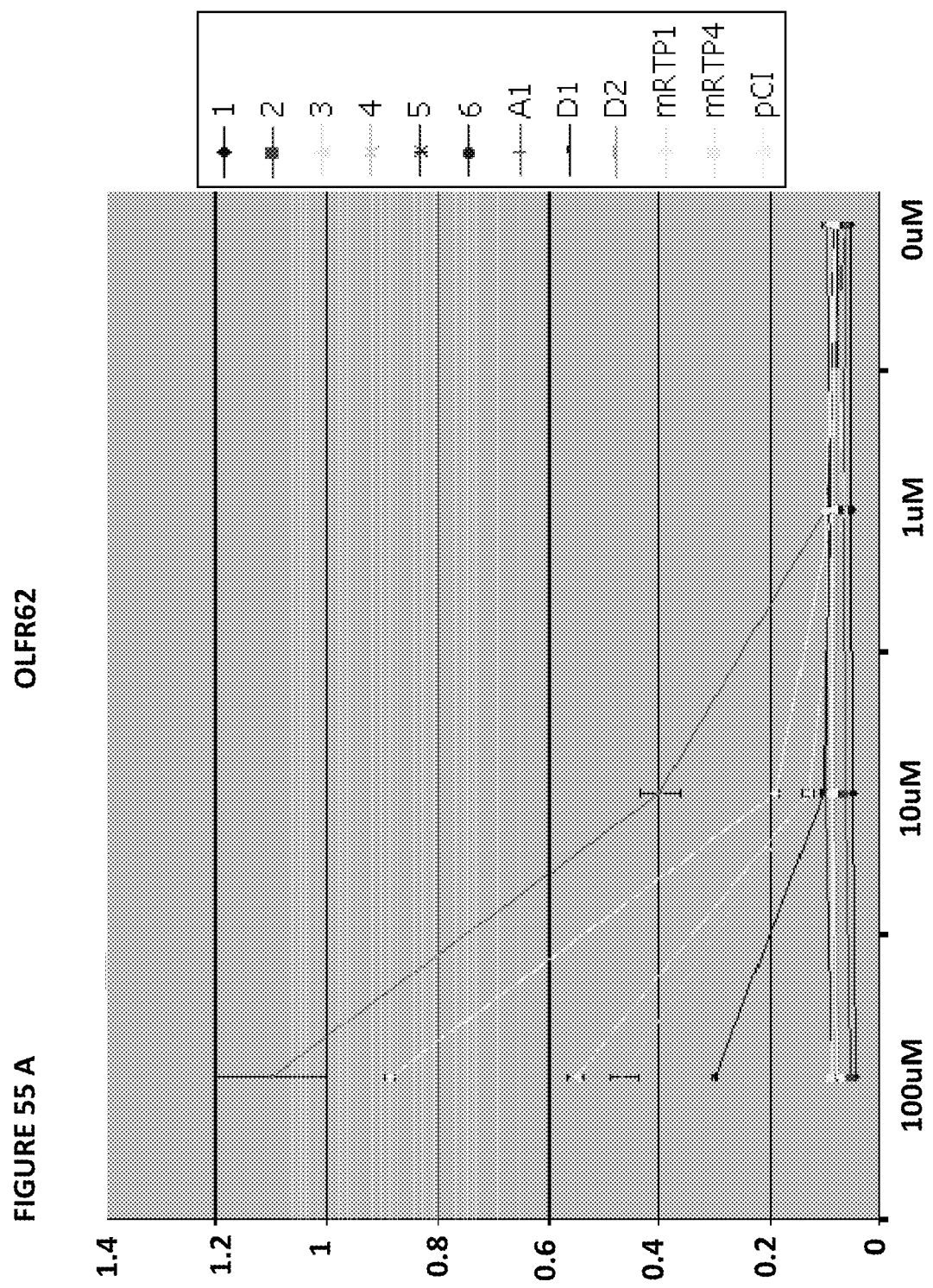
Figure 55:
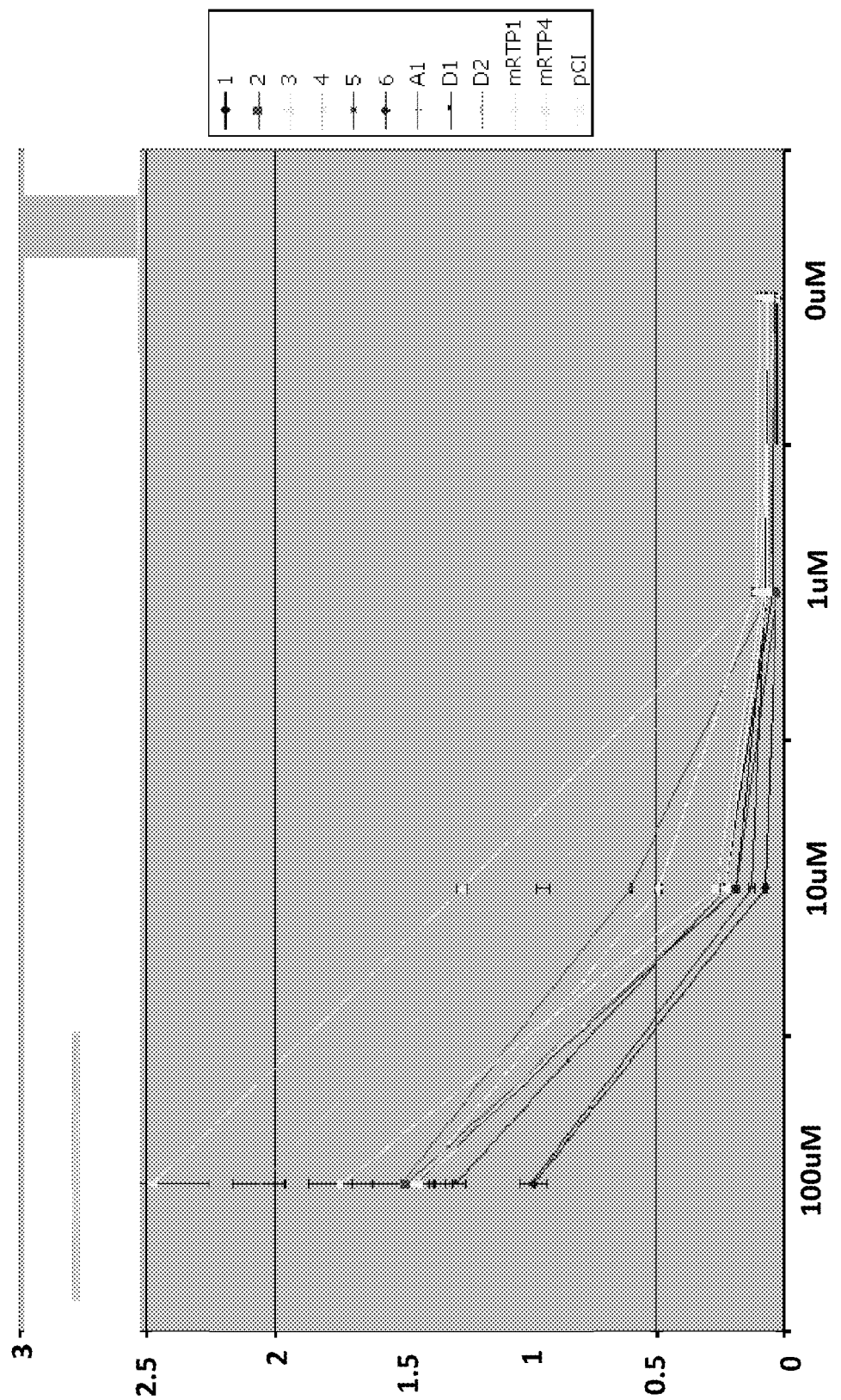
Figure 55:
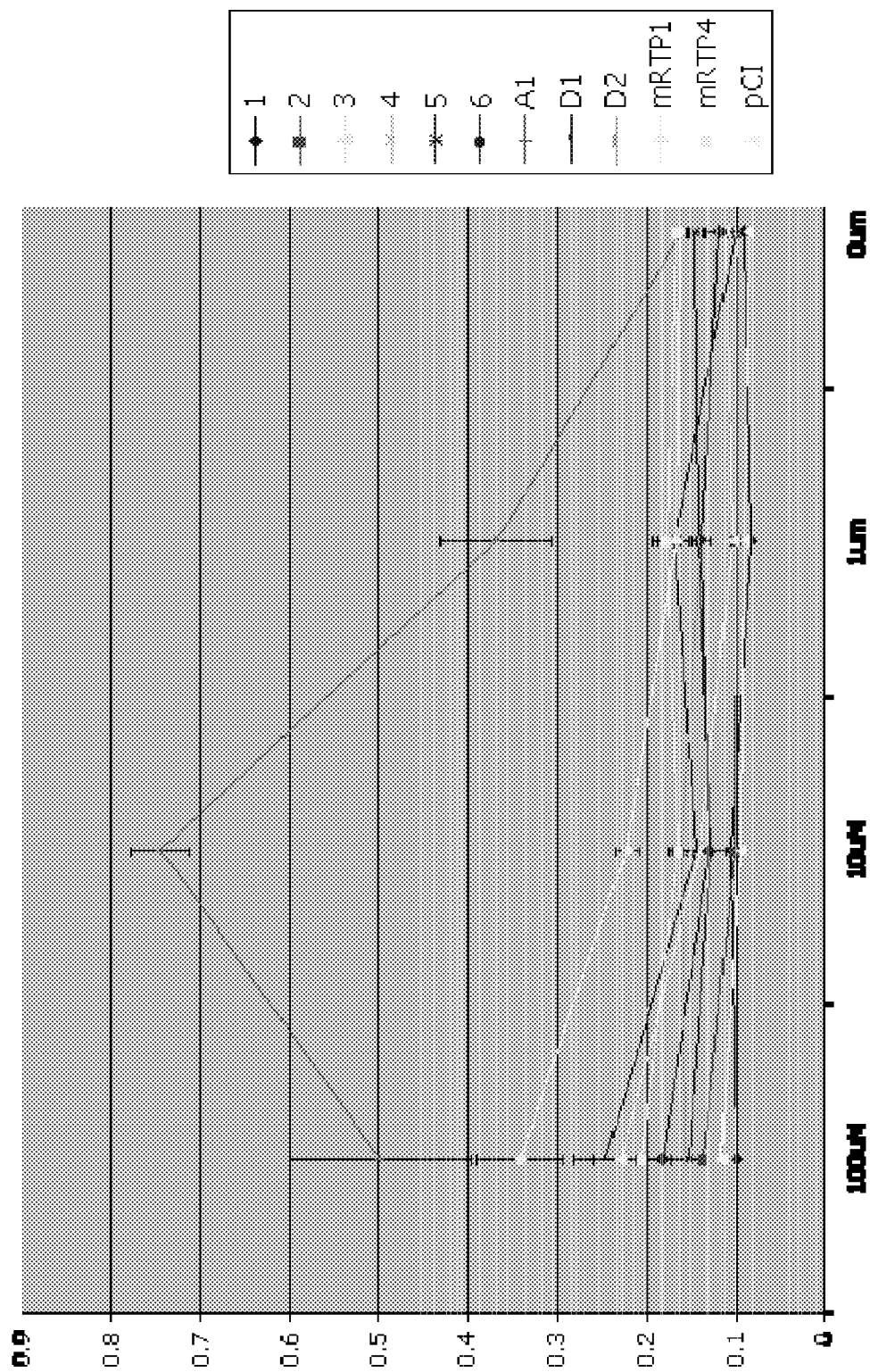
Figure 55:
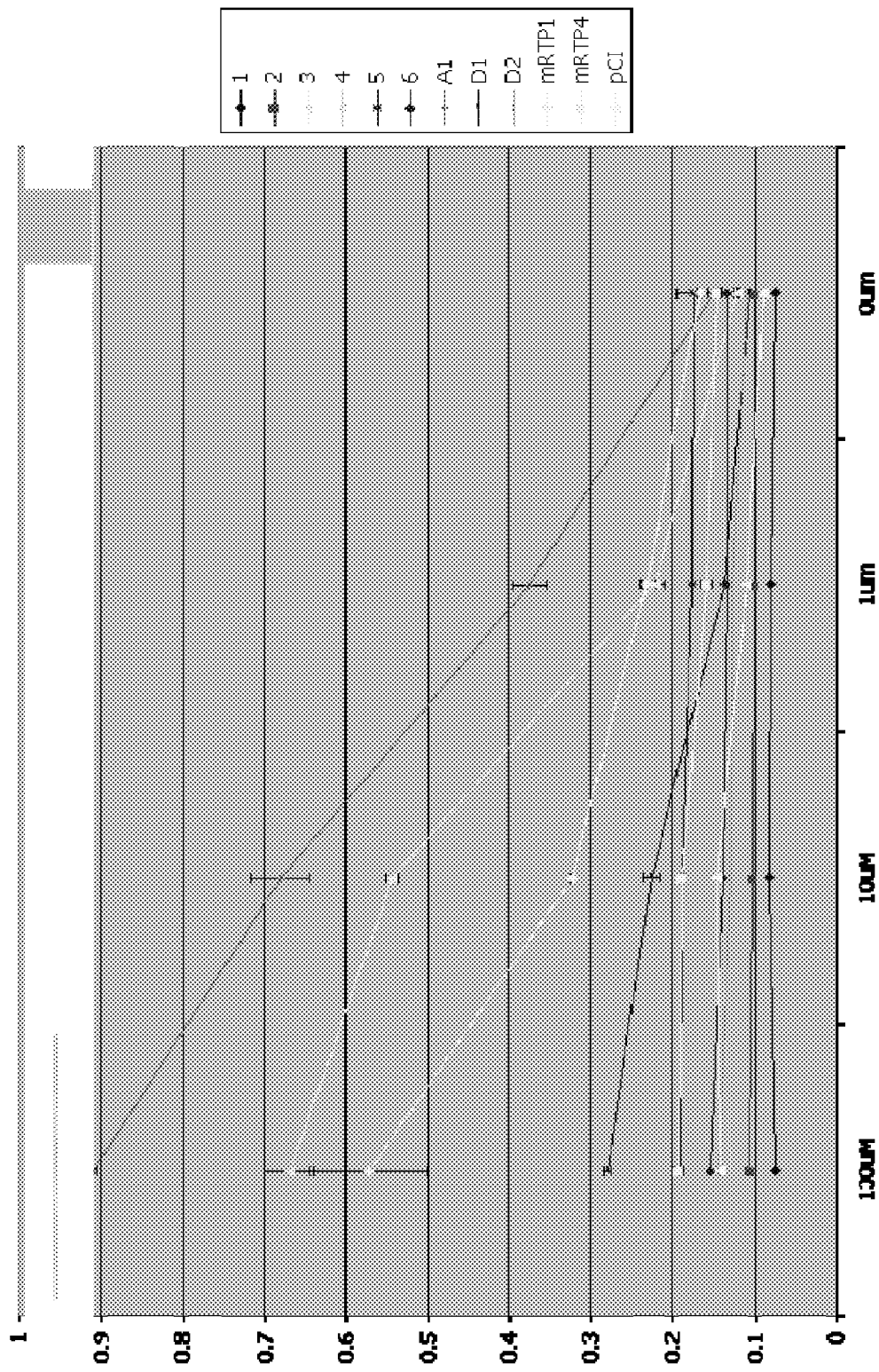

FIG. 55 shows OLFR62, OREG, S6, and 23-1 activity as indicated by luciferase expression in 293T cells expressing RTP1, RTP4, RTP1-A1, RTP1-D1, RTP1-D2, Chimera 1, Chimera 2, Chimera 3, Chimera 4, Chimera 5, Chimera 6, and control pCI.

Figure 56:
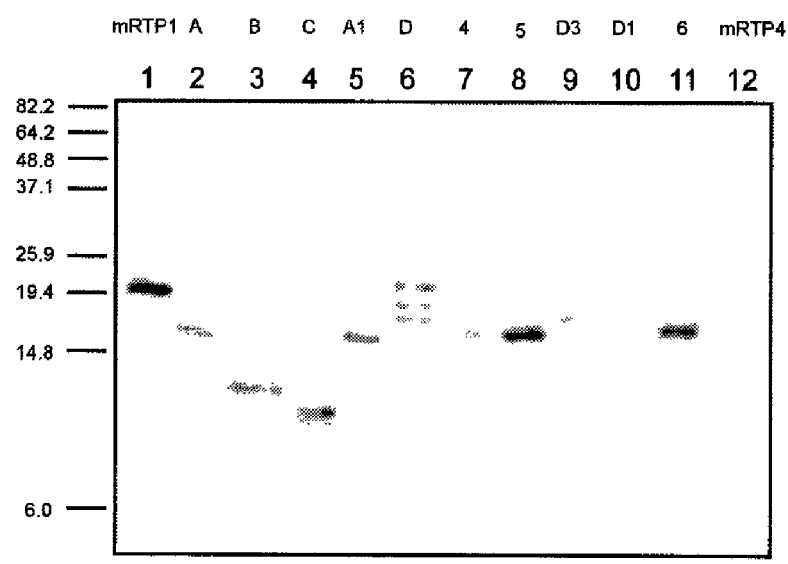

FIG. 56 shows detection of RTP1, RTP1-A, RTP1-B, RTP1-C, RTP1-A1, RTP1-D, Chimera 4, Chimera 5, RTP1-D3, RTP1-D1, Chimera 6, and RTP4 using anti-RTP1.

DEFINITIONS

To facilitate understanding of the invention, a number of terms are defined below.

As used herein, the term "REEP" when used in reference to proteins or nucleic acid refers to a REEP protein or nucleic acid encoding a REEP protein of the present invention. The term REEP encompasses both proteins that are identical to wild-type REEPs (e.g., REEP1, REEP2, REEP3, REEP4, REEP5, and REEP6) and those that are derived from wild-type REEP (e.g. variants of REEP polypeptides of the present invention). In some embodiments, the "REEP" is a wild type murine REEP nucleic acid (mRNA) (e.g., SEQ ID NOs: 1-6) or a polypeptide encoded by the wild type murine REEP amino acid sequence (e.g., SEQ ID NOs:21-26). In other embodiments, the "REEP" is a wild type human REEP nucleic acid (mRNA) (e.g., SEQ ID NOs: 7-12) or a polypeptide encoded by a wild type human REEP amino acid sequence (e.g., SEQ ID NOs: 27-32). Examples of REEP proteins or nucleic acids include, but are not limited to, REEP1, REEP2, REEP3, REEP4, REEP5 and REEP6.

As used herein, the term "RTP" when used in reference to proteins or nucleic acid refers to a RTP protein or nucleic acid encoding a RTP protein of the present invention. The term RTP encompasses both proteins that are identical to wild-type RTPs (e.g., RTP1, RTP2, RTP3, and RTP4) and those that are derived from wild-type RTP (e.g. variants of RTP polypeptides of the present invention including but not limited to RTP1-A, RTP1-B, RTP1-C, RTP1-D, RTP1-E, RTP1-A 1, RTP1-D1, RTP-D2, RTP-D3, or chimeric genes constructed with portions of RTP1 coding regions (e.g., RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)). In some embodiments, the "RTP" is a wild type murine RTP nucleic acid (mRNA) (e.g., SEQ ID NOs: 13-16) or a polypeptide encoded by the wild type or variant murine RTP amino acid sequence (e.g., SEQ ID NOs: 33-36, 41-50). In other embodiments, the "RTP" is a wild type human RTP nucleic acid (mRNA) (e.g., SEQ ID NO: 17 for RTP1-A1, and SEQ ID NOs: 18-20 for RTP2, RTP3, and RTP4) or a polypeptide encoded by a wild type human RTP amino acid sequence (e.g., SEQ ID NOs: 37-40). Examples of RTP proteins or nucleic acids include, but are not limited to, RTP1, RTP2, RTP3, RTP4, RTP1-A, RTP1-B, RTP1-C, RTP1-D, RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6).

As used herein, the term "odorant receptor" refers to odorant receptors generated from olfactory sensory neurons. Examples of odorant receptors include, but are not limited to, S6/79, S18, S46, S50, MOR23-1, MOR31-4, MOR31-6, MOR32-5 and MOR32-11.

As used herein, the term "odorant receptor cell surface localization" or equivalent terms refer to the molecular transport of an odorant receptor to a cell surface membrane. Examples of cell surface localization includes, but is not limited to, localization to cilia at the tip of a dendrite, and localization to an axon terminal.

As used herein, the term "odorant receptor functional expression" or equivalent terms, refer to an odorant receptor's ability to interact with an odorant receptor ligand (e.g., an odiferous molecule).

As used herein, the term "olfactory disorder," "olfactory dysfunction," "olfactory disease" or similar term refers to a disorder, dysfunction or disease resulting in a diminished olfactory sensation (e.g., smell aberration). Examples of olfactory disorders, dysfunctions and/or diseases include, but are not limited to, head trauma, upper respiratory infections, tumors of the anterior cranial fossa, Kallmann syndrome, Foster Kennedy syndrome, Parkinson's disease, Alzheimer's disease, Huntington chorea, and exposure to toxic chemicals or infections. Diminished olfactory sensation is classified as anosmia—absence of smell sensation; hyposmia—decreased smell sensation; dysosmia—distortion of smell sensation; cacosmia—sensation of a bad or foul smell; and parosmia—sensation of smell in the absence of appropriate stimulus.

As used herein, the term "REEP1" when used in reference to a protein or nucleic acid refers to a REEP1 protein or nucleic acid encoding a REEP1 protein of the present invention. The term REEP1 encompasses both proteins that are identical to wild-type REEP1 and those that are derived from wild type REEP1 (e.g., variants of REEP1 polypeptides of the present invention) or chimeric genes constructed with portions of REEP1 coding regions). In some embodiments, the "REEP1" is a wild type murine REEP1 nucleic acid (mRNA) (SEQ ID NO:1) or polypeptide encoded by the wild type murine amino acid sequence (SEQ ID NO: 21). In other embodiments, the "REEP1" is a wild type human REEP1 nucleic acid (mRNA) (SEQ ID NO: 7) or polypeptide encoded by the wild type human REEP1 amino acid sequence (SEQ ID NO: 27). In other embodiments, the "REEP1" is a variant or mutant nucleic acid or amino acid.

As used herein, the term "RTP1" when used in reference to a protein or nucleic acid refers to a RTP1 protein or nucleic acid encoding a RTP1 protein of the present invention. The term RTP1 encompasses both proteins that are identical to wild-type RTP1 and those that are derived from wild type RTP1 (e.g., variants of RTP1 polypeptides of the present invention including but not limited to RTP1-A, RTP1-B, RTP1-C, RTP1-D, RTP1-E, RTP1-A1, RTP1-D1, RTP-D2, RTP-D3) or chimeric genes constructed with portions of RTP1 coding regions (e.g., RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)). In some embodiments, the "RTP1" is a wild type murine RTP1 nucleic acid (mRNA) (SEQ ID NO: 13) or polypeptide encoded by the wild type murine amino acid sequence (SEQ ID NO: 33). In other embodiments, the "RTP1" is a wild type human RTP1 nucleic acid (mRNA) (SEQ ID NO: 17 for RTP1-A1) or polypeptide encoded by the wild type human RTP 1 amino acid sequence (SEQ ID NO: 37). In other embodiments, the "RTP1" is a variant or mutant nucleic acid or amino acid.

As used herein, the term "RTP2" when used in reference to a protein or nucleic acid refers to a RTP2 protein or nucleic acid encoding a RTP2 protein of the present invention. The term RTP2 encompasses both proteins that are identical to wild-type RTP2 and those that are derived from wild type RTP2 (e.g., variants of RTP2 polypeptides of the present invention) or chimeric genes constructed with portions of RTP2 coding regions). In some embodiments, the "RTP2" is a wild type murine RTP2 nucleic acid (mRNA) (SEQ ID NO:14) or polypeptide encoded by the wild type murine amino acid sequence (SEQ ID NO: 34). In other embodiments, the "RTP2" is a wild type human RTP2 nucleic acid (mRNA) (SEQ ID NO: 18) or polypeptide encoded by the wild type human REEP1 amino acid sequence (SEQ ID NO: 38). In other embodiments, the "RTP2" is a variant or mutant nucleic acid or amino acid.

As used herein, the terms "subject" and "patient" refer to any animal, such as a mammal like a dog, cat, bird, livestock, and preferably a human. Specific examples of "subjects" and "patients" include, but are not limited to, individuals with an olfactory disorder, and individuals with olfactory disorder-related characteristics or symptoms.

As used herein, the phrase "symptoms of an olfactory disorder" and "characteristics of an olfactory disorder" include, but are not limited to, a diminished olfactory sensation (e.g., smell aberration).

The phrase "under conditions such that the symptoms are reduced" refers to any degree of qualitative or quantitative reduction in detectable symptoms of olfactory disorders, including but not limited to, a detectable impact on the rate of recovery from disease, or the reduction of at least one symptom of an olfactory disorder.

The term "siRNAs" refers to short interfering RNAs. Methods for the use of siRNAs are described in U.S. Patent App. No.: 20030148519/A1 (herein incorporated by reference). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "instructions for using said kit for said detecting the presence or absence of a variant REEP1 nucleic acid or polypeptide in said biological sample," "instructions for using said kit for said detecting the presence or absence of a variant RTP1 nucleic acid or polypeptide in said biological sample," "instructions for using said kit for said detecting the presence or absence of a variant RTP2 nucleic acid or polypeptide in said biological sample" include instructions for using the reagents contained in the kit for the detection of variant and wild type REEP and/or RTP nucleic acids or polypeptides.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., REEP1, RTP1 or RTP2). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "REEP1 gene," "RTP1 gene," "RTP1 genes," "RTP2 gene," or "RTP2 genes" refer to the full-length respective REEP and/or RTP nucleotide sequence (e.g., contained in SEQ ID NOs:1, 2 and 3). However, it is also intended that the term encompass fragments of the REEP and/or RTP sequences (e.g., RTP1-A, RTP1-B, RTP1-C, RTP1-D, and RTP1-E, RTP1-A1, RTP1-D1, RTP-D2, RTP-D3), chimeric genes constructed with portions of RTP1 coding regions (e.g., RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)), mutants of the REEP and/or RTP sequences, as well as other domains within the full-length REEP and/or RTP nucleotide sequences. Furthermore, the terms "REEP1 nucleotide sequence," "REEP1 polynucleotide sequence," "RTP1 nucleotide sequence," "RTP1 polynucleotide sequence," "RTP2 nucleotide sequence," or "RTP2 polynucleotide sequence" encompasses DNA sequences, cDNA sequences, RNA (e.g., mRNA) sequences, and associated regulatory sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligo-nucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., REEP1, RTP1 or RTP2).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a REEP and/or RTP gene of the present invention).

As used herein, the term "detection assay" refers to an assay for detecting the presence or absence of variant nucleic acid sequences (e.g., polymorphisms or mutations) in a given allele of a particular gene (e.g., a REEP and/or RTP gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding REEP and/or RTP includes, by way of example, such nucleic acid in cells ordinarily expressing REEP and/or RTP where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, REEP and/or RTP antibodies are purified by removal of contaminating non-immunoglobulin proteins; they are also purified by the removal of immunoglobulin that does not bind a REEP and/or RTP polypeptide. The removal of non-immunoglobulin proteins and/or the removal of immunoglobulins that do not bind a REEP and/or RTP polypeptide results in an increase in the percent of REEP1, RTP1 or RTP2-reactive immunoglobulins in the sample. In another example, recombinant REEP and/or RTP polypeptides are expressed in bacterial host cells and the polypeptides are purified by the removal of host cell proteins; the percent of recombinant REEP and/or RTP polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding REEP1s, RTP1s or RTP2s (e.g., SEQ ID NOs:1, 2 and 3) or fragments thereof may be employed as hybridization probes. In this case, the REEP and/or RTP encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

GENERAL DESCRIPTION

Continued progress in understanding olfactory coding has been significantly hampered by the inability to functionally express ORs in heterologous cells in order to identify cognate ligands. To overcome this problem, experiments conducted during the course of the present invention searched for molecules that are included in cell-surface expression of ORs. Three transmembrane proteins, REEP1, RTP1, and RTP2, as well as variants thereof, were identified that promote functional cell surface expression of ORs in 293T cells. REEP and/or RTP are expressed specifically by olfactory neurons in the olfactory epithelium. REEP1 and RTP1 interacts with OR proteins. Using cells expressing REEP1 and RTP1 and RTP2, new ORs that respond to aliphatic odorants were identified. The present invention is not limited to a particular mechanism. Indeed, an understanding of the mechanism is not necessary to practice the present invention. Nonetheless, experiments conducted during the course of the present invention demonstrated the importance of the accessory proteins of ORs in functional cell-surface expression and in decoding OR-ligand specificities.

The identification and use of proteins involved in the localization of ORs provides numerous research, diagnostic, drug screening, and therapeutic applications. For example, the nucleic acids and proteins of the present invention permit the selective and controllable presentation of ORs on test cells to, among other things, identify new ORs, characterize ORs, identify OR ligands, correlate olfactory responses to the molecular interactions underlying such response, identify and characterize groups of ORs and ligands responsible for olfactory responses and health conditions, and identify, select, and characterize regulators of OR response to study and control olfactory responses. The present invention, also, thus provides means for manipulating olfactory responses and the molecular basis for such response in vitro and in vivo. Numerous commercial applications are thus made possible, including the production, characterization, and use of in vitro or in vivo cell arrays expressing desired localized ORs for screening (e.g., high-throughput screening) compounds or use as synthetic olfactory systems. Any industry, including food industries, health industries, cosmetic industries, militaries, sanitary agencies, animal sniffers (e.g., for drugs, explosives, accident victims, etc.), among many others will find use of the compositions and methods of the present invention.

Inhibitors (e.g., antibodies, small molecules, aptamers, etc.) of OR/ligand interactions that are identified by the methods of the present invention find may uses. For example, the present invention provides a systematic way to identify which receptors and ligands are responsible for particular olfactory sensations (e.g., perceived scents). Thus, for example, by blocking particular interactions (e.g., via a nasal spray having the inhibitors) or enhancing particular interactions (e.g., via a nasal spray that provides certain ligands or a coating on the surface of an object that emits certain ligands) one can control perceived scents. Thus, undesired scents can be blocked, covered, or altered (e.g., a sniffer dog can be treated so as to only smell a target of interested and no other distracting smells, a sanitary worked can be made immune to the scent of waste, etc.) and desired scents can be enhanced.

The present invention also provides novel gene and protein sequences and methods of their use. A detailed description of certain preferred embodiments and uses of the present invention is described below. The present invention is not limited to these particular illustrative embodiments.

DETAILED DESCRIPTION OF THE INVENTION

The present invention relates to peptides capable of promoting odorant receptor cell-surface localization and odorant receptor functional expression. The present invention further provides assays for the detection of therapeutic agents, and for the detection of odorant receptor accessory protein polymorphisms and mutations associated with disease states. Exemplary embodiments of the present invention are described below.

Exemplary compositions and methods of the present invention are described in more detail in the following sections: I. Olfactory Sensation; II. REEP and RTP Polynucleotides; III. REEP and RTP Polypeptides; IV. Detection of REEP and RTP Alleles; V. Generation of REEP and RTP Antibodies; VI. Gene Therapy Using REEP and RTP; VII. Transgenic Animals Expressing Exogenous REEP and RTP Genes and Homologs, Mutants, and Variants Thereof, VIII. Drug Screening Using REEP and RTP; IX. Pharmaceutical Compositions Containing REEP and RTP Nucleic Acid, Peptides, and Analogs; X. RNA Interference (RNAi); XI. RNAi for REEP and RTP; and XII. Identification of Odorant Receptor Ligands.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Olfactory Sensation

The olfactory system represents one of the oldest sensory modalities in the phylogenetic history of mammals. Olfaction is less developed in humans than in other mammals such as rodents. As a chemical sensor, the olfactory system detects food and influences social and sexual behavior. The specialized olfactory epithelial cells characterize the only group of neurons capable of regeneration. Activation occurs when odiferous molecules come in contact with specialized processes known as the olfactory vesicles. Within the nasal cavity, the turbinates or nasal conchae serve to direct the inspired air toward the olfactory epithelium in the upper posterior region. This area (only a few centimeters wide) contains more than 100 million olfactory receptor cells. These specialized epithelial cells give rise to the olfactory vesicles containing kinocilia, which serve as sites of stimulus transduction.

There are three specialized neural systems are present within the nasal cavities in humans: 1) the main olfactory system (cranial nerve I), 2) trigeminal somatosensory system (cranial nerve V), 3) the nervus terminalis (cranial nerve 0). CN I mediates odor sensation. It is responsible for determining flavors. CN V mediates somatosensory sensations, including burning, cooling, irritation, and tickling. CN 0 is a ganglionated neural plexus. It spans much of the nasal mucosa before coursing through the cribriform plate to enter the forebrain medial to the olfactory tract. The exact function of the nervus terminalis is unknown in humans.

The olfactory neuroepithelium is a pseudostratified columnar epithelium. The specialized olfactory epithelial cells are the only group of neurons capable of regeneration. The olfactory epithelium is situated in the superior aspect of each nostril, including cribriform plate, superior turbinate, superior septum, and sections of the middle turbinate. It harbors sensory receptors of the main olfactory system and some CN V free nerve endings. The olfactory epithelium loses its general homogeneity postnatally, and as early as the first few weeks of life metaplastic islands of respiratory-like epithelium appear. The metaplasia increases in extent throughout life. It is presumed that this process is the result of insults from the environment, such as viruses, bacteria, and toxins.

There are 6 distinct cells types in the olfactory neuroepithelium: 1) bipolar sensory receptor neurons, 2) microvillar cells, 3) supporting cells, 4) globose basal cells, 5) horizontal basal cells, 6) cells lining the Bowman's glands. There are approximately 6,000,000 bipolar neurons in the adult olfactory neuroepithelium. They are thin dendritic cells with rods containing cilia at one end and long central processes at the other end forming olfactory fila. The olfactory receptors are located on the ciliated dendritic ends. The unmyelinated axons coalesce into 40 bundles, termed olfactory fila, which are ensheathed by Schwann-like cells. The fila transverses the cribriform plate to enter the anterior cranial fossa and constitute CN I. Microvillar cells are near the surface of the neuroepithelium, but the exact functions of these cells are unknown. Supporting cells are also at the surface of the epithelium. They join tightly with neurons and microvillar cells. They also project microvilli into the mucus. Their functions include insulating receptor cells from one another, regulating the composition of the mucus, deactivating odorants, and protecting the epithelium from foreign agents. The basal cells are located near the basement membrane, and are the progenitor cells from which the other cell types arise. The Bowman's glands are a major source of mucus within the region of the olfactory epithelium.

The odorant receptors are located on the cilia of the receptor cells. Each receptor cell expresses a single odorant receptor gene. There are approximately 1,000 classes of receptors at present. The olfactory receptors are linked to the stimulatory guanine nucleotide binding protein Golf. When stimulated, it can activate adenylate cyclase to produce the second messenger cAMP, and subsequent events lead to depolarization of the cell membrane and signal propagation. Although each receptor cell only expresses one type of receptor, each cell is electrophysiologically responsive to a wide but circumscribed range of stimuli. This implies that a single receptor accepts a range of molecular entities.

The olfactory bulb is located on top of the cribriform plate at the base of the frontal lobe in the anterior cranial fossa. It receives thousands of primary axons from olfactory receptor neurons. Within the olfactory bulb, these axons synapse with a much smaller number of second order neurons which form the olfactory tract and project to olfactory cortex. The olfactory cortex includes the frontal and temporal lobes, thalamus, and hypothalamus.

Although mammalian ORs were identified over 10 years ago, little is known about the selectivity of the different ORs for chemical stimuli, mainly because it has been difficult to express ORs on the cell surface of heterologous cells and assay their ligand-binding specificity (see, e.g., Mombaerts, P. (2004) Nat Rev Neurosci 5, 263-278; herein incorporated by reference in its entirety). The reason is that OR proteins are retained in the ER and subsequently degraded in the proteosome (see, e.g., Lu, M., et al., (2003) Traffic 4, 416-433; McClintock, T. S., (1997) Brain Res Mol Brain Res 48, 270-278; each herein incorporated by reference in their entireties). Despite these difficulties, extensive efforts have matched about 20 ORs with cognate ligands with various degrees of certainty (see, e.g., Bozza, T., et al., (2002) J Neurosci 22, 3033-3043; Gaillard, I., et al., (2002) Eur J Neurosci 15, 409-418; Hatt, H., et al., (1999) Cell Mol Biol 45, 285-291; Kajiya, K., et al., (2001) J Neurosci 21, 6018-6025; Krautwurst, D., et al., (1998) Cell 95, 917-926; Malnic, B., et al., (1999) Cell 96, 713-723; Raming, K., et al., (1993) Nature 361, 353-356; Spehr, M., et al., (2003) Science 299, 2054-2058; Touhara, K., et al., (1999) Proc Natl Acad Sci USA 96, 4040-4045; Zhao, H., et al., (1998) Science 279, 237-242; each herein incorporated by reference in their entirety). Adding the 20 N-terminal amino acids of rhodopsin (e.g., Rho-tag) or a foreign signal peptide to the N-terminus facilitates surface expression of some ORs in heterologous cells (see, e.g., Hatt, H., et al., (1999) Cell Mol Biol 45, 285-291; Krautwurst, D., et al., (1998) Cell 95, 917-926; each herein incorporated in their entirety). However, for most ORs, modifications do not reliably promote cell-surface expression. For example, ODR-4, which is required for proper localization of chemosensory receptors in *C. elegans*, has a small effect on facilitating cell-surface expression of one rat OR, but not another OR (see, e.g., Gimelbrant, A. A., et al., (2001) J Biol Chem 276, 7285-7290; herein incorporated by reference). These findings indicate that olfactory neurons have a selective molecular machinery that promotes proper targeting of OR proteins to the cell surface, but no components of this machinery have been identified (see, e.g., Gimelbrant, A. A., et al., (2001) J Biol Chem 276, 7285-7290; McClintock, T. S., and Sammeta, N. (2003) Neuroreport 14, 1547-1552; each herein incorporated by reference in their entirety).

For some GPCRs, accessory proteins are required for correct targeting to the cell surface membrane (see, e.g., Brady, A. E., and Limbird, L. E. (2002) Cell Signal 14, 297-309; herein incorporated by reference in its entirety). These proteins include NinaA for *Drosophila* Rhodopsin (see, e.g., Baker, E. K., et al., (1994) Embo J 13, 4886-4895; Shieh, B. H., et al., (1989) Nature 338, 67-70; each herein incorporated by reference in their entirety), RanBP2 for mammalian cone opsin (see, e.g., Ferreira, P. A., et al., (1996) Nature 383, 637-640; herein incorporated by reference in its entirety), RAMPs for the mammalian calcitonin receptor-like receptor (CRLR) (see, e.g., McLatchie, L. M., et al., (1998) Nature 393, 333-339; herein incorporated by reference in its entirety) and finally the M10 family of MHC class I proteins and beta 2 microglobulin for V2Rs, the putative mammalian pheromone receptors (see, e.g., Loconto, J., et al., (2003) Cell 112, 607-618; herein incorporated by reference in its entirety). With the exception of NinaA and RanBP2, none of these accessory proteins share any sequence homology to with each other; their only common feature is their association with the membrane.

The present invention provides novel proteins (e.g., REEP1, RTP1, RTP2, RTP1-A, RTP1-B, RTP1-C, RTP1-D, RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)) promoting OR cell surface localization and OR functional expression, and numerous compositions and methods related to these findings.

II. REEP and RTP Polynucleotides

As described above, the present invention provides novel proteins promoting odorant receptor cell surface localization and odorant receptor functional expression. In particular, the present invention provides REEP genes and polypeptides (e.g., REEP1, REEP2, REEP3, REEP4, REEP5, and REEP6) and RTP genes and polypeptides (e.g., RTP1, RTP2, RTP3, RTP4, RTP1-A, RTP1-B, RTP1-C, RTP1-D, RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)). In preferred embodiments, REEP1, RTP1, RTP2, and variants of RTP1 (e.g., RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6) promote odorant receptor cell surface localization and odorant receptor functional expression.

Accordingly, the present invention provides nucleic acids encoding REEP genes, homologs, variants (e.g., polymorphisms and mutants), including but not limited to, those described in SEQ ID NOs:1-12. The present invention provides nucleic acids encoding RTP genes, homologs, variants (e.g., polymorphisms and mutants), including but not limited to, those described in SEQ ID NOs:13-20. Table 1 describes exemplary REEP and RTP genes of the present invention. In some embodiments, the present invention provides polynucleotide sequences that are capable of hybridizing to SEQ ID NOs: 1-20 under conditions of low to high stringency as long as the polynucleotide sequence capable of hybridizing encodes a protein that retains a biological activity of the naturally occurring REEP and/or RTP protein. In some embodiments, the protein that retains a biological activity of a naturally occurring REEP and/or RTP is 70% homologous to the wild-type REEP and/or RTP, preferably 80% homologous to the wild-type REEP and/or RTP, more preferably 90% homologous to the wild-type REEP and/or RTP, and most preferably 95% homologous to wild-type the REEP and/or RTP. In preferred embodiments, hybridization conditions are based on the melting temperature ($T_m$) of the nucleic acid binding complex and confer a defined "stringency" as explained above (see e.g., Wahl, et al., Meth. Enzymol., 152: 399-407 (1987), incorporated herein by reference).

In other embodiments of the present invention, additional alleles of REEP and/or RTP genes are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Additional examples include truncation mutations (e.g., such that the encoded mRNA does not produce a complete protein).

In still other embodiments of the present invention, the nucleotide sequences of the present invention may be engineered in order to alter a REEP and/or RTP coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.). Variants of RTP1 include but are not limited to RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6).

In some embodiments of the present invention, the polynucleotide sequence of REEP and/or RTP may be extended utilizing the nucleotide sequence in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 (1993); herein incorporated by reference in its entirety). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed REEP and/or RTP sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., REEP and/or RTP function) for such purposes as altering the biological activity (e.g., altered REEP and/or RTP function). Such modified peptides are considered functional equivalents of peptides having an activity of a REEP and/or RTP peptide as defined herein. A modified peptide can be produced in which the nucleotide sequence encoding the polypeptide has been altered, such as by substitution, deletion, or addition. In particularly preferred embodiments, these modifications do not significantly reduce the biological activity of the modified REEP and/or RTP genes. In other words, construct "X" can be evaluated in order to determine whether it is a member of the genus of modified or variant REEP and/or RTP of the present invention as defined functionally, rather than structurally. In preferred embodiments, the activity of variant REEP and/or RTP polypeptides is evaluated by methods described herein (e.g., the generation of transgenic animals or the use of signaling assays).

Moreover, as described above, variant forms of REEP and/or RTP genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of REEP and/or RTP containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a REEP and/or RTP coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

Variants of RTP1 include but are not limited to RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6).

TABLE 1

OR Modulator Genes

| Gene | SEQ ID NO (Nucleic acid) | SEQ ID NO (Polypeptide) |
| --- | --- | --- |
| Murine REEP1 | 1 | 21 |
| Murine REEP2 | 2 | 22 |
| Murine REEP3 | 3 | 23 |
| Murine REEP4 | 4 | 24 |
| Murine REEP5 | 5 | 25 |
| Murine REEP6 | 6 | 26 |
| Human REEP1 | 7 | 27 |
| Human REEP2 | 8 | 28 |
| Human REEP3 | 9 | 29 |
| Human REEP4 | 10 | 30 |
| Human REEP5 | 11 | 31 |
| Human REEP6 | 12 | 32 |
| Murine RTP1 | 13 | 33 |
| Murine RTP2 | 14 | 34 |
| Murine RTP3 | 15 | 35 |
| Murine RTP4 | 16 | 36 |
| Human RTP1 | 17 | 37 |
|  | (for RTP1-A1) |  |
| Human RTP2 | 18 | 38 |
| Human RTP3 | 19 | 39 |
| Human RTP4 | 20 | 40 |

III. REEP and RTP Polypeptides

In other embodiments, the present invention provides REEP and/or RTP polynucleotide sequences that encode REEP and/or RTP polypeptide sequences (e.g., the polypeptides of SEQ ID NOs: 21-40, 41-50 respectively). In preferred embodiments, the present invention provides a polypeptide encoded by a nucleic acid selected from the group consisting of SEQ ID NOs: 1, 7, 13, 14, 17 and 18 and variants thereof that are at least 80% identical to SEQ ID NOs: 1, 7, 13, 14, 17 and 18. In further embodiments, the protein is at least 90% identical to SEQ ID NOs: 1, 7, 13, 14, 17 and 18. In even further embodiments, the protein is at least 95% identical to SEQ ID NOs: 1, 7, 13, 14, 17 and 18. Other embodiments of the present invention provide fragments, fusion proteins or functional equivalents of REEP and/or RTP proteins (e.g., RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6). In some embodiments, the present invention provides mutants of REEP and/or RTP polypeptides. In still other embodiments of the present invention, nucleic acid sequences corresponding to REEP and/or RTP variants, homologs, and mutants may be used to generate recombinant DNA molecules that direct the expression of the REEP and/or RTP variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 21-50 that encode substantially the same or a functionally equivalent amino acid sequence, may be used to clone and express REEP and/or RTP proteins. In general, such polynucleotide sequences hybridize to one of SEQ ID NOs: 21-50 under conditions of high to medium stringency as described above. As will be understood by those of skill in the art, it may be advantageous to produce REEP and/or RTP-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of REEP and/or RTP expression or to produce recombinant RNA transcripts having desirable properties, such as a longer half-life, than transcripts produced from naturally occurring sequence.

In preferred embodiments, REEP1, RTP1 and RTP2 polypeptides promote odorant receptor cell surface localization and odorant receptor functional expression.

1. Vectors for Production of REEP and RTP

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1-20). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1-20 is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the $E.\ coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.\ coli$).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of REEP and RTP Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

In preferred embodiments, the present invention provides a cell line (e.g., heterologous 293T cell line) comprising expression of an odorant receptor (e.g., human odorant receptor, murine odorant receptor, synthetic odorant receptor) localized to the cell surface, REEP1, RTP1, RTP2, and $G_{\alpha olf}$. In some embodiments, the odorant receptor is tagged with a reporting agent (e.g., glutathione-S-transferase (GST), c-myc, 6-histidine (6×-His), green fluorescent protein (GFP), maltose binding protein (MBP), influenza A virus haemagglutinin (HA), b-galactosidase, and GAL4). The cell line described in this embodiment is not limited to particular odorant receptors. In some embodiments, the odorant receptors expressed in the cell line include, but are not limited to, S6/79, S18, S46, S50, MOR23-1, MOR31-4, MOR31-6, MOR32-5 and MOR32-11. In preferred embodiments, cell lines expressing odorant receptors are used in the classification of an odorant receptor's functional expression (e.g., ligand specificity). In even further embodiments, cell lines expressing odorant receptors are used in the classification of an animal's olfactory sensation.

3. Purification of REEP and RTP Polypeptides

The present invention also provides methods for recovering and purifying REEP and/or RTP polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a REEP and/or RTP gene (e.g., SEQ ID NOs: 1-20) fused in frame to a marker sequence that allows for purification of the polypeptide of the present invention. A non-limiting example of a marker sequence is a hexa-histidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of REEP and RTP Polypeptides

In addition, the present invention provides fragments of REEP and/or RTP polypeptides (i.e., truncation mutants). In some embodiments of the present invention, when expression of a portion of the REEP and/or RTP protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al, J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing REEP and RTP

The present invention also provides fusion proteins incorporating all or part of the REEP and/or RTP polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a REEP and/or RTP protein. In some embodiments of the present invention, the VP6 capsid protein of rotavirus is used as an immunologic carrier protein for portions of a REEP and/or RTP polypeptide, either in the monomeric form or in the form of a viral particle. In other embodiments of the present invention, the nucleic acid sequences corresponding to the portion of a REEP and/or RTP polypeptide against which antibodies are to be raised can be incorporated into a fusion gene construct which includes coding sequences for a late vaccinia virus structural protein to produce a set of recombinant viruses expressing fusion proteins comprising a portion of REEP and/or RTP as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a REEP and/or RTP polypeptide and the poliovirus capsid protein are created to enhance immunogenicity of the set of polypeptide antigens (See e.g., EP Publication No. 025949; and Evans et al., Nature 339:385 [1989]; Huang et al, J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of REEP and/or RTP is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the REEP and/or RTP proteins can also be expressed and presented by bacterial cells.

In addition to utilizing fusion proteins to enhance immunogenicity, it is widely appreciated that fusion proteins can also facilitate the expression of proteins, such as a REEP and/or RTP protein of the present invention. Accordingly, in some embodiments of the present invention, REEP and/or RTP polypeptides can be generated as glutathione-S-transferase (i.e., GST fusion proteins). It is contemplated that such GST fusion proteins will enable easy purification of REEP and/or RTP polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a REEP and/or RTP polypeptide, can allow purification of the expressed REEP and/or RTP fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of REEP and RTP

Still other embodiments of the present invention provide mutant or variant forms of REEP and/or RTP polypeptides (i.e., muteins). It is possible to modify the structure of a peptide having an activity of a REEP and/or RTP polypeptide of the present invention for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject REEP and/or RTP proteins as defined herein. A modified peptide can be produced in which the amino acid sequence has been altered, such as by amino acid substitution, deletion, or addition.

Variant forms of RTP1 include but are not limited to RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6).

Moreover, as described above, variant forms (e.g., mutants or polymorphic sequences) of the subject REEP and/or RTP proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present REEP and/or RTP proteins, as well as truncation mutants, and is especially useful for identifying potential variant sequences (i.e., mutants or polymorphic sequences) that are involved in neurological disorders (e.g., olfactory disorders) or resistance to neurological disorders. The purpose of screening such combinatorial libraries is to generate, for example, novel REEP and/or RTP variants that can act as either agonists or antagonists, or alternatively, possess novel activities all together.

Therefore, in some embodiments of the present invention, REEP and/or RTP variants are engineered by the present method to provide altered (e.g., increased or decreased) biological activity. In other embodiments of the present invention, combinatorially-derived variants are generated which have a selective potency relative to a naturally occurring REEP and/or RTP. Such proteins, when expressed from recombinant DNA constructs, can be used in gene therapy protocols.

Still other embodiments of the present invention provide REEP and/or RTP variants that have intracellular half-lives dramatically different than the corresponding wild-type protein. For example, the altered protein can be rendered either more stable or less stable to proteolytic degradation or other cellular process that result in destruction of, or otherwise inactivate REEP and/or RTP polypeptides. Such variants, and the genes which encode them, can be utilized to alter the location of REEP and/or RTP expression by modulating the half-life of the protein. For instance, a short half-life can give rise to more transient REEP and/or RTP biological effects and, when part of an inducible expression system, can allow tighter control of REEP and/or RTP levels within the cell. As above, such proteins, and particularly their recombinant nucleic acid constructs, can be used in gene therapy protocols.

In still other embodiments of the present invention, REEP and/or RTP variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of REEP and/or RTP homologs, variants or other related proteins are aligned, preferably to promote the highest homology possible. Such a population of variants can include, for example, REEP and/or RTP homologs from one or more species, or REEP and/or RTP variants from the same species but which differ due to mutation or polymorphisms. Amino acids that appear at each position of the aligned sequences are selected to create a degenerate set of combinatorial sequences.

In a preferred embodiment of the present invention, the combinatorial REEP and/or RTP library is produced by way of a degenerate library of genes encoding a library of polypeptides which each include at least a portion of potential REEP and/or RTP protein sequences. For example, a mixture of synthetic oligonucleotides can be enzymatically ligated into gene sequences such that the degenerate set of potential REEP and/or RTP sequences are expressible as individual polypeptides, or alternatively, as a set of larger fusion proteins (e.g., for phage display) containing the set of REEP and/or RTP sequences therein.

There are many ways by which the library of potential REEP and/or RTP homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential REEP and/or RTP sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223, 409, 5,198,346, and 5,096,815; each of which is incorporated herein by reference).

It is contemplated that the REEP and/or RTP nucleic acids of the present invention (e.g., SEQ ID NOs: 1-20, and fragments and variants thereof) can be utilized as starting nucleic acids for directed evolution. These techniques can be utilized to develop REEP and/or RTP variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1: 17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for REEP and/or RTP activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for REEP and/or RTP activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of REEP and/or RTP homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of REEP and/or RTP Polypeptides

In an alternate embodiment of the invention, the coding sequence of REEP and/or RTP is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire REEP and/or RTP amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a REEP and/or RTP polypeptide, or any part thereof, may be altered during direct synthesis and/or combined using chemical methods with other sequences to produce a variant polypeptide.

IV. Detection of REEP and RTP Alleles

In some embodiments, the present invention provides methods of detecting the presence of wild type or variant (e.g., mutant or polymorphic) REEP and/or RTP nucleic acids or polypeptides. The detection of mutant REEP and/or RTP polypeptides finds use in the diagnosis of disease (e.g., olfactory disorder).

A. Detection of Variant REEP and/or RTP Alleles

In some embodiments, the present invention provides alleles of REEP and/or RTP that increase a patient's susceptibility to olfactory disorders (e.g., upper respiratory infections, tumors of the anterior cranial fossa, Kallmann syndrome, Foster Kennedy syndrome, Parkinson's disease, Alzheimer's disease, and Huntington chorea). Any mutation that results in an altered phenotype (e.g., diminished olfactory sensing ability) is within the scope of the present invention.

Accordingly, the present invention provides methods for determining whether a patient has an increased susceptibility to olfactory disorders (e.g., upper respiratory infections, tumors of the anterior cranial fossa, and Kallmann syndrome, Foster Kennedy syndrome, Parkinson's disease, Alzheimer's disease, Huntington chorea) by determining, directly or indirectly, whether the individual has a variant REEP and/or RTP allele. In other embodiments, the present invention provides methods for providing a prognosis of increased risk for olfactory disorder to an individual based on the presence or absence of one or more variant REEP and/or RTP alleles.

A number of methods are available for analysis of variant (e.g., mutant or polymorphic) nucleic acid or polypeptide sequences. Assays for detection variants (e.g., polymorphisms or mutations) via nucleic acid analysis fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, Nebr. or Varian, Palo Alto, Calif.), fragment length polymorphism assays (e.g., RFLP or CFLP (See e.g. U.S. Pat. Nos. 5,843,654; 5,843,669; 5,719, 208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858, 659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), polymorphisms detected directly or indirectly (e.g., detecting sequences (other polymorphisms) that are in linkage disequilibrium with the polymorphism to be identified; for example, other sequences in the SPG-6 locus may be used; this method is described in U.S. Pat. No. 5,612,179 (herein incorporated by reference)) and mass spectrometry assays.

In addition, assays for the detection of variant REEP and/or RTP proteins find use in the present invention (e.g., cell free translation methods, See e.g., U.S. Pat. No. 6,303,337, herein incorporated by reference) and antibody binding assays. The generation of antibodies that specifically recognize mutant versus wild type proteins are discussed below.

B. Kits for Analyzing Risk of Olfactory Disorders

The present invention also provides kits for determining whether an individual contains a wild-type or variant (e.g., mutant or polymorphic) allele or polypeptide of REEP and/or RTP. In some embodiments, the kits are useful determining whether the subject is at risk of developing an olfactory disorder (e.g., upper respiratory infections, tumors of the anterior cranial fossa, and Kallmann syndrome, Foster Kennedy syndrome, Parkinson's disease, Alzheimer's disease, Huntington chorea). The diagnostic kits are produced in a variety of ways. In some embodiments, the kits contain at least one reagent for specifically detecting a mutant REEP and/or RTP allele or protein. In preferred embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant REEP and/or RTP proteins.

In some embodiments, the kit contains instructions for determining whether the subject is at risk for an olfactory disorder (e.g, upper respiratory infections, tumors of the anterior cranial fossa, and Kallmann syndrome, Foster Kennedy syndrome, Parkinson's disease, Alzheimer's disease, Huntington chorea). In preferred embodiments, the instructions specify that risk for developing an olfactory disorder is determined by detecting the presence or absence of a mutant REEP and/or RTP allele in the subject, wherein subjects having an mutant allele are at greater risk for developing an olfactory disorder.

The presence or absence of a disease-associated mutation in a REEP and/or RTP gene can be used to make therapeutic or other medical decisions. For example, couples with a family history of odorant receptor related diseases may choose to conceive a child via in vitro fertilization and pre-implantation genetic screening. In this case, fertilized embryos are screened for mutant (e.g., disease associated) alleles of a REEP and/or RTP gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a REEP and/or RTP allele known to be associated with an olfactory disorder allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing an olfactory disorder (e.g., upper respiratory infections, tumors of the anterior cranial fossa, and Kallmann syndrome, Foster Kennedy syndrome, Parkinson's disease, Alzheimer's disease, Huntington chorea) based on the presence of one or more variant alleles of a REEP and/or RTP gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting an REEP and/or RTP related olfactory disorder associated with a given polymorphism, as well as the sequences). In some embodiments, one of the computers stores application programs (e.g., for analyzing the results of detection assays). Results are then delivered to the user (e.g., via one of the computers or via the internet).

For example, in some embodiments, a computer-based analysis program is used to translate the raw data generated by the detection assay (e.g., the presence, absence, or amount of a given REEP and/or RTP allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant REEP and/or RTP genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing an REEP and/or RTP related olfactory disorder) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given REEP and/or RTP allele with olfactory disorders.

V. Generation of REEP and RTP Antibodies

The present invention provides isolated antibodies or antibody fragments (e.g., FAB fragments). Antibodies can be generated to allow for the detection of REEP and/or RTP proteins (e.g., wild type or mutant) of the present invention. The antibodies may be prepared using various immunogens. In one embodiment, the immunogen is a human REEP and/or RTP peptide to generate antibodies that recognize human REEP and/or RTP. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a REEP and/or RTP polypeptide. For the production of antibody, various host animals can be immunized by injection with the peptide corresponding to the REEP and/or RTP epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward REEP and/or RTP, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing REEP and/or RTP specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for a REEP and/or RTP polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immudiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of REEP and/or RTP (e.g., for Western blotting), measuring levels thereof in appropriate biological samples, etc. The antibodies can be used to detect a REEP and/or RTP in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human REEP and/or RTP using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of REEP and/or RTP detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of REEP and/or RTP or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of REEP and/or RTP. Such antibodies can also be used diagnostically to measure abnormal expression of REEP1 and/or RTP, or the aberrant formation of protein complexes, which may be indicative of a disease state.

VI. Gene Therapy Using REEP and RTP

The present invention also provides methods and compositions suitable for gene therapy to alter REEP and/or RTP expression, production, or function for research, generation of transgenic animals, and/or therapeutic applications. As described above, the present invention provides human REEP and/or RTP genes and provides methods of obtaining REEP and/or RTP genes from other species. Thus, the methods described below are generally applicable across many species. In some embodiments, it is contemplated that the gene therapy is performed by providing a subject with a wild-type allele of a REEP and/or RTP gene (i.e., an allele that does not contain a REEP and/or RTP disease allele (e.g., free of disease causing polymorphisms or mutations)). Subjects in need of such therapy are identified by the methods described above. In some embodiments, transient or stable therapeutic nucleic acids are used (e.g., antisense oligonucleotides, siRNAs) to reduce or prevent expression of mutant proteins. In other embodiments, genes are deleted to reduce or block desired olfactory senses.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al, J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459, 127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VII. Transgenic Animals Expressing Exogenous REEP and RTP Genes and Homologs, Mutants, and Variants Thereof The present invention contemplates the generation of transgenic animals comprising an exogenous REEP and/or RTP gene or homologs, mutants, or variants thereof. In preferred embodiments, the transgenic animal displays an altered phenotype as compared to wild-type animals. In some embodiments, the altered phenotype is the overexpression of mRNA for a REEP and/or RTP gene as compared to wild-type levels of REEP and/or RTP expression. In other embodiments, the altered phenotype is the decreased expression of mRNA for an endogenous REEP and/or RTP gene as compared to wild-type levels of endogenous REEP and/or RTP expression. In some preferred embodiments, the transgenic animals comprise mutant alleles of REEP and/or RTP. Methods for analyzing the presence or absence of such phenotypes include Northern blotting, mRNA protection assays, and RT-PCR. In other embodiments, the transgenic mice have a knock out mutation of a REEP and/or RTP gene. In preferred embodiments, the transgenic animals display an altered susceptibility to olfactory disorders (e.g., upper respiratory infections, tumors of the anterior cranial fossa, and Kallmann syndrome, Foster Kennedy syndrome, Parkinson's disease, Alzheimer's disease, Huntington chorea).

Such animals find use in research applications (e.g., identifying signaling pathways that a REEP and/or RTP protein is involved in), as well as drug screening applications (e.g., to screen for drugs that prevent or treat olfactory disorders). For example, in some embodiments, test compounds (e.g., a drug that is suspected of being useful to treat an olfactory disorder) are administered to the transgenic animals and control animals with a wild type REEP and/or RTP allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of REEP and/or RTP is deleted). Methods for homologous recombination are described in U.S. Pat. No. 5,614,396, incorporated herein by reference.

VIII. Compound Screening Using REEP and RTP

In some embodiments, the isolated nucleic acid and polypeptides of REEP and/or RTP genes of the present invention (e.g., SEQ ID NOS: 1-50) and related proteins and nucleic acids are used in drug screening applications for compounds that alter (e.g., enhance or inhibit) REEP and/or RTP activity and signaling. The present invention further provides methods of identifying ligands and signaling pathways of the REEP and/or RTP proteins of the present invention.

The present invention is not limited to a particular mechanism. Indeed, an understanding of the mechanism is not necessary to practice the present invention. Nonetheless, based upon OR expression analysis experiments conducted during the course of the present invention, it is contemplated that REEP and/or RTP family proteins function in promoting odorant receptor cell surface localization and functional expression.

In some embodiments, the present invention provides methods of screening compounds for the ability to alter REEP and/or RTP activity mediated by natural ligands (e.g., identified using the methods described above). Such compounds find use in the treatment of disease mediated by REEP and/or RTP (e.g., olfactory disorders), the alteration of olfactory sensory responses, and the like.

In some embodiments, the present invention provides methods of screening compounds for an ability to interact with mutant REEP and/or RTP nucleic acid and/or mutant REEP and/or RTP polypeptides, while simultaneously not interacting with wild type REEP and/or RTP nucleic acid (e.g., SEQ ID NOS:1-20) and/or wild type REEP and/or RTP polypeptides (e.g., SEQ ID NOS:21-50). Such compounds find use in the treatment of olfactory disorders facilitated by the presence of mutant forms of REEP and/or RTP nucleic acids and/or proteins.

In some embodiments, the activity of cell surface localized ORs in cells expressing exogenous REEP or RTP polypeptides is assessed in response to compounds (e.g., candidate or ligands or inhibitors).

One technique uses REEP, RTP, or OR antibodies, generated as discussed above. Such antibodies are capable of specifically binding to REEP, RTP, or OR peptides and compete with a test compound for binding to REEP, RTP, or OR peptides. Similar screens can be carried out with small molecule libraries, aptamers, etc.

The present invention contemplates the use of cell lines transfected with REEP and/or RTP genes and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level.

In second messenger assays, the host cells are preferably transfected as described above with vectors encoding REEP and/or RTP or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors or of ORs localized at the cell membrane. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DAB-CYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

The ability of the test compound to modulate REEP and/or RTP binding to a compound, e.g., an odorant receptor, can also be evaluated. This can be accomplished, for example, by coupling the compound, e.g., the substrate, with a radioisotope or enzymatic label such that binding of the compound, e.g., the substrate, to REEP and/or RTP can be determined by detecting the labeled compound, e.g., substrate, in a complex.

Alternatively, REEP and/or RTP is coupled with a radioisotope or enzymatic label to monitor the ability of a test compound to modulate REEP and/or RTP binding to a REEP and/or RTP substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting.

Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an odorant receptor) to interact with REEP and/or RTP with or without the labeling of any of the interactants can be evaluated. For example, a microphysiometer can be used to detect the interaction of a compound with REEP and/or RTP without the labeling of either the compound or the REEP and/or RTP (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a REEP and/or RTP polypeptide.

In yet another embodiment, a cell-free assay is provided in which REEP and/or RTP protein or biologically active portion thereof is contacted with a test compound and the ability of the test compound to bind to the REEP and/or RTP protein or biologically active portion thereof is evaluated. Preferred biologically active portions of REEP and/or RTP proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

Modulators of REEP and/or RTP expression can also be identified. For example, a cell or cell free mixture is contacted with a candidate compound and the expression of REEP and/or RTP mRNA or protein evaluated relative to the level of expression of the REEP and/or RTP mRNA or protein in the absence of the candidate compound. When expression of the REEP and/or RTP mRNA or protein is greater in the presence of the candidate compound than in its absence, the candidate compound is identified as a stimulator of a REEP and/or RTP mRNA or protein expression. Alternatively, when expression of REEP and/or RTP mRNA or protein is less (i.e., statistically significantly less) in the presence of the candidate compound than in its absence, the candidate compound is identified as an inhibitor of REEP and/or RTP mRNA or protein expression. The level of REEP and/or RTP mRNA or protein expression can be determined by methods described herein for detecting REEP and/or RTP mRNA or protein.

A modulating agent can be identified using a cell-based or a cell free assay, and the ability of the agent to modulate the activity of a REEP and/or RTP protein can be confirmed in vivo, e.g., in an animal such as an animal model for a disease (e.g., an animal with an REEP and/or RTP related olfactory disorder).

B. Therapeutic Agents

This invention further pertains to novel agents identified by the above-described screening assays. Accordingly, it is within the scope of this invention to further use an agent identified as described herein (e.g., a REEP and/or RTP modulating agent or mimetic, a REEP and/or RTP specific antibody, a REEP and/or RTP-binding partner, or an OR agonist or inhibitor) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of olfactory disorders (e.g., including, but not limited to, olfactory disorders).

IX. Pharmaceutical Compositions Containing REEP and RTP Nucleic Acid, Peptides, and Analogs The present invention further provides pharmaceutical compositions which may comprise all or portions of REEP and/or RTP polynucleotide sequences, REEP and/or RTP polypeptides, inhibitors or antagonists of REEP and/or RTP bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant REEP and/or RTP alleles (e.g., upper respiratory infections, tumors of the anterior cranial fossa, and Kallmann syndrome, Foster Kennedy syndrome, Parkinson's disease, Alzheimer's disease, Huntington chorea). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, REEP and/or RTP nucleotide and REEP and/or RTP amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, REEP and/or RTP polynucleotide sequences or REEP and/or RTP amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of REEP and/or RTP may be that amount that suppresses olfactory disorder related symptoms. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of REEP and/or RTP, conditions indicated on the label may include treatment of condition related to olfactory disorders.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts REEP and/or RTP levels.

A therapeutically effective dose refers to that amount of REEP and/or RTP that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for REEP and/or RTP than for the inhibitors of REEP and/or RTP. Administration to the bone marrow may necessitate delivery in a manner different from intravenous injections.

X. RNA Interference (RNAi)

RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

XI. RNAi for REEP and RTP

As discussed above, the present invention provides RNAi for inhibiting the expression of the REEP and/or RTP polypeptide in cells, ORs, or pathway components involved in the expression or activity of such components.

A. Designing and Testing RNAi for REEP and/or RTP

In order to design siRNAs for REEP and/or RTP (e.g. that target REEP and/or RTP mRNA) software design tools are available in the art (e.g. on the Internet). For example, Oligoengine's web page has one such design tool that finds RNAi candidates based on Elbashir's (Elbashir et al, Methods 2002; 26: 199-213, herein incorporated by reference) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously.

siRNA candidate molecules that are generated can be, for example, screened in an animal model of an olfactory disorder for the quantitative evaluation of REEP and/or RTP expression in vivo using similar techniques as described above.

B. Expression Cassettes

REEP and/or RTP specific siRNAs of the present invention may be synthesized chemically. Chemical synthesis can be achieved by any method known or discovered in the art. Alternatively, REEP and/or RTP specific siRNAs of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods that comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for REEP and/or RTP. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

C. Vectors

In other aspects of the present invention, the compositions comprise a vector comprising a gene encoding an siRNA specific for REEP and/or RTP or preferably at least one expression cassette comprising a promoter and a gene which encodes a sequence necessary for the production of a siRNA specific for REEP and/or RTP (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, O C (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for REEP1, RTP1, RTP2, RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6)) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the GneSilencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern. Therefore, SEQ ID NOS: 1-20, for example, may be used with in a Vector (both Plasmid and Viral) delivery systems.

It is noted that Ambion offers a design tool for a vector on their web page, and BD Biosciences offers a manual for the design of a vector, both of which are useful for designing vectors for siRNA.

D. Transfecting Cells

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, and BHK cell lines. Specific examples of host cells in vivo include tumor tissue and eye tissue.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells.

In the present invention, cells to be transfected in vitro are typically cultured prior to transfection according to methods which are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267: 963; Wu and Wu (1988) J. Biol. Chem., 263:14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In preferred embodiments, the transfecting agent is OLIGOFECTAMINE. OLIGOFECTAMINE is a lipid based transfection reagent. Additional example of lipid based transfection reagents that were designed for the transfection of dsRNAis are the Transit-TKO reagent which is provided by Mirus (Madison, Wis.) and the jetSI which was introduced by Polyplus-trasfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

E. Kits

The present invention also provides kits comprising at least one expression cassette comprising a siRNA gene specific for REEP and/or RTP. In some aspects, a transcript from the expression cassette forms a double stranded siRNA of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene encodes one strand of a siRNA that combines with a strand encoded by a second cassette to form a ds siRNA; the ds siRNA so produced is any of the embodiments described above. These cassettes may comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

In some embodiments, the present invention provides kits comprising; a) a composition comprising small interfering RNA duplexes (siRNAs) configured to inhibit expression of the REEP and/or RTP protein, and b) printed material with instructions for employing the composition for treating a target cell expressing REEP and/or RTP protein via expression of REEP and/or RTP mRNA under conditions such that the REEP and/or RTP mRNA is cleaved or otherwise disabled. In certain embodiments, the printed material comprises instructions for employing the composition for treating eye disease.

F. Generating REEP and/or RTP Specific siRNA

The present invention also provides methods of synthesizing siRNAs specific for REEP and/or RTP (e.g. human REEP and/or RTP) or specific for mutant or wild type forms of REEP and/or RTP. The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the REEP and/or RTP gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo.

XII. Identification of Odorant Receptor Ligands

The present invention provides methods for identifying ligands specific for odorant receptors. The present invention is not limited to a particular method for identifying ligands specific for odorant receptors. In preferred embodiments, the present invention provides a cell line (e.g., heterologous 293T cell line) expressing an odorant receptor of interest (e.g., any human odorant receptor) localized to the cell surface, REEP1, RTP1 or variant thereof, RTP2, and $G_{\alpha olf}$. Activation of an odorant receptor results in an increase in cAMP. As such, in some embodiments, the cell line further comprises a cAMP responsive element linked with a reporting agent (e.g., luciferase) for detecting odorant receptor activation. An odiferous molecule (e.g., eugenol) is exposed to the cell line. If the odiferous molecule is a ligand specific for the odorant receptor, luciferase expression or a change in luciferase expression is detectable (see, e.g., Example 7).

EXAMPLES

To identify accessory proteins that are involved in targeting ORs to the cell surface, genes were screened for inducing functional cell surface expression of ORs in HEK293T (293T) cells. It was discovered REEP1, RTP1, RTP2, RTP1-A, RTP1-B, RTP1-C, RTP1-D, and RTP1-E, RTP1-A1, RTP1-D1, RTP-D2, RTP-D3, RTP1-A1-A (Chimera 1), RTP1-A1-D2 (Chimera 2), RTP1-A1-D1 (Chimera 3), RTP4-A1-A (Chimera 4), RTP4-A1-D2 (Chimera 5), and RTP4-A1-D1 (Chimera 6), were discovered that promote cell surface expression of ORs. These proteins are expressed by olfactory neurons, interact with OR proteins, and enhance responses to odorants when co-expressed with ORs in 293T cells. Furthermore, this has allowed construction of a heterologous expression system to identify new ORs that respond to aliphatic odorants.

Example 1

Identification of Odorant Receptor Accessory Proteins

Figure 1:
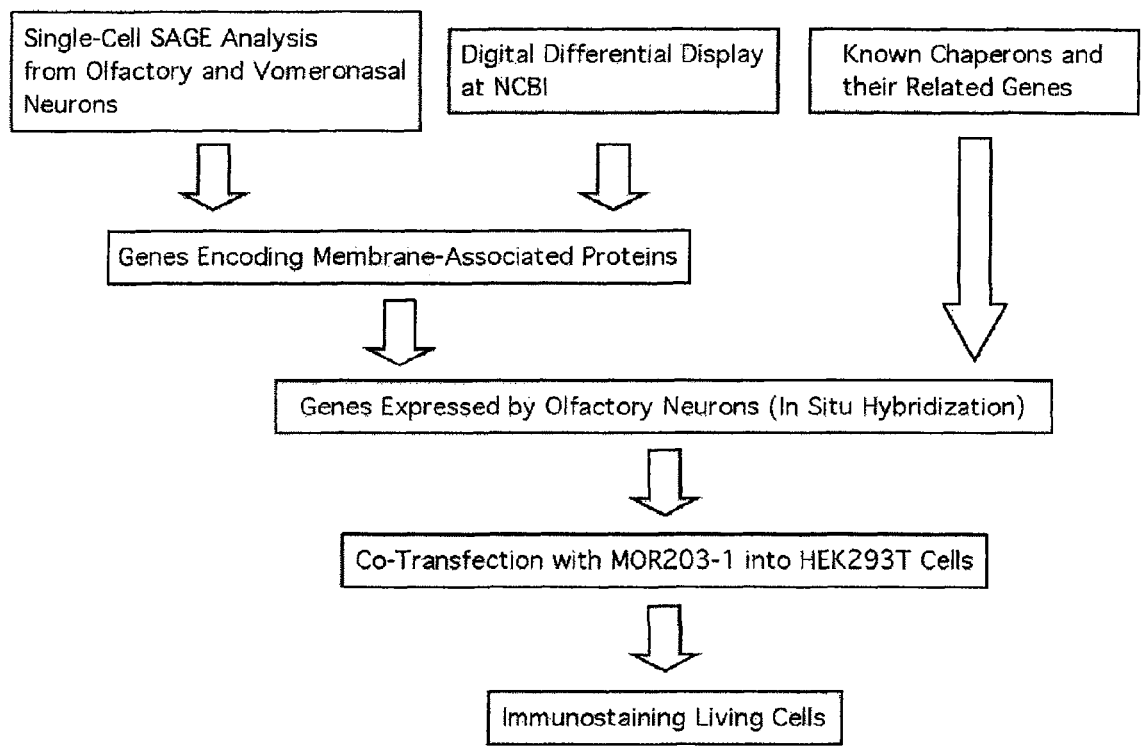
FIG. 1 shows a screening strategy for identifying molecules that promote cell-surface expression of odorant receptors. REEP1 was obtained from Digital Differential Display analysis. RTP1 was obtained from SAGE libraries.

After hypothesizing that mammalian ORs require accessory protein(s) for functional cell surface expression, a search was instituted for detecting such molecule(s). Long-SAGE (serial analysis of gene expression) libraries (see, e.g., Saha, S., et al., (2002) Nat Biotechnol 20, 508-512; herein incorporated by reference in its entirety) were constructed from single olfactory neurons as well as neurons from the vomeronasal organ and genes were collected that are expressed by these neurons. To identify candidate genes expressed by the olfactory neurons Digital Differential Display (see, e.g., http://www.ncbi.nlm.nih.gov UniGene/info_ddd.shtml) was also used. Candidate genes were investigated for ORFs that encode membrane associated proteins. Genes were selected with similarities to known chaperones and cloned the cDNAs from olfactory epithelium cDNAs. The mRNA expression of each gene was verified by in situ hybridization. After isolating and subcloning into mammalian expression vectors, each cDNA together with a mouse OR (MOR203-1) tagged with a 20 N-terminal amino acids of rhodopsin (Rho-tag), was transfected into 293T cells. Measurements were made assessing whether these clones had any effect on the cell-surface expression of ORs by staining living cells using antibodies against the Rho-tag (see, e.g., Laird, D. W., and Molday, R. S. (1988) Invest Opthalmol V is Sci 29, 419-428; herein incorporated by reference in its entirety). When MOR203-1 was transfected alone, antibody staining detected only faint cell-surface expression in less than 1% of the cells. A schematic diagram outlining the screening procedure utilized with the present invention is provided at FIG. 1.

Example 2

REEP and/or RTP Enhance Cell Surface Expression of ORs

Figure 2:
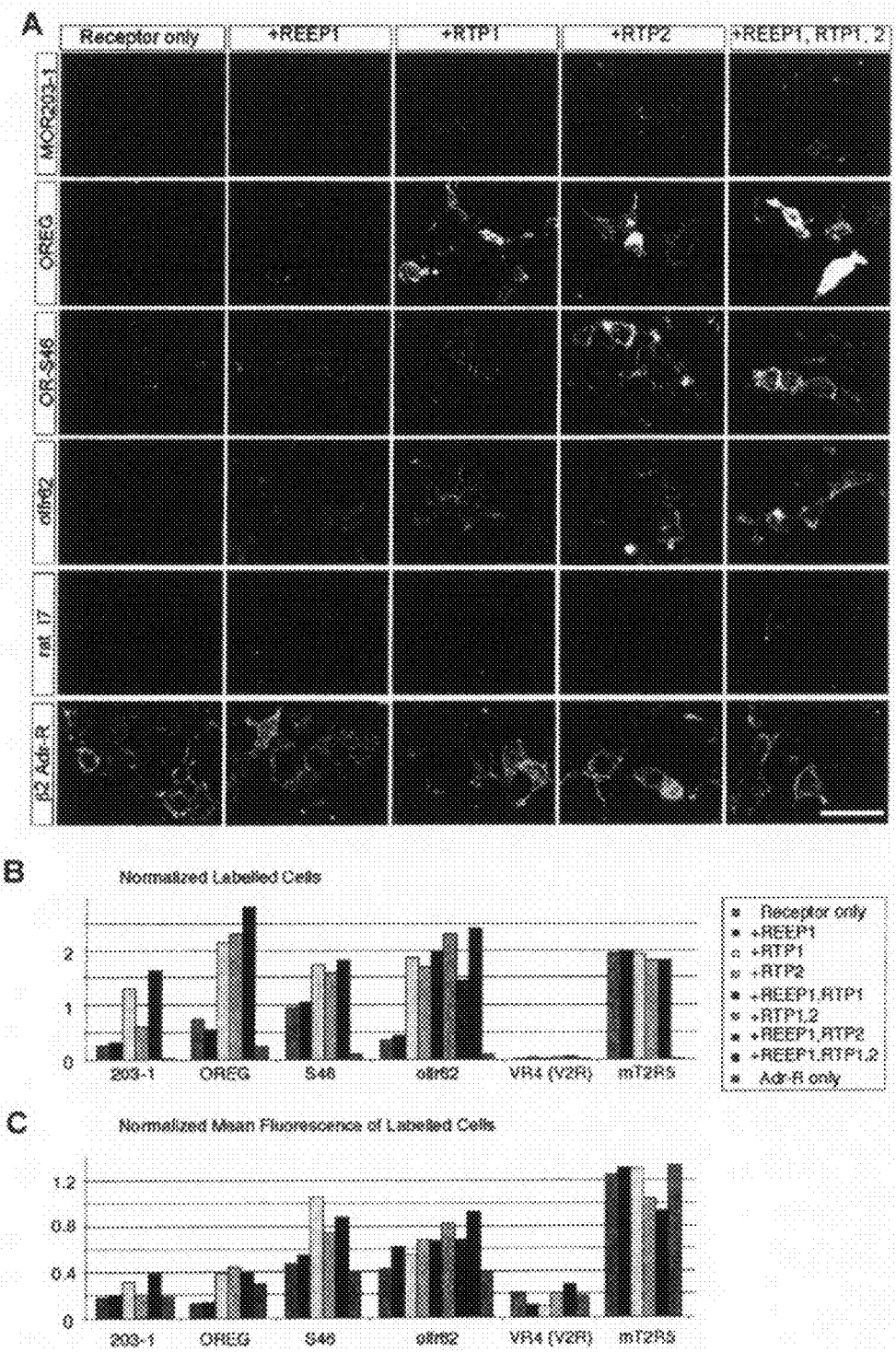
FIG. 2 shows REEP and/or RTP promote cell-surface expression of odorant receptors in 293T Cells. (A) cDNAs encoding diverse ORs (MOR203-1, OREG, olfr62, OR-S46 and rat 17) were transfected with or without REEP1, RTP1 and/or RTP2. Increased cell-surface staining of ORs was seen in cells co-expressing the accessory proteins. In contrast, no difference in cell-surface staining was seen in cells expressing β2 adrenergic receptors. Using living-cell staining protocols, cell-surface fluorescent signals are seen as distinctive punctate staining. Scale bar equals to 50 um. (B) Normalized numbers of labelled cells is shown for each transfection condition (N=4918-15526). After double immunofluorescent staining against Rho-tagged receptors and the HA-tagged β2 adrenergic receptor, FACS analysis was performed to quantify immunopositive cells. The number of Rho-tagged receptor positive cells was normalized to that of HA-tagged β2 adrenergic receptor positive cells. In almost all cases, more immunopositive cells were observed when different ORs were expressed with REEP1, RTP1 and/or RTP2. In contrast, when VR4 and mT2R5 receptor was used instead of ORs, no enhancement was observed. (C) Normalized mean fluorescence of labelled cells is shown. The mean fluorescence of β2 adrenergic receptor was used as a control. Stronger fluorescence was observed when different ORs were expressed with REEP1, RTP1 and/or RTP2. In contrast, when VR4 and mT2R5 receptor was used instead of ORs, no enhancement was observed. (D) A summary of the FACS analysis is shown.
Figure 3:
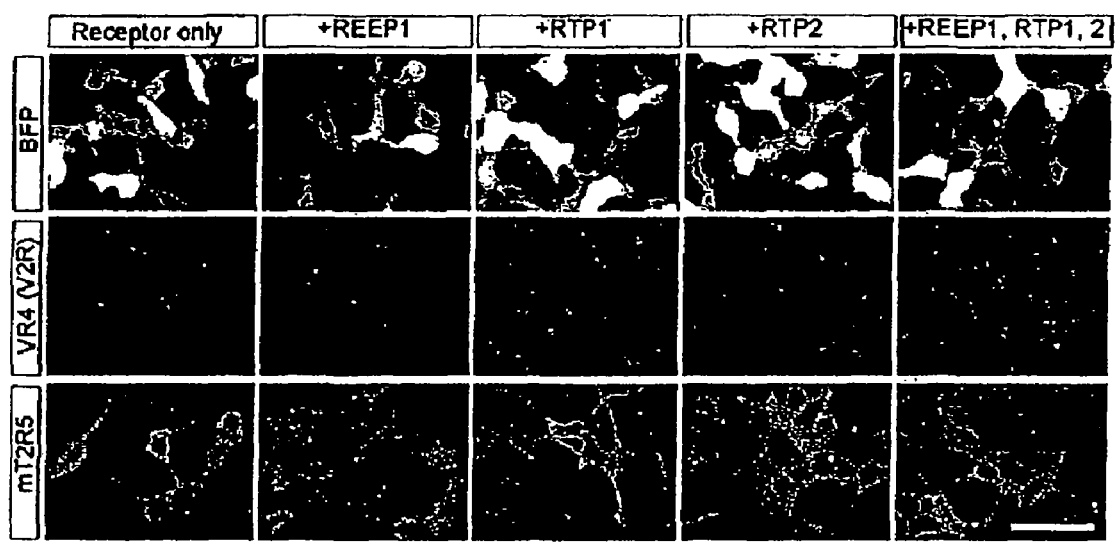
FIG. 3 shows that REEP and/or RTP do not promote cell-surface expression of VR4 and mT2R5 in 293T Cells. cDNAs encoding VR4 and mT2R5 were transfected with or without REEP1, RTP1 and/or RTP2. Unlike ORs, increased cell-surface staining was not seen in cells expressing these proteins. BFP expression is shown to demonstrate high (~70%) transfection efficiency of VR4 transfected cells. Using living-cell staining protocols, cell-surface fluorescent signals are seen as distinctive punctate staining. Scale bar equals to 50 um.
Figure 4A:
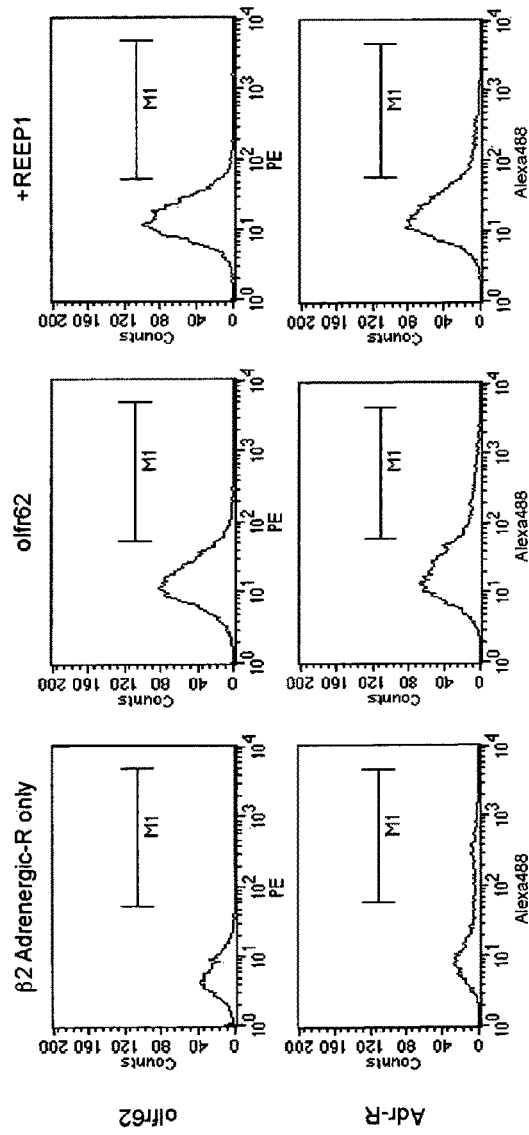
FIG. 4 presents fluorescent hisogram data for REEP1, RTP1, and RTP2 expression with odorant receptor (A) olfr62 and (B) mT2R5.
Figure 4B:
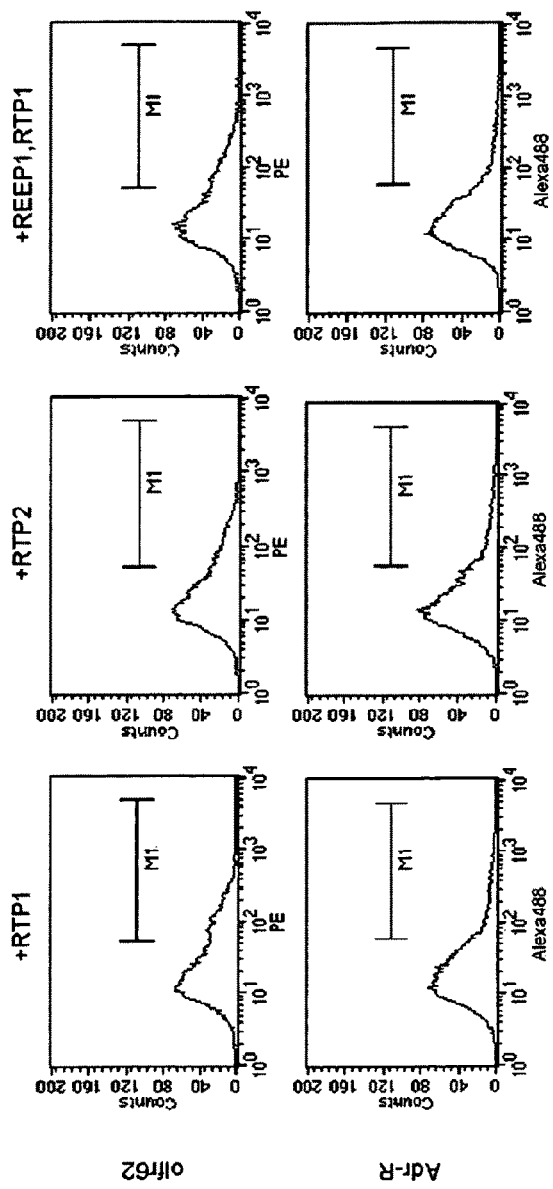
Figure 4C:
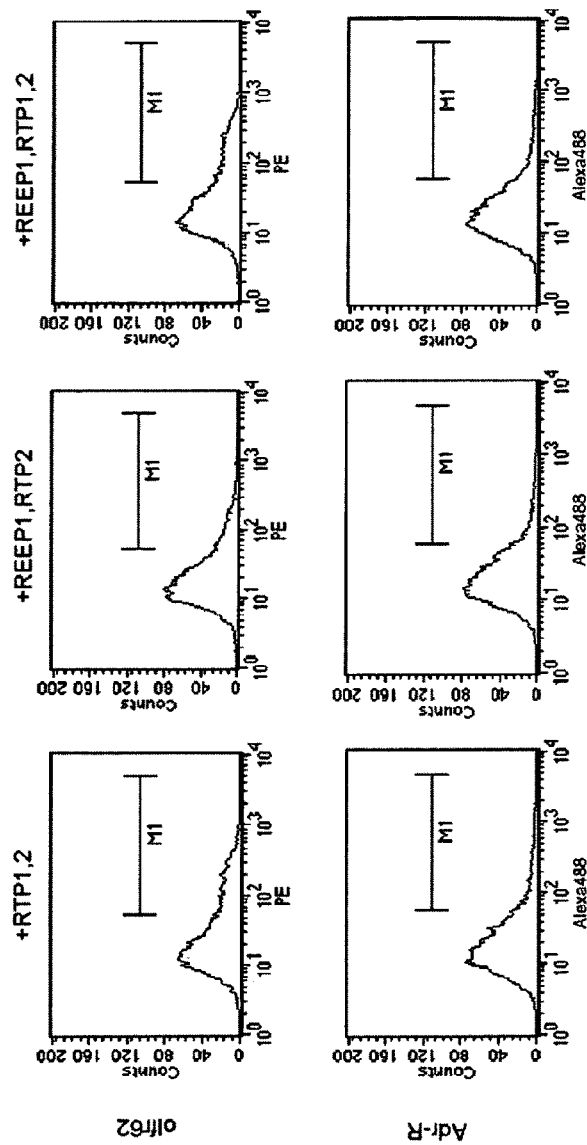
Figure 4D:
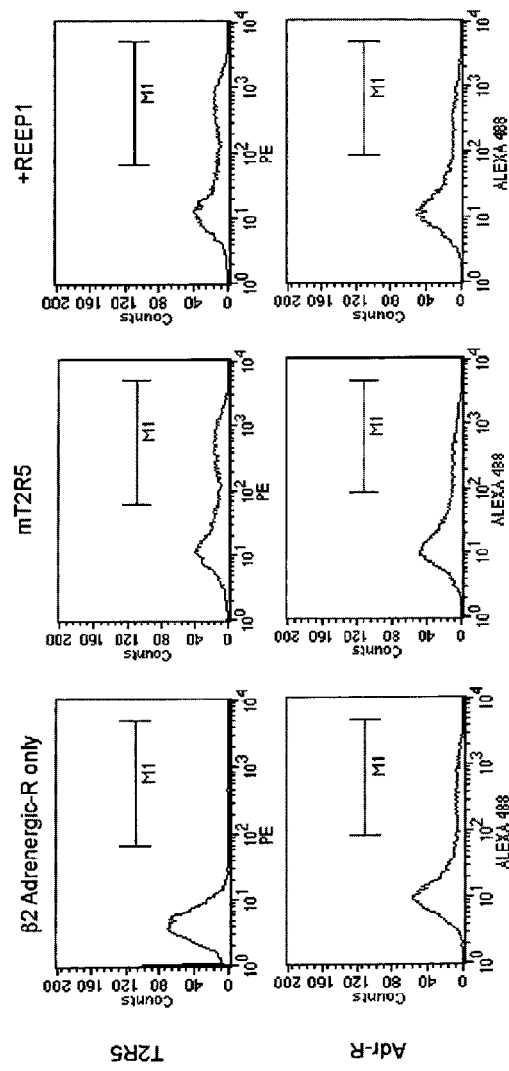
Figure 4E:
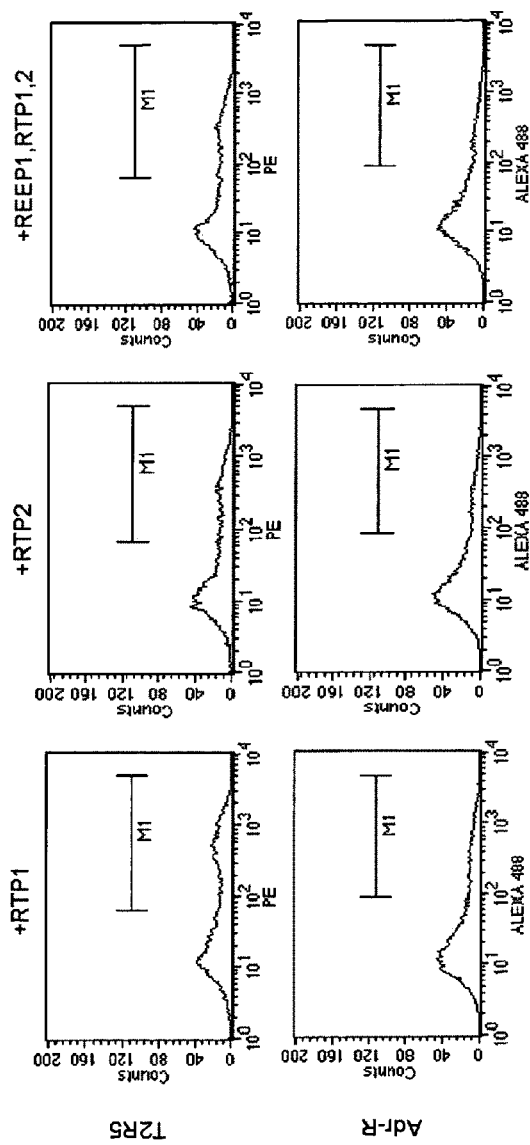

Two unrelated clones (of 61 tested) enhanced both the number and staining intensity of cell surface expression of MOR203-1 (see FIG. 2A). The proteins encoded by these clones were named REEP1, for Receptor Expression Enhancing Protein 1 and RTP1, for Receptor Transporting Protein 1. Subsequently, RTP2 was found, a close relative of RTP1. RTP2 also enhanced cell surface expression of MOR203-1. Next, REEP1, RTP1, and RTP2 were tested to detect a similar effect in promoting cell-surface expression of other ORs. Four different ORs (mouse OREG, mouse olfr62, mouse OR-S46 and rat 17) were expressed in 293T cells with or without REEP1, RTP1, or RTP2. Co-transfection of BFP or GFP demonstrated that transfection efficiency was consistent (~70%). Additionally, ORs transfected with REEP and/or RTP generated more immunofluorescent cells and stronger signals in positive cells compared with ORs without REEP and/or RTP (see FIG. 2A). The signal intensity and the number of immunopositive cells varied when using different ORs at each condition. For example, in the case of rat 17, the surface expression was significantly lower than that of other ORs tested. Nonetheless, occasional immunopositive cells were observed only when the accessory proteins were co-expressed. The effects of RTP1 or RTP2 were consistently more robust than that of REEP1. The enhancement of cell-surface expression was specific for ORs and not for other GPCRs: neither REEP and/or RTP enhanced expression of the β2 adrenergic receptor, mT2R5 (a mouse bitter taste receptor) (see, e.g., Chandrashekar, J., et al. (2000) Cell 100, 703-711; herein incorporated by reference in its entirety), or a V2R pheromone receptor (VR4) (see, e.g., Matsunami, H., and Buck, L. B. (1997) Cell 90, 775-784; herein incorporated by reference in its entirety) (see FIG. 2A and FIG. 3). Finally, enhancement of cell-surface expression of MOR203-1 was not observed when other members of the REEP and RTP families (REEP2 and RTP4) were co-expressed.

In order to quantify the numbers and intensity of immunopositive cells, Fluorescence-activated cell sorting (FACS) analysis was performed. To monitor transfection and staining efficiency, HA-tagged β2 adrenergic receptor was used as a control. More cells were labelled and the fluorescent signal was higher when ORs were expressed with the accessory proteins (see FIGS. 2B and 2C and FIG. 4).

Example 3

REEP and/or RTP Genes Encode Transmembrane Proteins

The REEP1 gene encodes a protein of 201 amino acids, containing two putative transmembrane domains (see FIG. 5A). Immunostaining of C-terminal tagged REEP1 protein indicate that the C-terminal end is extracellular. BLAST searches identified homologous genes in diverse eukaryotic species. REEP1 showed limited similarities with yeast YOP1, barley HVA22, and human DP1/TB2 (see FIG. 5B). YOP1 is implicated in vesicular transport (see, e.g., Brands, A., and Ho, T. H. (2002) Plant Physiol 130, 1121-1131; herein incorporated by reference in its entirety). Expression of HVA22 is induced by abscisic acid and regulated by various environmental stresses such as extreme temperatures or dehydration (see, e.g., Chen, C. N., et al. (2002) Plant Mol Biol 49, 633-644; Shen, Q., et al. (1993) J Biol Chem 268, 23652-23660; each herein incorporated by reference in their entireties). DP1/TB2 is encoded by a gene deleted in colon cancers (see, e.g., Kinzler, K. W., et al. (1991) Science 253, 661-665; herein incorporated by reference in its entirety) and a mouse homolog of DP1 (REEP5) is downregulated when mast cells are triggered by IgE plus antigen (see, e.g., Prieschl, E., et al. (1996) Gene 169, 215-218; herein incorporated by reference in its entirety). In the mouse genome, REEP1 has at least 5 additional homologous genes (designated REEP2-6) (see FIG. 5B).

RTP1 and RTP2 genes encode proteins with 263 and 223 amino acids, respectively and share a 73% sequence identity in amino acid level (see FIG. 5C). Neither protein appears to have a signal sequence but both have a single putative transmembrane domain located near the C-terminal end. Immunostaining of the C-terminal tagged RTP1 suggest that C-terminal end is extracellular. BLAST searches of the mouse genome identified two additional members, RTP3 and RTP4. There were no obvious RTP homologs outside vertebrate species. Nevertheless, C. elegans ODR-4 (see, e.g., Dwyer, N. D., et al. (1998) Cell 93, 455-466; herein incorporated by reference in its entirety) appears to have the same membrane topology as the RTPs.

Example 4

REEP and/or RTP are Specifically Expressed in Olfactory Neurons

Northern blot analysis with RNAs extracted from various mouse tissues revealed that REEP1 and especially RTP1 and RTP2 are most prominently expressed in olfactory and vomeronasal organs. REEP1 RNA was also detected at significant levels in the brain (see FIG. 6A). Long exposure revealed faint signals for RTP1 and RTP2 in the brain. Expression in testis was not observed, where a subset of ORs are expressed (see, e.g., Parmentier, M., et al. (1992) Nature 355, 453-455; Spehr, M., et al. (2003) Science 299, 2054-2058; each herein incorporated by reference in their entireties).

Figure 6:
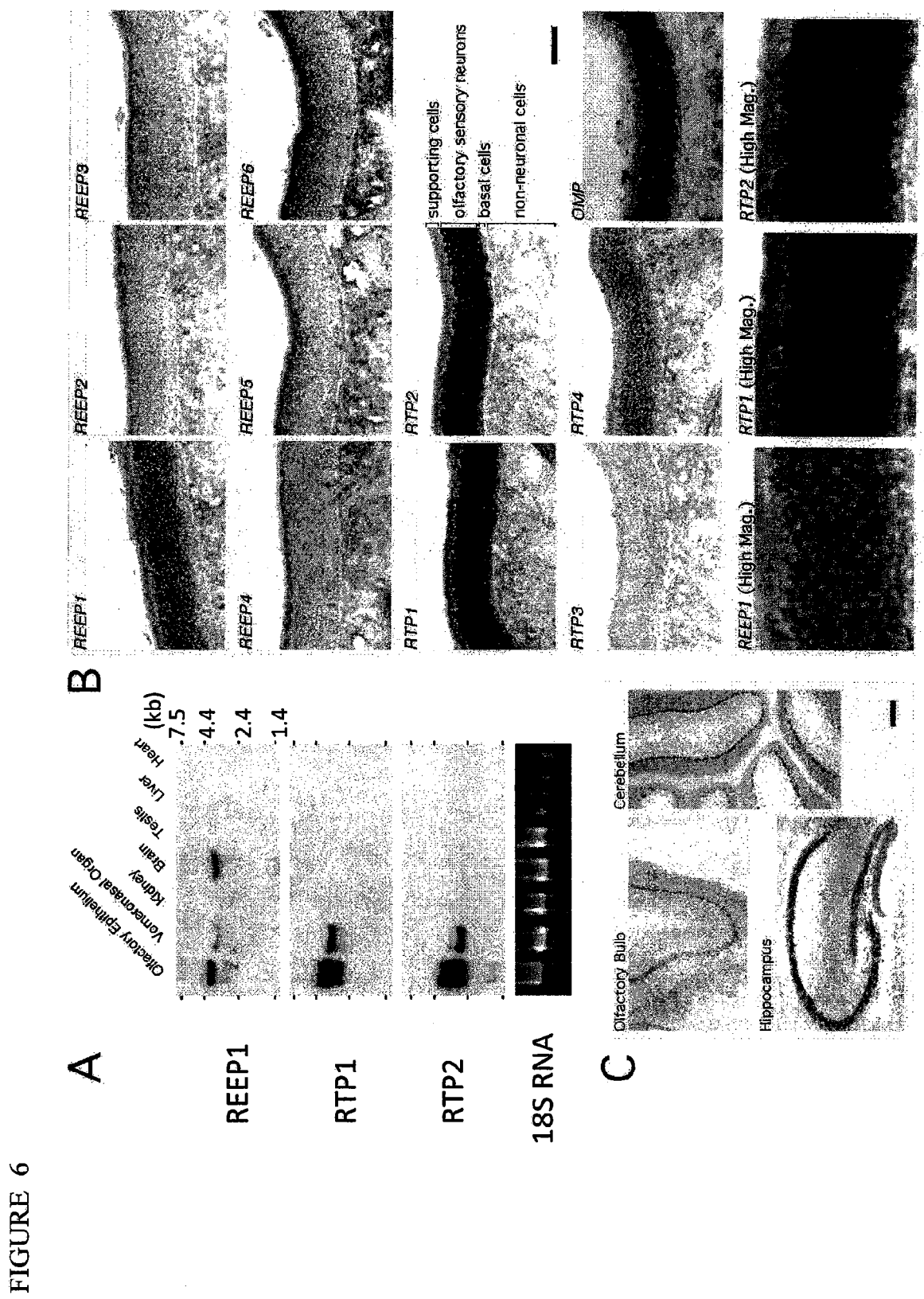
FIG. 6 shows expression of REEP1, RTP1 and RTP2. (A) Northern blot analysis. Total RNA was used for northern blotting analysis. Olfactory epithelium, vomeronasal organ, and brain showed ~3.6 kb bands corresponding to REEP1 mRNA. Only olfactory epithelium and vomeronasal organ RNAs showed ~3.5 kb and ~2.6 kb bands corresponding RTP1 and RTP2 mRNA, respectively. Ethidium bromide staining for 18S rRNA is shown as a control. (B) In situ hybridization analysis in the olfactory epithelium. Among REEP members, only REEP1 was expressed specifically by the olfactory neurons. REEP6 was expressed by supporting cells. Among RTP members, RTP1 and RTP2 are strongly expressed by the olfactory neurons. RTP4 was also expressed by the olfactory neurons but at much lower level. OMP is a marker for mature olfactory neurons. Higher magnification of REEP1, RTP1, and RTP2 suggests that all olfactory neurons may express all three molecules. Scale bar: 200 um (70 um in high magnification pictures). (C) In situ analysis of REEP1 in the brain. REEP1 was expressed by a subset of brain cells. Scale bar: 200 um.

In the olfactory epithelium, REEP and/or RTP were expressed specifically in olfactory neurons, which is evident from comparison with OMP expression, a marker for mature olfactory sensory neurons (see FIG. 6B). To avoid cross hybridization between RTP1 and RTP2 RNA, which are 87% identical at nucleotide level across the coding sequence, non-homologous 3'UTR regions as probes were used in addition to probes corresponding to the open reading frames. The signals were identical. No expression of other REEP or RTP genes was detected in olfactory neurons with the exception of RTP4 which was expressed at lower levels (see FIG. 6B). Finally, REEP1 was expressed by a subset of brain cells (see FIG. 6C).

Example 5

REEP1 and RTP1 can Interact with ORs

Given the ability of REEP and/or RTP to promote cell-surface expression of ORs, it was hypothesized that they may also interact with OR proteins. This was assessed using co-immunoprecipitation assays. HA-tagged MOR203-1 and Flag-tagged REEP1, RTP1 or ICAP-1, a negative control (see, e.g., Zawistowski, J. S., et al. (2002) Hum Mol Genet. 11, 389-396; herein incorporated by reference in its entirety) were transfected in 293T cells. After the cell extracts were precipitated with anti-Flag antibodies, proteins were eluted in SDS-sample buffer at room temperature whereupon western blotting analysis was performed to detect the OR proteins. OR proteins were detected as high molecular weight bands after precipitation of REEP1 or RTP1 (see FIG. 7B, lanes 1 and 2). The majority of a control GPCR, β2 adrenergic receptor, did not form high-molecular weight oligomers using these elution conditions. Similarly, when the HA-MOR203-1 proteins were precipitated, REEP1 or RTP1 proteins were co-precipitated whereas ICAP-1 was not detectable (see FIG. 7C, lanes 1, 2 and 3). The present invention is not limited to a particular mechanism. Indeed, an understanding of the mechanism is not necessary to practice the present invention. Nonetheless, these results indicate that REEP1 and RTP1 complex with ORs.

Based on the protein interaction, it was hypothesized that the functional expression of the accessory proteins might be regulated by the OR proteins. When only C-terminal Flag-tagged RTP1 was transfected into 293T cells, little cell-surface signal was detected, indicating that the majority of RTP proteins was inside the cells. In contrast, co-transfection of RTP1 and OR greatly enhanced cell-surface RTP1 (see FIG.

7D). The present invention is not limited to a particular mechanism. Indeed, an understanding of the mechanism is not necessary to practice the present invention. Nonetheless, these results demonstrated mutual dependence of ORs and RTP1 for cell-surface expression and indicated that effective cell surface expression of the both ORs and RTP1 requires the formation of a relatively stable receptor complex between the two. When the C-terminal tagged REEP1 was expressed, a small amount of cell-surface REEP1 was observed. Unlike RTP1, co-expression of the OR proteins did not facilitate cell-surface expression of REEP1 (see FIG. 7E).

Example 6

REEP and/or RTP Enhance OR Function

Figure 8:
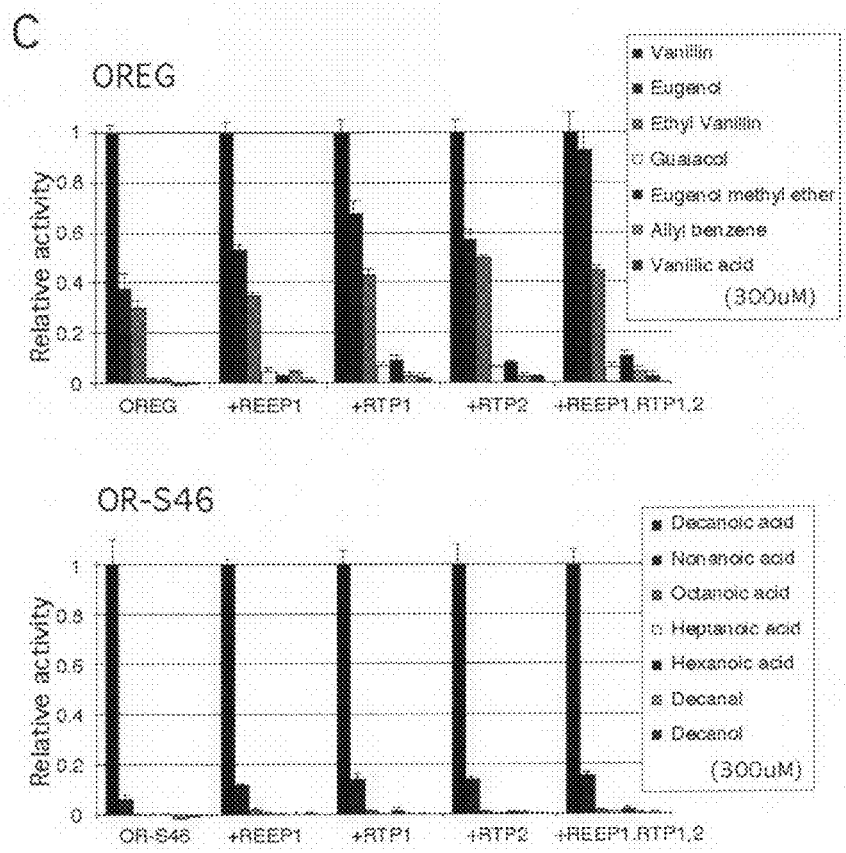
FIG. 8 shows that expression of REEP1, RTP1 or RTP 2 enhances odorant receptor activation. (A) Diagram showing cAMP responsive element (CRE) and luciferase was used to monitor activation of ORs. Activation of ORs increases cAMP, which enhances the expression of luciferase reporter gene through the CRE. (B) Normalized luciferase activities±SEM (N=4). REEP1, RTP1 and RTP2, expressed in various combination together with OREG, enhanced luciferase activities compared to OR alone. (C) Relative luciferase activities+SEM (N=4). OREG or OR-S46 was used to ask if REEP1, RTP1, or RTP2 could change ligand specificities of ORs. To obtain relative activation to different odorants, luciferase activity to 300 uM of vanillin (OREG) or decanoic acid (OR-S46) was regarded as 1 in each expression condition. (D) Normalized luciferase activities+SEM (N=8). Enhanced response in Hana3A cells, a stable cell line expressing REEP1, RTP1, RTP2 and Golf, when three different ORs were expressed.
Figure 8:
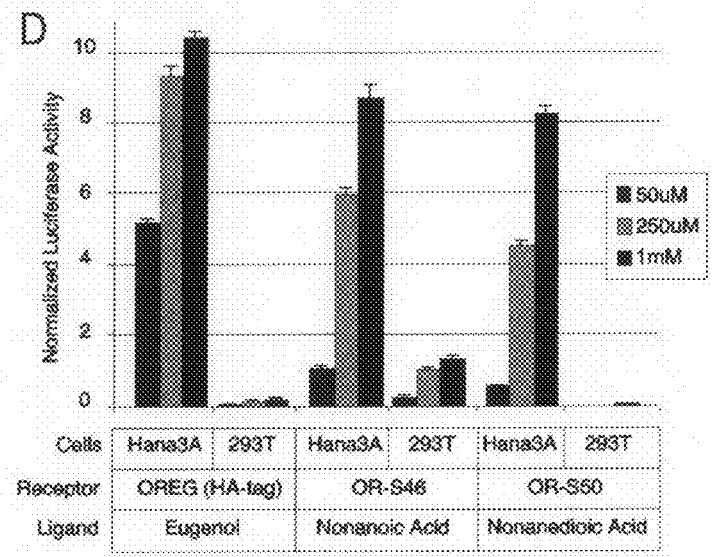
Figure 8:
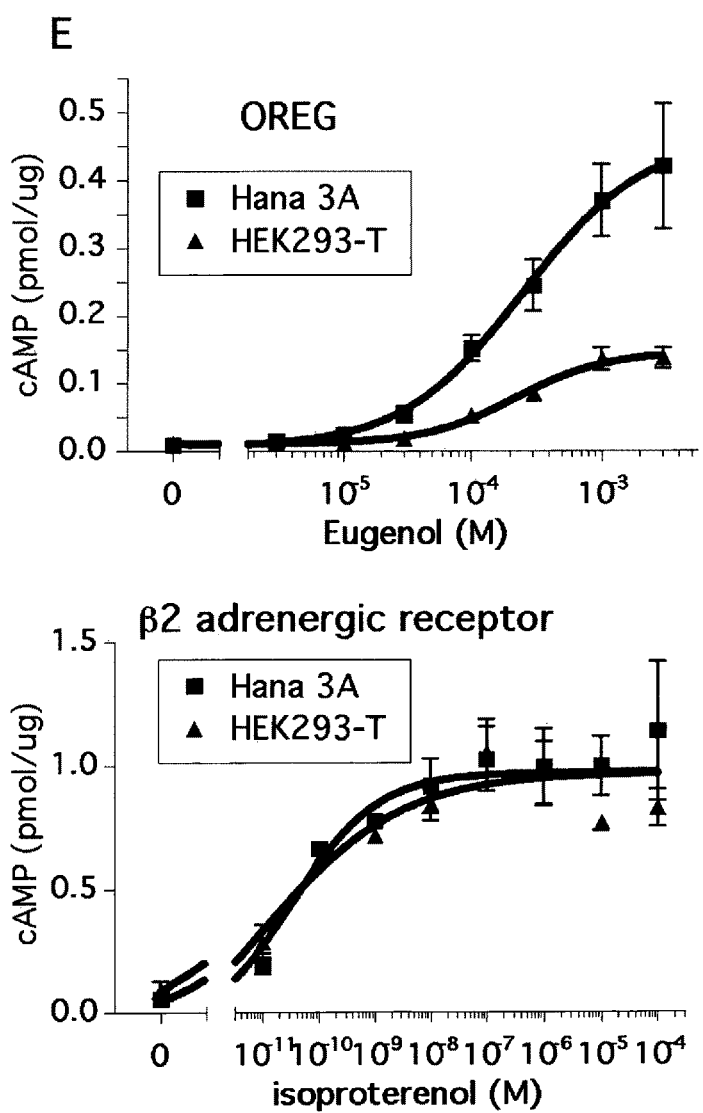

Poor odorant evoked signaling activity in heterologous cell culture systems expressing ORs has been attributed to the poor cell surface expression of ORs. The identification of REEP and/or RTP allowed a direct assessment of this issue. A luciferase reporter gene assay was employed in which a cAMP responsive element (CRE) mediated luciferase gene expression (see FIG. 8A). Because OR activation leads to an increase in cAMP, activation of the mouse odorant receptor OREG by its ligand eugenol was measured in the presence and absence of REEP and/or RTP (see, e.g., Kajiya, K., et al. (2001) J Neurosci 21, 6018-6025; Touhara, K., et al., (1999) Proc Natl Acad Sci USA 96, 4040-4045; each herein incorporated by reference in their entireties). As reported previously, eugenol increased levels of OREG dependent luciferase activity (see, e.g., Katada, S., et al. (2003) Biochem Biophys Res Commun 305, 964-969; herein incorporated by reference in its entirety). Co-expression of OREG with REEP and/or RTP markedly enhanced odorant-dependent luciferase activity (FIG. 8B). Similar results were obtained when vanillin or ethyl vanillin, two other OREG ligands were applied. Since RTP4 is also expressed at low levels in olfactory epithelium, this protein was co-expressed with OREG, but this did not produce a significant increase in luciferase reporter gene activity.

Other GPCRs can exhibit change in ligand specificity depending on accessory proteins (see, e.g., McLatchie, L. M., et al. (1998) Nature 393, 333-339; herein incorporated by reference in its entirety). (McLatchie et al., 1998). To investigate whether REEP1, RTP1, or RTP2 alter the ligand selectivity of ORs, OREG and OR-S46 with their agonists and related chemicals were tested. No substantial changes in relative chemical selectivity were observed when the receptors were co-expressed with the accessory proteins (see FIG. 8C).

Example 7

Constructing a Functional Assay to Identify Odorant-Receptor Interactions

To facilitate analysis of odorant-OR interactions, 293T cell lines were established which stably express REEP1, RTP1, RTP2 and $G_{\alpha olf}$, the G protein alpha subunit that couples to OR (see, e.g., Belluscio, L., et al. (1998) Neuron 20, 69-81; Jones, D. T., and Reed, R. R. (1989). Science 244, 790-795; each herein incorporated by reference in their entireties). To establish such cells, linearized expression vectors containing mouse REEP1, RTP1, RTP2 and $G_{\alpha olf}$ ORFs were transfected into 293T cells with PGK-Pac (puromycin resistant gene) (see, e.g., Watanabe, S., et al. (1995) Biochem Biophys Res Commun 213, 130-137; herein incorporated by reference in its entirety). Among the puromycin resistant clones, clone 3A showed a large response to eugenol when OREG was transfected, and was named Hana3A. RT-PCR analysis indicated that Hana3A cells express exogenous REEP1, RTP1, RTP2 and $G_{\alpha olf}$ (see FIG. 9). Enhanced cell-surface expression was observed when OREG or other ORs were transfected in Hana3A cells and immunostained (see FIG. 10). To test whether Hana3A cells also increased the ligand response in the luciferase assay, the CRE-luciferase reporter gene along with either OREG (HA-tagged), OR-S46 or OR-S50 were co-transfected and stimulated the cells with their ligands, eugenol, nonanoic acid, and nonanedioic acid, respectively (see, e.g., Malnic, B., et al. (1999) Cell 96, 713-723; Touhara, K., et al. (1999) Proc Natl Acad Sci USA 96, 4040-4045; each herein incorporated by reference in their entireties). Little luciferase induction was observed when HA-OREG was expressed in 293T cells. In contrast, when Hana3A cells were used, an enhancement in luciferase activity was observed following eugenol stimulation (see FIG. 8D). Similar results were obtained using two additional ORs, OR-S46 and OR-S50. The OR-S50 gene did not produce a luciferase response in 293T cells, whereas the same receptor transfected into the Hana3A cells produced robust luciferase activity (see FIG. 8D). Expression of $G_{\alpha olf}$ alone in 293T cells had little or no effect on OR activation using this assay.

In order to confirm the increased OR function in the presence of REEP1, RTP1 and RTP2, the amount of cAMP upon ligand stimulation was measured using 293T cells expressing $G_{\alpha olf}$ and Hana3A cells. When OREG was transfected and eugenol was added to stimulate the OR, more cAMP was produced in Hana3A cells. In contrast, when the β2 adrenergic receptor was expressed and isoproterenol was used, no significant differences in cAMP production were observed (see FIG. 8E). The present invention is not limited to a particular mechanism. Indeed, an understanding of the mechanism is not necessary to practice the present invention. Nonetheless, this further supports a specific role of the accessory proteins in functional OR expression.

Previous studies demonstrated that single olfactory neurons that are activated by aliphatic alcohols and acids express specific ORs, primarily class I (fish-like) ORs (see, e.g., Malnic, B., et al. (1999) Cell 96, 713-723; Zhang, X., and Firestein, S. (2002) Nat Neurosci 5, 124-133; each herein incorporated by reference in their entireties). Four ORs (S6/79, S18, S46 and S50) previously assayed using other techniques (see, e.g., Malnic, B., et al. (1999) Cell 96, 713-723; herein incorporated by reference in its entirety) were tested against an assay panel of aliphatic alcohols, aldehydes and acids and some other odorants. Additionally, five "orphan" class I ORs (MOR23-1, MOR31-4, MOR31-6, MOR32-5 and MOR32-11) whose cognate ligands were unknown were tested. At a suprathreshold concentration of 100 uM, all these ORs were odorant selective, responding to only a small subset of the odorants tested (see FIG. 11A). This specificity was retained at lower, more physiologically relevant concentrations. Many of these ORs responded to odorants present in micromolar concentrations. The cell-surface expression of these ORs by living-cell immunofluorescence were evaluated. Some ORs (S18, MOR31-4, MOR31-6 and MOR32-5) were strongly expressed while other ORs (S6, S50, MOR23-1, MOR32-11) were weakly expressed (see FIG. 12). The present invention is not limited to a particular mechanism. Indeed, an understanding of the mechanism is not necessary to practice the present invention. Nonetheless, these results suggest that weak expression was sufficient to produce a significant response to odorants at physiologically relevant concentrations. Finally, two additional orphan class II ORs, MOR203-1 and olfr62, were tested against a panel of 139 odorants. MOR203-1 responded to high concentrations of nonanoic acid (see FIG. 11B). Olfr62 responded to coumarine and piperonal (see FIG. 11C). Several related aromatic compounds were next tested and 2-coumaranone was identified as a preferred ligand for olfr62 (see FIG. 11C). When parental 293T cells for these ORs were used in this luciferase assay, little or no response to the odorants was observed. The present invention is not limited to a particular mechanism. Indeed, an understanding of the mechanism is not necessary to practice the present invention. Nonetheless, these results further demonstrate the importance of REEP and/or RTP in functional OR expression.

Example 8

REEP and/or RTP Function During Receptor Folding, Transport, and/or Odorant Recognition Expression of GPCRs is a complex process that includes protein folding, post-translational modifications and transport through cellular compartments including the ER and Golgi apparatus. Additionally, evidence indicates that the proper targeting of GPCRs to the plasma membrane may involve homo or heterodimerization (see, e.g., Angers, S., et al. (2002) Annu Rev Pharmacol Toxicol 42, 409-435; herein incorporated by reference in its entirety). The present invention is not limited to a particular mechanism. Indeed, an understanding of the mechanism is not necessary to practice the present invention. Nonetheless, though REEP and/or RTP can function at any of these steps of OR expression, three possibilities are presented in FIG. 13 regarding their possible interaction.

First, REEP and/or RTP promote correct folding of ORs in the ER. NinaA, a cyclophilin homolog of *Drosophila*, was identified as a chaperone protein for rhodopsin and thought to facilitate the correct folding (see, e.g., Baker, E. K., et al. (1994) Embo J 13, 4886-4895; Shieh, B. H., et al. (1989) Nature 338, 67-70; each herein incorporated by reference in their entireties). The plant homologs of REEP1, HVA22s, are stress-induced genes and may allow plants to tolerate adverse conditions (see, e.g., Chen, C. N., et al. (2002) Plant Mol Biol 49, 633-644; Shen, Q., et al. (1993) J Biol Chem 268, 23652-23660; each herein incorporated by reference in their entireties). The present invention is not limited to a particular mechanism. Indeed, an understanding of the mechanism is not necessary to practice the present invention. Nonetheless, while the precise roles of HVA22s are not known, since a number of stress induced proteins, such as heat shock proteins, function as chaperones, it is conceivable that HVA22s and, by analogy, perhaps REEP1 act as chaperones to promote folding.

Second, REEP1, RTP1, and RTP2 facilitate the transport of specific vesicles/cargos that include ORs. Consistent with this idea, a REEP1 homolog in yeast, YOP1P, has been implicated in Rab-mediated vesicle transport (see, e.g., Brands, A., and Ho, T. H. (2002) Plant Physiol 130, 1121-1131; Calero, M. (2001) J Biol Chem 276, 12100-12112; each herein incorporated by reference in their entireties). In *C. elegans*, a clathrin adaptor subunit, UNC-101, mediates trafficking of chemosensory receptors to olfactory cilia (see, e.g., Dwyer, N. D., et al., (2001) Neuron 31, 277-287; herein incorporated by reference in its entirety).

Figure 7:
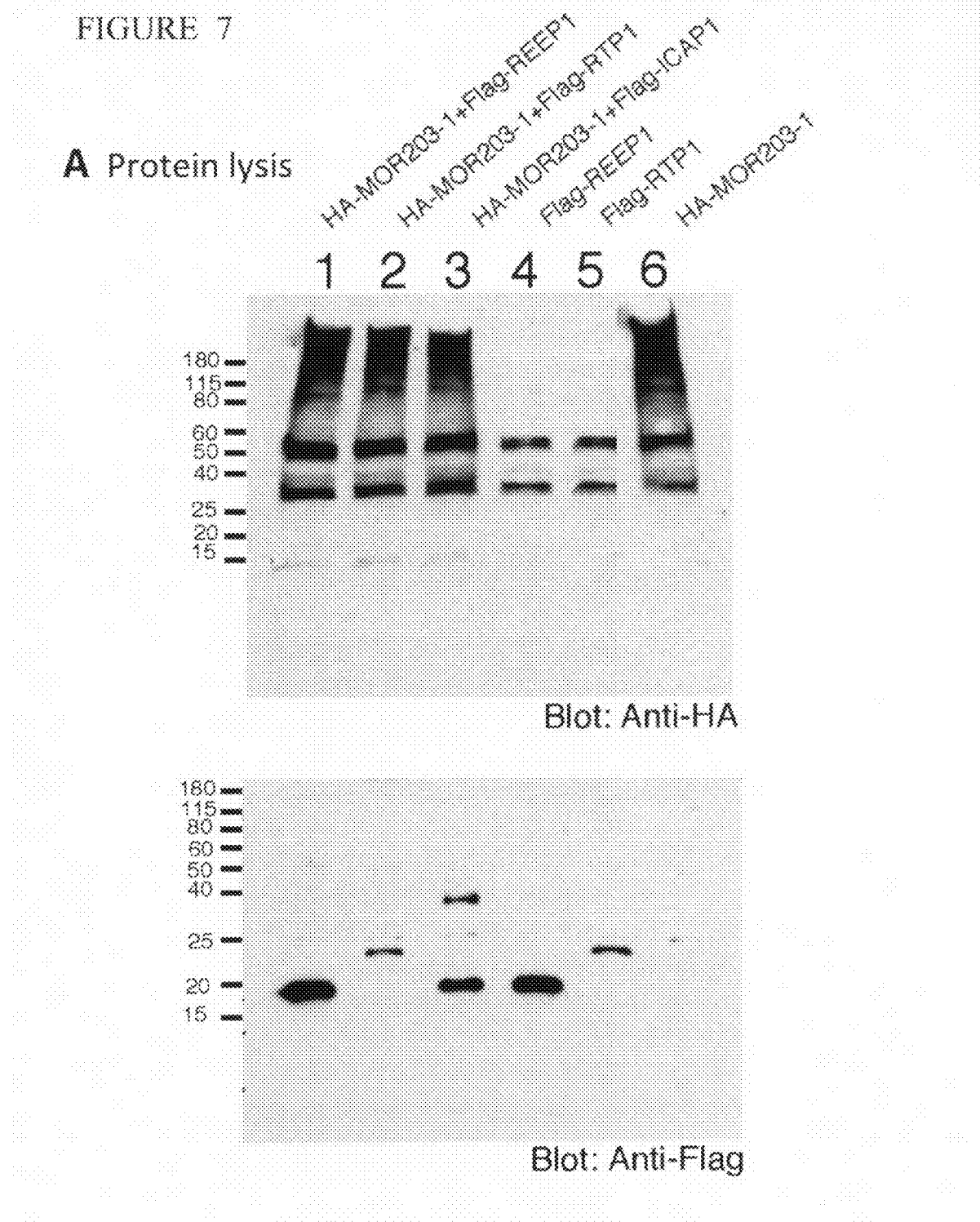
FIG. 7 shows association of odorant Receptors with REEP1 and RTP1. (A) Control western blot analysis indicating expression of HA-tagged MOR203-1, Flag-tagged REEP1, RTP1 and ICAP1 in 293T cells. (B) When Flag-RTP1 or Flag-REEP1 was precipitated, HA-MOR203-1 proteins were co-precipitated (Lanes 1 and 2). However, when Flag-ICAP-1 (a negative control protein) was precipitated, HA-MOR203-1 proteins were not detected (Lane 3). (C) When HA-MOR203-1 was precipitated, Flag-REEP1 and Flag-RTP1 were co-purified when co-expressed (Lanes 1 and 2). Negative control protein (Flag-ICAP-1) was not co-precipitated (Lane 3). Asterisks indicate nonspecific Ig proteins. (D) Little cell-surface expression was observed when RTP1 was transfected in 293T cells. However, when RTP1 and an odorant receptor (OREG) were co-transfected, more RTP1 staining signal was observed. (E) A small amount of cell-surface signal was observed when REEP1 was transfected in 293T cells. Co expression of an OR (olfr62) did not change the expression of REEP1. Scale bars equal to 50 um.
Figure 7:
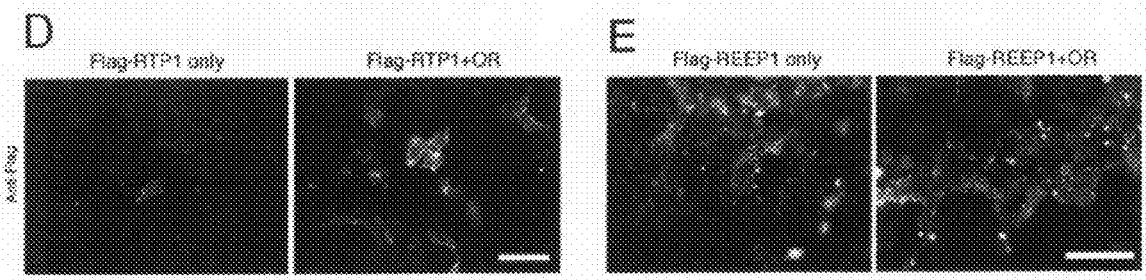

Third, REEP1, RTP1, and RTP2 act as a co-receptor with ORs. As shown in FIG. 7D, RTP1 cell surface expression is enhanced by co-expression of ORs. ORs may contain ER retention signal(s) that are masked by the association with RTPs (or REEP1), a mechanism similar to the regulation of cell-surface expression of GABA(B)R1 receptor by the association of GABA(B)R2 (see, e.g., Jones, K. A., et al. (1998) Nature 396, 674-679; Kaupmann, K., et al. (1998) Nature 396, 683-687; White, J. H., et al. (1998) Nature 396, 679-682; each herein incorporated by reference in their entireties). The REEPs and RTPs may have different or complementary roles, a hypothesis that is consistent with the absence of any amino acid sequence similarity or specific sequence motifs.

The present invention is not limited to a particular mechanism. Indeed, an understanding of the mechanism is not necessary to practice the present invention. Nonetheless, the three roles outlined above are reasonable for REEP1, RTP1 and RTP2; however, other possible functions are not excluded. Even though changes in ligand specificity of OREG or OR-S46 was not observed when expressed with REEP1, RTP1 or RTP2, it is possible that they do play a role in modulating recognition profiles of some ORs. For example, different RAMP members change the ligand specificity of calcitonin receptor like receptor (CRLR), a member of GPCRs. CRLR expressed with RAMP1 function as a CGRP receptor, whereas CRLR expressed with RAMP2 functions as adrenomedullin receptor (see, e.g., McLatchie, L. M., et al. (1998) Nature 393, 333-339; herein incorporated by reference in its entirety).

The present invention is not limited to a particular mechanism. Indeed, an understanding of the mechanism is not necessary to practice the present invention. Nonetheless, many GPCRs, including V1R pheromone receptors (see, e.g., Dulac, C., and Axel, R. (1995) Cell 83, 195-206; herein incorporated by reference in its entirety), T2R taste receptors (see, e.g., Adler et al. (2000) Cell 100, 693-702; Matsunami, H., Montmayeur, J. P., and Buck, L. B. (2000) Nature 404, 601-604; each herein incorporated by reference in their entireties), the α2C adrenergic receptor (see, e.g., Hurt, C. M., et al. (2000) J Biol Chem 275, 35424-35431; herein incorporated by reference in its entirety), and the thyrotropin-releasing hormone receptor (see, e.g., Yu, R., and Hinkle, P. M. (1997) Mol Pharmacol 51, 785-793; herein incorporated by reference in its entirety), appear to require cofactor(s) for their cell surface expression. Thus, REEP and RTP members may regulate trafficking of such GPCRs. In situ hybridization analysis has shown that REEP3, REEP5, RTP1 and RTP2 are all expressed by the VNO neurons. In addition, REEP members are differentially expressed in subset of brain cells (M.M. and H.M., unpublished observations). The strategy to create a list of genes expressed in specific cell types using SAGE and/or Digital Differential Display and screen genes that promote cell-surface expression of the receptors could be applied in such cases.

Example 9

REEP and/or RTP Enable Investigations of Odorant Receptor-Odorant Interactions

An expression system has been established that permits rapid identification of ligands for ORs. This system was tested with twelve ORs. Four of the tested ORs (S6/S79, S18, S46, and S50) were expressed in single olfactory neurons responding to aliphatic odorants (see, e.g., Malnic, B., et al. (1999) Cell 96, 713-723; herein incorporated by reference in its entirety). The response profiles of OR-S50, but not that of OR-S18 agreed with the previous report (see, e.g., Malnic, B., et al. (1999) Cell 96, 713-723; herein incorporated by reference in its entirety). In previous studies, olfactory neurons S6 and S79 expressed the same OR(OR-S6/S79) and both responded to nonanedioic acid, although only the olfactory neuron S79 responded to two odorants, heptanoic acid and octanoic acid (see, e.g., Malnic, B., et al. (1999) Cell 96, 713-723; herein incorporated by reference in its entirety). In experiments conducted during the course of the present invention, OR-S6/S79 responded to nonanedioic acid but not to heptanoic acid or octanoic acid. The present invention is not limited to a particular mechanism. Indeed, an understanding of the mechanism is not necessary to practice the present invention. Nonetheless, these results support the olfactory neuron S6 response profile. Differences may be due to the variation of responses when recording from single olfactory neurons. When multiple single olfactory neurons that expressed the same OR were recorded against the same set of odorants using calcium imaging, their response profiles were similar but different (see, e.g., Bozza, T., et al. (2002) J Neurosci 22, 3033-3043; herein incorporated by reference in its entirety).

Seven new ORs were identified that responded to different odorants in the test panels. The present invention is not limited to a particular mechanism. Indeed, an understanding of the mechanism is not necessary to practice the present invention. Nonetheless, these results demonstrate the applicability of this system to decode the ligand specificity of ORs. The profiles of the ORs in response to various odorants are consistent with the idea of "combinatorial receptor code" where one OR responds to multiple related odorants and one odorant activates multiple receptors (see, e.g., Kajiya, K., et al. (2001) J Neurosci 21, 6018-6025; Malnic, B., et al. Cell 96, 713-723; each herein incorporated by reference in their entireties).

In experiments conducted during the course of the present invention, not only three class I ORs (S46, MOR23-1, MOR31-4) but also MOR203-1, a class II OR, responded to nonanoic acid. The present invention is not limited to a particular mechanism. Indeed, an understanding of the mechanism is not necessary to practice the present invention. Nonetheless, these results indicate that very different ORs can respond to the same chemical, as MOR203-1 and other nonanoic acid ORs (MOR23-1, MOR31-4 and S46) are only 29-32% identical. Olfr62 is one of the closely related ORs located near or at the IVA locus, implicated in isovaleric acid sensation (see, e.g., Griff, I. C., and Reed, R. R. (1995) Cell 83, 407-414; Zhang, X., and Firestein, S. (2002) Nat Neurosci 5, 124-133; each herein incorporated by reference in their entireties). In experiments conducted during the course of the present invention, olfr62 did not respond to isovaleric acid but responded to coumarin and other related aromatic compounds (see FIG. 11C). Eight other ORs located near the IVA locus were also tested, but none of them responded to isovaleric acid. The present invention is not limited to a particular mechanism. Indeed, an understanding of the mechanism is not necessary to practice the present invention. Nonetheless, these results suggest that these ORs are not involved in isovaleric acid detection.

The present invention is not limited to a particular mechanism. Indeed, an understanding of the mechanism is not necessary to practice the present invention. Nonetheless, the functional OR expression system together with the annotation of virtually all the ORs in the mouse and human genomes (see, e.g., Glusman, G., et al. (2001) Genome Res 11, 685-702; Young, J. M., et al. (2002) Hum Mol Genet 11, 535-546; Zhang, X., and Firestein, S. (2002) Nat Neurosci 5, 124-133; Zozulya, S., et al. (2001) Genome Biol 2, 18; each herein incorporated by reference in their entireties), provide a platform to investigate mammalian OR-odorant interaction in a comprehensive manner.

Example 10

Single-Cell Long SAGE Analysis

Single-cell RT-PCR was conducted as described (see, e.g., Brady, G., and Iscove, N. N. (1993) Methods Enzymol 225, 611-623; Dulac, C., and Axel, R. (1995) Cell 83, 195-206; Matsunami, H., and Buck, L. B. (1997) Cell 90, 775-784; each herein incorporated by reference in their entireties) with modifications. Briefly, adult mouse olfactory tissues were dissociated with dispase (Invitrogen) and collagenase (Invitrogen). Single cells were picked under inverted microscope using micromanipulator and transferred into 4.75 ul of lysis mix (1×PCR buffer (Roche), 1.5 mM $MgCl_2$, 50 uM dNTPs, 200 ng/mg anchor primer (biotin-TATAGAATTCGCGGC-CGCTCGCGA (T) 24), 0.3 U/ul Prime RNase Inhibitor (Eppendorf), and 0.4 U/ul rRNasin (Promega). PCR tubes containing lysed cells were heated to 65 degrees C. for 1 min, cooled at 4 degrees C. and 0.25 ul of RT mix (170 U/ul Superscript II (Invitrogen), 35 U/ul Prime RNase Inhibitor and 45 U/ul rRNasin.) was added and incubated at 37 degrees C. for 10 min then 65 degrees C. for 10 min. 5 ul of TdT mix (1×PCR buffer (Roche), 1.5 mM $MgCl_2$, 3 mM dATP, 1.25 U/ul TdT (Roche), 0.05 U RNase H (Roche)) was added to each tube and incubated at 37 degrees C. for 20 min then at 65 degrees C. for 10 min. 5 ul of the product was added to 50 ul of PCR mix (1×EX Taq buffer (Takara), 0.25 mM dNTPs, 20 ng/ul anchor primer, 2.5 U EX Taq HS polymerase (Takara)) and incubated at 95 degrees C. for 2 min, 37 degrees C. 5 min, 72 degrees C. 20 min, then 28 cycles of 95 degrees C. 30 sec, 67 degrees C. 1 min, 72 degrees C. 6 min plus 6 sec extension for each cycle, then 72 degrees C. for 10 min. Contents of amplified PCR products were analyzed using long SAGE protocols (see, e.g., Saha, S., et al. (2002) Nat Biotechnol 20, 508-512; herein incorporated by reference in its entirety). Briefly, single-cell PCR products were cut with NlaIII (NEB). After biotinylated DNA was bound to streptavidin magnetic beads (Dynal), linkers were ligated. The ligated DNA was cut by MmeI (NEB). The cleaved tags were ligated to form ditags and amplified by PCR. The PCR product was cut with NlaIII and the ditags were ligated to form concatemers. They were ligated into pZero-1 vector (Invitrogen) and transformed. Single colonies were picked and sequenced. Tag sequences were analyzed using SAGE2002 software and NCBI Blast searches.

Example 11

Vector Construction cDNAs were amplified from olfactory epithelium cDNA using HotstarTaq DNA polymerase (Qiagen) or KOD DNA polymerase (Toyobo/Novagen) and subcloned into pCI expression vectors (Promega). OR open reading frames were amplified from genomic DNA of C57BL6 (MOR203-1 and S46), 129 (S18) or DBA2 (olfr62, S6/S79, S50, MOR23-1, MOR31-4, MOR31-6, MOR32-5 and MOR32-11) and subcloned into pCI containing Rho-tag.

Example 12

Cell Culture and Immunocytochemistry 293T cells were maintained in minimal essential medium containing 10% fetal bovine serum (M10). Lipofectamine 2000 (Invitrogen) was used for transfection. In live-cell staining, 16 hours after transfection, cells were incubated in M10 containing anti rhodopsin antibody, 4D2 (see, e.g., Laird, D. W., and Molday, R. S. (1988) Invest Opthalmol V is Sci 29, 419-428; herein incorporated by reference in its entirety) and 15 mM $NaN_3$ at 4 degrees C. for 1 hour. After washing, cells were incubated with Cy3-conjugated anti mouse IgG (Jackson Immunologicals), washed and mounted. For FACS analysis, 4D2 and PE-conjugated anti mouse IgG (Jackson Immunologicals) were used to monitor the Rho tagged receptor expression. Anti HA rabbit antibodies (Sigma) and Alexa 488 conjugated anti rabbit IgG (Molecular Probes) was used to stain the HA-β2 adrenergic receptor. To establish the Hana3a cells, 1 ug/ml of puromycin was used for selection. 96 colonies were picked and assayed using luciferase assay using OREG.

Example 13

Analysis of REEPs and RTPs

For prediction of signal peptide and transmembrane regions of REEPs and RTPs, SignalP (see, e.g., Nielsen, H., et al. (1997) Protein Eng 10, 1-6; herein incorporated by reference in its entirety) was used and TMHMM, respectively. In order to create a phylogenetic tree, ClustalW was used.

Example 14

Northern and In Situ Hybridization

Total RNAs from various tissues were extracted using Trizol reagent (Invitrogen) or Aurum Total RNA (Biorad). RNAs were electrophoresed on formaldehyde-agarose gel and transferred onto HybondN membrane (Amersham). Dig-labeled probes were hybridized to the membrane in Dig easy-hyb solution (Roche) at 65 degrees C. After washing, anti-Dig AP (Roche) were applied and the membranes were washed. The signals were detected with CDP-Star (Roche). The same membrane for all three probes was used. In situ hybridization was performed as described (see, e.g., Matsunami, H., and Buck, L. B. (1997) Cell 90, 775-784; Matsunami, H., et al. (2000) Nature 404, 601-604; Schaeren-Wiemers, N., and Gerfin-Moser, A. (1993) Histochemistry 100, 431-440; each herein incorporated by reference in their entireties). Briefly, Dig-labeled RNA probes were hybridized with fresh frozen sections of three weeks old CD-1 mice. After washing, Dig probes were reacted with anti-Dig AP and signals were detected using NBT-BCIP.

Example 15

Immunoprecipitation 293T cells in 100 mm dishes were transfected with ORs, REEP1, and/or RTP1 cDNAs. 16 hours after transfection, cells were lysed in lysis buffer (50 mM Tris (7.4), 150 mM NaCl, 1% NP-40, 0.5 mM PMSF, 2 mM Benzamidene, 0.5 ug/ml Leupeptin, 1.4 ug/ml pepstatin A, 2.4 ug/ml chymostatin, 15 ug/ml aprotinin, 1 mM sodium orthovanadate). The lysis were incubated with anti-Flag M2 affinity gel (Sigma) or anti-HA affinity matrix (Roche) for 2 hours at 4 degrees C. and washed with lysis buffer. Subsequently, the bound proteins were eluted by incubation with SDS sample buffer at room temperature for 2 hours. SDS-PAGE and western blotting were performed according to Mini-Protean 3 Cell (Bio-Rad) instruction manual. ECL (Amersham) was used for detecting proteins on membranes.

Example 16

Luciferase Assay

Dual-Glo system (Promega) for luciferase assay was used. CRE-Luciferase (Stratagene) was used to measure the receptor activities. *Renilla* luciferase driven by constitutively active SV40 promoter (pRL-SV40: Promega) was used as an internal control. Cells were plated on poly-D-lysine coated 96 well plates (BIOCOAT, Beckton Dickinson). After 8 hours (for experiments shown in FIGS. 8B and 8C) or 12 hours (for experiments shown in FIG. 8D and FIG. 11) after transfection, the medium was replaced with CD293 chemically defined medium (Invitrogen) and the plates were incubated for one hour at 37 degrees C. The medium was replaced with 50 ul of odorant solutions dissolved in CD293 and incubated for 10 hours (for experiments shown in FIGS. 8B and 8C) or 4 hours (for experiments shown in FIG. 8D and FIG. 11) at 37 degrees C. The manufacture's protocol for measuring luciferase and *Renilla* luciferase activities was followed. Luminescence was measured using Wallac Victor 1420 (Perkin-Elmer). Normalized luciferase activity was calculated as [Luc (N)-Luc (0)]/RL (N), where Luc (N)=Luminescent count of a certain well, Luc (0)=Luminescent count without odorant for each OR, and RL (N)=Luminescent count of *Renilla* Luciferase of each well. For cAMP assays, cells were plated onto 24-well plate. OREG or OREG/Golf cDNA was transfected into Hana3a or HEK293-Tcells, respectively. 14 hours after transfection, the cells were incubated in CD293 for 2 hrs, and exposed to eugenol or isoproterenol in MEM containing 10 mM Hepes and 500 uM IBMX for 5 min. cAMP-Screen Direct System (Applied Biosystems) was used to measure the cAMP levels. Prism software (Graphpad) was used for data analysis.

Example 17

Chemicals

All odorants were purchased from Sigma except octanoic acid from Calbiochem. The chemicals used in finding cognate ligands for MOR203-1 and olfr62 are provided in Example 19.

Example 18

Genbank Accession Numbers

The genbank accession numbers of mouse REEP1-6 and RTP1-4 and the genbank accession numbers of human REEP1-6 and RTP1-A1, RTP2, RTP3, and RTP4: AY562225-AY562244.

Example 19

Supplemental Materials

Chemicals that are used for initial ligand screening for MOR203-1 and olfr62 are the following: 1 (+)-Carvone, 2

L-Canvone, 3 (−)-Fenchone, 4 Citral, 5 (1R)-(−)-Fenchone, 6 (+)-Fenchone, 7 Rosemary oil, 8 (−)-Rose oxide, 9 (+)-Rose oxide, 10 (−)-Camphor, 11 (S)-(−)-Limonene, 12 (R)-(+)-1-Phenylethanol, 13 (S)-(+)-2-Phenylbutyric acid, 14 (R)-(−)-2-Phenylbutyric acid, 15 2-Hexanone, 16 1-Pentanol, 17 1-Heptanol, 18 (±)-2-Butanol, 19 1-propanol, 20 1-Hexanol, 21 (−)-Menthol, 22 (R)-(−)-2-Heptanol, 23 (−)-α-Terpineol, 24 (+)-Menthol, 25 2-methyl-2-heptanol, 26 (S)-(+)-2-Octanol, 27 (S)-(+)-2-Butanol, 28 (S)-(+)-2-Heptanol, 29 (R)-(−)-2-Octanol or P(+)-2 Octanol, 30 1-Decanol, 31 (−)-β-Citronellol, 32 (S)-(−)-1-Phenylethanol, 33 Propionaldehyde, 34 Undecanal, 35 Octanal (Caprylic aldehyde), 36 trans-Cinnamaldehyde, 37 Nonanal (Pelargonaldehyde), 38 Heptaldehyde, 39 Decanal, 40 Hexanoic acid, 41 Hexanoic acid, 42 Heptanoic acid (Oenanthic acid), 43 Pentanoic acid, 44 Propionic acid, 45 Butyric acid, 46 Nonanoic acid, 47 Methyl propionate, 48 Ethyl butyrate, 49 Butyl butyrate, 50 tert-Butyl propionate, 51 Methyl butyrate, 52 Propyl butyrate, 53 Pentyl acetate, 54 Dimethylpyrazine, 55 Isobutylamine, 56 Geraniol, 57 2-Pentanone, 58 2-Butanone, 59 (1S)-(−)-α-Pinene, 60 1,4-Cineole, 61 Phenetole, 62 Butyl methyl ether, 63 (R)-(+)-Pulegone, 64 Benzene, 65 Benzyl alcohol, 66 Guaiacol, 67 Isopentylamine, 68 g-Caprolactone, 69 g-Caprolactone, 70 octen, 71 Allyl heptanoate, 72 a-Amylcinnamaldehyde, 73 Amyl hexanoate, 74 amylbutyrate, 75 Anethole, 76 Anisaldehyde, 77 Benzophenone, 78 Benzyl acetate, 79 Benzyl salicylate, 80 Butyl heptanoate, 81 camphor ((+)-Camphor), 82 Cedryl acetate, 83 Cinnamyl alcohol, 84 Cinnamaldehyde, 85 (R)-(+)-Citronellal, 86 (S)-(−)-Citronellal, 87 citronellol, 88 Coumarin, 89 Cyclohexanone, 90 p-cymene, 91 5,5-Dimethyl-1,3-cyclohexanedione (Dimedone), 92 ethylamylketone (3-Octanone), 93 Eucalyptol, 94 Heptyl isobutyrate, 95 Hexyl acetate, 96 a-Hexylcinnamaldehyde, 97 Isobornyl acetate, 98 Linalool, 99 Lyral (a-Amylcinnamaldehyde dimethyl acetal), 100 Hydroxycitronellal, 101 p-Tolyl isobutyrate, 102 o-Tolyl isobutyrate, 103 p-Tolyl phenylacetate, 104 2-Methoxy-3-Methyl-pyrazine, 105 2-Methoxypyrazine, 106 Methyl salicylate, 107 Myrcene, 108 w-Pentadecalactone, 109 prenylacetate, 110 2-Phenylethanol, 111 2-Phenethyl acetate, 112 Piperonal, 113 Pyrazine, 114 Sassafras oil, 115 thymol, 116 Triethylamine, 117 2-Heptanone, 118 Methyl eugenol, 119 eugenol, 120 Eugenol methyl ether, 121 Butyraldehyde, 122 Hexanal, 123 1-Pentanol, 124 valeraldehyde, 125 Azelaic acid dichloride, 126 Azelaic acid, 127 Isovaleric acid, 128 Decanoic acid, 129 Vanillic acid, 130 1-Octanol, 131 4-Ethylphenol, 132 Heptaldehyde, 133 1-Nonanol, 134 Nonanal, 135 Ethyl vanillin, 136 Vanillin, 137 Acetophenone, 138 2-Ethylphenol, 139 Octanal.

Chemicals related to coumarin and piperonal (used for olfr62) are the following: 140 Benzaldehyde, 141 Piperonyl alcohol, 142 4-Hydroxycoumarin, 143 4-Chromanone, 144 2-Coumaranone.

Example 20

Activation Patterns of Human Odorant Receptors

Hana3A cells (293T cells expressing mouse REEP1, RTP1, RTP2, and $G_{\alpha olf}$) were used. CRE-Luciferase (Stratagene) was used to measure odorant receptor activities. The following human odorant receptors were tested for expression patterns in response to various odiferous agents: 36, 35, 11, 57, 58, 9, 3, 42, 81, 82, 66, 13, 87, 33, 44, 43, 77, 75, 64, 59, 12, 62, 60, 120, 90, 95, 160, and 106. The following odiferous agents were used to test human odorant receptor expression patterns: Pyridine, 2,2'-(Dithiodimethylene)difuran, 1-Decanol, 1-Hexanol, (−)-Fenchone, (+)-Fenchone, Geraniol, 2-Pentanone, Benzyl salicylate, (+)-Menthol, (−)-Menthol, Benzene, Undecanal, Methyl butylate, Heptyl isobutyrate, p-Tolyl isobutyrate, amylbutyrate, Ethyl butyrate, Hexyl acetate, Pentyl Acetate, Piperonyl acetate, (−)-b-Citronellol, citronellol, Eugenol methyl ether, Methyl Eugenol, a-Amylcinnamaldehyde, a-Amylcinnamaldehyde dimethyl acetal, Cinnamaldehyde, a-Hexylcinnamaldehyde, Hydroxycitronnellal, Citral, (R)-(+)-Citronellal, (S)-(−)-Citronellal, p-Toly phenylacetate, Allyl phenylacetate, Propionic acid, Azelaic acid dichloride, isovaleric acid, (R)-(−)-2-Phenylbutyric acid, (S)-(+)-2-Phenylbutyric acid, Heptanoic Acid, Octanoic Acid, Valeric Acid, Hexanoic Acid, and Butyl butyrate. *Renilla* luciferase driven by constitutively active SV40 promoter (pRL-SV40: Promega) was used as an internal control. Dual-Glo system (Promega) was used for the luciferase assay. Cells were plated on poly-D-lysine coated 96 well plates (BIOCOAT, Beckton Dickinson). 12-16 hours after transfection, the medium was replaced with CD293 chemically defined medium (Invitrogen) and the plates were incubated for one hour at 37 degrees C. The medium was replaced with 50 µl of odorant solutions dissolved in CD293 and incubated for 4 hours at 37 degrees C. The manufacture's protocol was followed for measuring luciferase and *Renilla* luciferase activities. Luminescence was measured using Wallac Victor 1420 (Perkin-Elmer). Normalized luciferase activity was calculated as [Luc (N)-Luc (0)]/RL (N), where Luc (N)=Luminescent count of a certain well, Luc (0)=Luminescent count without odorant for each OR, and RL (N)=Luminescent count of *Renilla* Luciferase of each well. FIG. 34 shows the activation patterns of the human odorant receptors in response to odiferous agent exposure.

Example 21

Cell-Surface Expression of V1RE11 in Hana3A and 293T Cells cDNAs encoding a putative pheromone receptor (V1RE11) were transfected into Hana3A cells (HEK293T cells expressing REEP1, RTP1, RTP2 and $G_{\alpha olf}$) or 293T cells. V1RE11 is a putative pheromone receptor in the mouse and is completely different from odorant receptors in amino acid sequences. Hana3A cells supported cell-surface expression of V1RE11. The present invention is not limited to a particular mechanism. Indeed, an understanding of the mechanism is not necessary to practice the present invention. Nonetheless, these results indicate that REEP1, RTP1, and RTP2 can support functional expression of receptors other than odorant receptors.

Example 22

The Ability of RTP1-A, RTP1-B, RTP1-C, RTP1-D and RTP1-E to Enhance OLFR62 Cell-Surface Expression and Activity This example describes the generation of the RTP1 variants RTP1-A, RTP1-B, RTP1-C, RTP1-D and RTP1-E and their ability to enhance OLFR62 cell-surface expression and activity. Variants of RTP1 were generated by deleting portions of RTP1. FIG. 35 schematically shows the amino acid segments of RTP1-A, RTP1-B, RTP1-C, RTP1-D, and RTP1-E in comparison to RTP1. pCI was a control vector. FIG. 36 shows the murine amino acid sequence for RTP1-A (SEQ ID NO: 41), FIG. 37 shows the murine amino acid sequence for RTP1-B (SEQ ID NO: 42), FIG. 38 shows the murine amino acid sequence for RTP1-C (SEQ ID NO: 43), FIG. 39 shows the murine amino acid sequence for RTP1-D (SEQ ID NO: 44), and FIG. 40 shows the murine amino acid sequence for RTP1-E (SEQ ID NO: 45).

FIG. 41 shows cell-surface expression of OLFR62 in Hana3A and 293T cells. cDNAs encoding RTP1, RTP1-A, RTP1-B, RTP1-C, RTP1-D, RTP1-E, and control pCI were transfected into Hana3A cells or 293T cells. Increased cell-surface staining was seen in Hana3A cells and 239T cells expressing RTP1-D.

FIG. 42 schematically shows a luciferase assay used to monitor the activity of OLFR62 activity. cAMP responsive element (CRE) and luciferase was used to monitor activation of OLFR62. Activation of OLFR62 increases cAMP, which enhances the expression of luciferase reporter gene through the CRE.

FIG. 43 shows OLFR62 activity as indicated by luciferase expression in Hana3A cells and 293T cells expressing RTP1, RTP1-A, RTP1-B, RTP1-C, RTP1-D, RTP1-E, and control pCI. Increased enhancement of OLFR62 activity was seen in 293T cells and Hana3A cells expressing RTP1-D.

Example 23

The Ability of RTP1-A1, RTP1-D1, RTP1-D2, and RTP1-D3 to Enhance OLFR62 Cell-Surface Expression and Activity This example describes the generation of the RTP1 variants RTP1-A1, RTP1-D1, RTP1-D2, and RTP1-D3 and their ability to enhance OLFR62 cell-surface expression and activity. Variants of RTP1 were generated by deleting portions of RTP1-A and RTP1-D. In particular, primer pairs were laid down at specific locations corresponding to desired deletion segments and were amplified by PCR with KOD polymerase. FIG. 44 schematically shows the amino acid segments of RTP1-A1, RTP1-D1, RTP1-D2, and RTP1-D3 in comparison to RTP1-A and RTP1-D, respectively. FIG. 45 shows the murine amino acid sequence for RTP1-A1 (SEQ ID NO: 46) and the human amino acid sequence for RTP1-A1 (SEQ ID NO: 47). FIG. 46 shows the murine amino acid sequence for RTP1-D1 (SEQ ID NO: 48). FIG. 47 shows the murine amino acid sequence for RTP-D2 (SEQ ID NO: 49). FIG. 48 shows the murine amino acid sequence for RTP-D3 (SEQ ID NO: 50).

FIG. 49 shows cell-surface expression of OLFR62 in 293T cells. cDNAs encoding RTP1, RTP1-A1, RTP1-D1, RTP1-D2, and RTP1-D3, and control pCI were transfected into 293T cells. Increased cell-surface staining was seen in 239T cells expressing RTP1-A1, RTP1-D1 and RTP1-D3.

FIG. 50 shows OLFR62, OREG, S6, and 23-1 activity as indicated by luciferase expression in 293T cells expressing RTP1, RTP1-A1, RTP1-D1, RTP1-D2, and RTP1-D3, and control pCI. Increased enhancement of OLFR62, OREG, S6, and 23-1 activity was seen in 293T cells expressing RTP1-A1.

FIG. 51 shows OLFR62, OREG, S6, and 23-1 activity as indicated by luciferase expression in Hana3A cells expressing RTP1, RTP1-A1, RTP1-D1, RTP1-D2, and RTP1-D3, and control pCI.

FIG. 52 shows cell-surface expression of OLFR62, OREG, MOR203-1, S6, and 23-1 in 293T cells co-transfected with either RTP1, RTP1-A1 or control pCI. cDNAs encoding RTP1, RTP1-A1, and control pCI were transfected into cells. Increased cell-surface staining was seen in cells expressing RTP1-A1.

Example 24

RTP1 and RTP4 Chimeras

This example describes RTP1 and RTP4 chimeras generated with chimeric PCR. In particular, complex chimera primers were designed at the connection points of the RTP1 and RTP4 sequences. For each chimera, two pairs of primers were first amplified (e.g., forward primer and complex primer, complex primer and reverse primer). Next, the two PCR products were used as templates in a subsequent megaprimer PCR, with the original forward and reverse primers, to obtain a desired chimera. FIG. 53 schematically shows the amino acid segments of RTP1-A1-A (Chimera 1), RTP1-A1-D2 (Chimera 2), RTP1-A1-D1 (Chimera 3), RTP4-A1-A (Chimera 4), RTP14-A1-D2 (Chimera 5), and RTP4-A1-D1 (Chimera 6).

FIG. 54 shows cell-surface expression of an OR in cells expressing RTP1, RTP4, Chimera 1, Chimera 2, Chimera 3, Chimera 4, Chimera 5, Chimera 6, and control pCI. cDNAs encoding RTP1, RTP4, RTP1-A1, Chimera 1, Chimera 2, Chimera 3, Chimera 4, Chimera 5, Chimera 6, and control pCI were transfected into 293T cells.

FIG. 55 shows OLFR62, OREG, S6, and 23-1 activity as indicated by luciferase expression in 293T cells expressing RTP1, RTP4, RTP1-A1, RTP1-D1, RTP1-D2, Chimera 1, Chimera 2, Chimera 3, Chimera 4, Chimera 5, Chimera 6, and control pCI.

FIG. 56 shows detection of RTP1, RTP1-A, RTP1-B, RTP1-C, RTP1-A1, RTP1-D, Chimera 4, Chimera 5, RTP1-D3, RTP1-D1, Chimera 6, and RTP4 using anti-RTP1.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for identifying an odorant receptor ligand, comprising:
   a) providing
      i) a cell comprising an odorant receptor, wherein said cell further comprises a heterologous nucleic acid encoding a polypeptide comprising an amino acid sequence that is at least 80% identical to SEQ ID NO: 33 and/or 37, wherein said polypeptide is capable of promoting odorant receptor cell surface localization and odorant receptor functional expression, and
      ii) a test compound;
   b) exposing said test compound to said cell in an in vitro setting; and
   c) detecting the activity of said odorant receptor.

2. The method of claim 1, wherein said detecting comprises detecting a reporting agent.

3. The method of claim 1, wherein said odorant receptor is a human odorant receptor.

4. The method of claim 1, wherein said test compound is an odiferous molecule.

5. The method of claim 1, wherein said odorant receptor is a murine odorant receptor.

6. The method of claim 1, wherein said odorant receptor is a synthetic odorant receptor.

7. The method of claim 1, further comprising the step of d) detecting the presence or absence of an odorant receptor ligand based upon said activity.

* * * * *

SEQUENCE LISTING

<160> NUMBER OF SEQ ID NOS: 51

<210> SEQ ID NO 1
<211> LENGTH: 606
<212> TYPE: DNA
<213> ORGANISM: Mus musculus

<400> SEQUENCE: 1

```
atggtgtcgt ggatcatctc caggctggtg gtgcttatat ttggcaccct ttatcctgca       60
tattattcat acaaggctgt gaagtccaag gacattaaag aatatgtcaa atggatgatg      120
tattggatta tatttgccct cttcaccacg gcagagacgt tcacagacat cttcctttgc      180
tggtttccat tctattatga actaaaaata gcgtttgtag cctggctgct gtctccctat      240
acaaaaggat ccagcctcct gtacaggaag tttgttcatc ccacattgtc ttcaaaagaa      300
aaggaaatcg atgactgcct ggtccaagca aaagatcgaa gctatgacgc ccttgtgcac      360
tttgggaagc ggggcttgaa tgtggcagcc actgcagctg tgatggctgc tccaagggac      420
cagggtgcct tgtcagagag actccggagc ttcagcatgc aggacctcac caccatcagg      480
ggtgatggtg ctcctgctcc ctcgggccct cctccaccag ggactgggcg tccagcggc      540 aaacacagcc agcccaagat gtccaggagt gcttctgaga gtgccggcag ctcgggcacc      600
gcctag                                                                606

<210> SEQ ID NO 2
<211> LENGTH: 765
<212> TYPE: DNA
<213> ORGANISM: Mus musculus

<400> SEQUENCE: 2
atggtgtcct ggatcatctc tcgcctggtg gtgctcatct ttggcaccct gtacccagcc       60
tattcttcct acaaggccgt gaagaccaaa aacgtgaagg aatacgtaaa atggatgatg      120
tattggatag tcttcgcctt cttcaccaca gctgagacac ttacagatat aatactgtcc      180
tggttcccct tctactttga gctcaagatt gcctttgtga tatggctgtt gtccccttac      240
accaagggct ccagtgtcct ctaccgcaag ttcgtgcacc caacactgtc caacaaggaa      300
aaggagatcg acgaatacat cacacaagct cgagacaaga gctatgagac gatgatgagg      360
gtgggcaaga ggggcctgaa cctggctgcc aatgctgcag tcacagctgc tgccaagggc      420 caggggggtgc tgtcggaaaa gctgcggagc ttcagcatgc aggacctgac tctcattcga      480
gatgaggatg cgttaccgct gcaggggcca gatggccgcc tccaacccgg ccccgtgggt      540
ctcctggaca ctattgagga cttaggagat gagcctgccc taagtctaag gtctagcaca      600
agccagccag atcccccggac agagacctca gaagatgacc tgggagacaa ggcacccaag      660
aggaccaaac ctatcaaaaa agtacccaga gctgagccgc cggcttccaa gacactgaag      720
acccggccca agaagaagag ttctggaggg ggcgactcag catga                      765

<210> SEQ ID NO 3
<211> LENGTH: 765
<212> TYPE: DNA
<213> ORGANISM: Mus musculus

<400> SEQUENCE: 3
atggtgtcct ggatgatctc ccgagccgtg gtgctggtgt ttggaatgct ctatccagcg       60
tactattcct acaaagccgt gaagacgaaa aacgtcaagg aatacgttcg ctggatgatg      120
tattggatcg tctttgccct ctacactgtc attgaaacgg tggccgatca gacacttgca      180
tggtttcccc tgtactatga gctgaagatt gccttcgtca tttggctgct gtcgccctac      240
actagagggg cgagtttaat ctatagaaag ttccttcatc ccctgctgtc atcaaaggaa      300
agggaaattg atgattatat tgtccaagcc aaagaaagag gctatgagac aatggtgaat      360 tttgacggc aaggtttgaa tttagcagct gcagccgccg tcactgcagc agtgaagagc       420
caaggagcaa taacggagcg tctgcgaagt ttcagcatgc atgatctgac agctatccaa      480
```

```
ggggatgagc ccgtgggaca cagaccctac cagactttgc cagaagcaaa gaggaaaggc    540
aaacaagcca ccgagtcacc agcctatgga attccactga agatggaagt gagcagaca     600 gacgaagaag cggaggggcc attctccgat gacgagatgg tgactcacaa ggcgctgagg    660
cgatcccaga gcatgaaatc tgtcaagacc atcaaggcc gcaaagaggt gcggtatggc     720
tcactaaaat ataaagtgaa gaagagaccg caagtgtatt tttag                    765

<210> SEQ ID NO 4
<211> LENGTH: 774
<212> TYPE: DNA
<213> ORGANISM: Mus musculus

<400> SEQUENCE: 4
atggtgtcct ggatgatctg tcgcctggta gtgctcatat ttggcatgct gtatcctgcg    60
tatgcttcct acaaggccgt gaagagcaag aacattcgag aatatgtacg gtggatgatg   120
tattggattg tctttgcgat cttcatggca gcagaaacct tcacagacat cttcatttcc   180
tggttcccgt tttattacga gttcaagatg gcttttgtgc tgtggctgct ctcaccttac   240
accaaggggg ccagcctgct ttaccgaaag tttgtccacc catccctatc ccgccatgag   300
aaggagatcg acgcgtgtat cgtgcaggca aaggagcgca gctatgaaac catgctcagt   360
tttgggaagc ggagcctcaa catcgctgcc tcagctgctg tgcaggctgc taccaagagt   420
caaggcgctc tagctggaag gctgcggagt ttctctatgc aagacctgcg ctctatccct   480
gacacccctg tccccaccta ccaagatccc ctctacctgg aagaccaggt accccgacgt   540 agaccccta ttggataccg gccaggcggc ctgcagggca gtgacacaga ggatgagtgt    600
tggtcagaca atgagatcgt cccccagcca cctgttcggc cccgagagaa gcctctaggc   660
cgcagccaga gccttcgggt ggtcaagagg aagccattga ctcgagaggg cacctcacgc   720
tccctgaagg tccgaacccg gaaaaaggcc atgccctcag acatggacag ctag         774

<210> SEQ ID NO 5
<211> LENGTH: 570
<212> TYPE: DNA
<213> ORGANISM: Mus musculus

<400> SEQUENCE: 5
atgtccgcag ccatgaggga gaggttcgac cggttcctgc acgagaagaa ctgcatgact    60
gatctcctcg ccaagctcga ggccaagacc ggagtgaacc ggagcttcat cgcgctcggt   120
gtcatcggac tggtggcttt gtatctggtg ttcggttatg gagcctctct cctctgcaac   180
ctgataggtt tcggataccc agcctacatc tcaatgaaag ccatcgagag tcccaacaaa   240
gatgatgaca cccagtggct gacgtactgg gtggtatatg tgtgtgttcag cattgccgaa   300 ttcttctccg atctcttcct gtcctggttc cccttctact acatgctgaa gtgtggcttc   360
ctgctgtggt gcatggcccc cagcccggct aatggggctg agatgcgcta caggcgaatc   420
atccgtccta tcttcctcaa gcacgagtcc caggtagaca gtgtggtgaa ggacgtgaag   480
gacaaagcca aagagactgc agatgccatc agcaaagaag tcaagaaagc tacagtgaac   540
ttgctgggcg atgagaagaa gagcacctga                                    570

<210> SEQ ID NO 6
<211> LENGTH: 606
<212> TYPE: DNA
<213> ORGANISM: Mus musculus
```

```
<400> SEQUENCE: 6
atggacggtc tgcgccagcg cttcgaacgt tttctggaac agaagaacgt ggccaccgaa    60
gcgctcgggg cgctcgaagc aaggaccggt gtagagaagc ggtatctcgc cgcgggagcc   120
ctcgcccttc taggcctgta tcttctgttc ggttacgggg cctctctact gtgcaatgtc   180
atcggatttg tataccccgc atatgcttca gtcaaagcta tcgagagccc aagcaaggaa   240
gacgacactg tgtggctaac ctactgggtg gtgtacgccc tgttcggtct ggtcgaattc   300
ttcagcgatc tactcctgtt ctggttccct ttctactacg cgggcaagtg cgccttcctg   360
ttattttgca tgacgcccgg accctggaac ggggcattac tactatacca tcgcgtcata   420
agaccactct ttctaaagca ccacatggct ctagacagcg ccgcgagcca gctaagcgga   480
agagcattgg acctagcagc tgggataacc cgggacgtac ttcaggcctt ggctcggggc   540
cgggctctcg tcaccccagc atcaacatcg aaccccag ccgctctgga actggacccc    600
aagtaa                                                             606

<210> SEQ ID NO 7
<211> LENGTH: 606
<212> TYPE: DNA
<213> ORGANISM: Homo sapiens

<400> SEQUENCE: 7
atggtgtcat ggatcatctc caggctggtg gtgcttatat ttggcaccct ttaccctgcg    60
tattattcct acaaggctgt gaaatcaaag gacattaagg aatatgtcaa atggatgatg   120
tactggatta tatttgcact tttcaccaca gcagagacat tcacagacat cttcctttgt   180
tggtttccat tctattatga actaaaaata gcatttgtag cctggctgct gtctccctac   240
acaaaaggct ccagcctcct gtacaggaag tttgtacatc ccacactatc ttcaaaagaa   300
aaggaaatcg atgattgtct ggtccaagca aaagaccgaa gttacgatgc ccttgtgcac   360
ttcgggaagc ggggcttgaa cgtggccgcc acagcggctg tgatggctgc ttccaaggga   420
cagggtgcct tatcggagag actgcggagc ttcagcatgc aggacctcac caccatcagg   480
ggagacggcg cccctgctcc ctcgggcccc ccaccaccgg ggtctgggcg ggccagcggc   540
aaacacggcc agcctaagat gtccaggagt gcttctgaga gcgctagcag ctcaggcacc   600
gcctag                                                             606

<210> SEQ ID NO 8
<211> LENGTH: 759
<212> TYPE: DNA
<213> ORGANISM: Homo sapiens

<400> SEQUENCE: 8
atggtgtcct ggatcatctc tcgcctggtg gtgctcatct ttggcaccct gtacccagcc    60
tattcttcct acaaggccgt gaagacaaaa acgtgaagg aatatgtgaa atggatgatg   120
tactggatcg tctttgcctt cttcaccacg gccgagacgc tcacggatat agtgctctcc   180 tggttccct tctactttga actgaagatc gccttcgtga tatggctgct gtccccttac   240
accaagggct ccagcgtgct ctaccgcaag ttcgtgcacc aacgctgtc caacaaggag   300 aaggagatcg acgagtacat cacgcaggcc cgagacaaga gctatgagac catgatgagg   360
gtgggcaaga ggggcctgaa ccttgccgcc aatgctgcag tcacagctgc cgccaagggg   420
gtgctgtcag agaagctccg cagcttcagc atgcaggacc tgaccctgat ccgggacgag   480
gacgcactgc ccctgcagag gcctgacggc cgcctccgac ccagccctgg cagcctcctg   540
```

```
gacaccatcg aggacttagg agatgaccct gccctgagtc taaggtccag cacaaacccg      600
gcagattccc ggacagaggc ttctgaggat gacatgggag acaaagctcc caagagggcc      660
aaacccatca aaaagcgcc caaagctgag ccactggctt ccaagacact gaagacccgg       720
cccaagaaga agacctctgg cgggggcgac tcagcttga                             759

<210> SEQ ID NO 9
<211> LENGTH: 441
<212> TYPE: DNA
<213> ORGANISM: Homo sapiens

<400> SEQUENCE: 9
atggtgtcct ggatgatctc cagagccgtg gtgctggtgt ttggaatgct ttatcctgca      60
tattattcat acaaagctgt gaaaacaaaa acgtgaagg aatatgttcg atggatgatg       120
tactggattg ttttttgctct ctatactgtg attgaaacag tagccgatca acagttgct     180 tggtttcccc tgtactatga gctgaagatt gcttttgtca tatggctgct ttctccctat     240
accaaaggag caagtttaat atatagaaaa ttccttcatc cacttctttc ttcaaaggaa     300
agggagattg atgattatat tgtacaagca aaggaacgag gctatgaaac catggtaaac    360
tttggacggc aaggttttaaa ccttgcagct actgctgctg ttactgcagc agtaaaggta    420
attgttcatt tacctttta a                                                441

<210> SEQ ID NO 10
<211> LENGTH: 774
<212> TYPE: DNA
<213> ORGANISM: Homo sapiens

<400> SEQUENCE: 10
atggtgtcct ggatgatctg tcgcctggtg gtgctggtgt ttgggatgct gtgtccagct      60
tatgcttcct ataaggctgt gaagaccaag aacattcgtg aatatgtgcg gtggatgatg     120
tactggattg ttttttgcact cttcatggca gcagagatcg ttacagacat ttttatctcc    180
tggttccctt tctactatga gatcaagatg gccttcgtgc tgtggctgct ctcaccctac     240
accaagggcg ccagcctgct ttaccgcaag tttgtccacc cgtccctgtc ccgccatgag     300
aaggagatcg acgcgtacat cgtgcaggcc aaggagcgca gctacgagac cgtgctcagc    360
ttcgggaagc ggggcctcaa cattgccgcc tccgctgctg tgcaggctgc caccaagagt    420
caggggggcg tggccggcag gctgcggagc ttctccatgc aggacctgcg ctccatctct    480
gacgcacctg cccctgccta ccatgacccc ctctacctgg aggaccaggt gtcccaccgg    540
aggccaccca ttgggtaccg ggccggggc ctgcaggaca cgacaccga ggatgagtgt       600 tggtcagata ctgaggcagt ccccgggcg ccagcccggc cccgagagaa gccctaatc       660 cgcagccaga gctgcgtgt ggtcaagagg aagccaccgg tgcggaggg cacctcgcgc       720 tccctgaagg ttcggacgag gaaaaagact gtgccctcag acgtggacag ctag            774

<210> SEQ ID NO 11
<211> LENGTH: 570
<212> TYPE: DNA
<213> ORGANISM: Homo sapiens

<400> SEQUENCE: 11
atgtctgcgg ccatgaggga gaggttcgac cggttcctgc acgagaagaa ctgcatgact      60
gaccttctgg ccaagctcga ggccaaaacc ggcgtgaaca ggagcttcat cgctcttggt    120
```

-continued

```
gtcatcggac tggtggcctt gtacctggtg ttcggttatg gagcctctct cctctgcaac      180
ctgataggat ttggctaccc agcctacatc tcaattaaag ctatagagag tcccaacaaa      240
gaagatgata cccagtggct gacctactgg gtagtgtatg gtgtgttcag cattgctgaa      300
ttcttctctg atatcttcct gtcatggttc cccttctact acatgctgaa gtgtggcttc      360
ctgttgtggt gcatgccccc gagcccttct aatggggctg aactgctcta caagcgcatc      420
atccgtcctt tcttcctgaa gcacgagtcc agatgtgaca gtgtggtcaa ggaccttaaa      480
gacaaggcca agagactgc agatgccatc actaagaag cgaagaaagc taccgtgaat        540
ttactgggtg aagaaaagaa gagcacctaa                                       570

<210> SEQ ID NO 12
<211> LENGTH: 555
<212> TYPE: DNA
<213> ORGANISM: Homo sapiens

<400> SEQUENCE: 12
atggacggcc tgaggcagcg cgtggagcac ttcctggagc aaaggaacct ggtcaccgaa       60
gtgctggggg cgctggaggc caagaccggg gtggagaagc ggtatctggc tgcaggagcc      120
gtcactctgc taagcctgta tctgctgttc ggctacggag cgtctctgct gtgcaatctc      180
atcggatttg tgtaccccgc atatgcctca atcaaagcta tcgagagccc aagcaaggac      240
gacgacactg tgtggctcac ctactgggtg gtgtacgccc tgtttgggct ggccgagttc      300
ttcagcgatc tactcctgtc ctggttccct ttctactacg tgggcaagtg cgccttcctg      360
ttgttctgca tggctcccag gccctggaac ggggctctca tgctgtatca gcgcgtcgtg      420
cgtccgctgt tcctaaggca ccacggggcc gtagacagaa tcatgaacga cctcagcggg      480
cgagccctgg acgcggcggc cggaataacc aggaacgtca agccaagcca gaccccgcag      540
ccgaaggaca agtga                                                      555

<210> SEQ ID NO 13
<211> LENGTH: 792
<212> TYPE: DNA
<213> ORGANISM: Mus musculus

<400> SEQUENCE: 13
atgaggattt ttagaccgtg gagactgcgc tgccctgcct tacacttacc ctctttcccc       60
acgttctcta taaagtgtag tttgcctcct cttcccactg acgaagacat gtgtaagagt      120
gtgaccacag gtgagtggaa gaaggtcttc tacgagaaga tggaggaggt gaagccagcg      180
gacagctggg acttcatcat agaccccaac ctcaagcaca atgtgttggc ccctggctgg      240
aagcagtacc tggaacttca tgcctcaggc aggttccact gttcctggtg ctggcacacc      300
tggcagtcac cccatgtagt catcctcttc cacatgtacc tggacaaggc tcagcgcgct      360
ggttcggtgc gcatgcgtgt gttcaagcag ctctgctacg agtgcggtac agcacggctg      420
gatgagtcca gcatgctgga ggagaacatc gaaagcctgg tggacaacct catcaccagt      480
ttgcgagagc agtgctacgg ggagcgtggt ggccactacc gcatccatgt ggccagccgg      540
caggacaacc ggcgacaccg cggagagttc tgcgaggcct gcaggaagg catcgtgcac      600 tggaagccca gtgagaagct gctggaggag gaggcgacca cctacacctt ctcccgtgct      660
cccagcccca ccaaaccgca ggctgaaaca ggctcaggct gcaacttctg ctccattccc      720
tggtgcttat tttgggccac ggttttgatg ctcatcatct acctgcaatt ctccttccgt      780
acttctgtct aa                                                         792
```

<210> SEQ ID NO 14
<211> LENGTH: 672
<212> TYPE: DNA
<213> ORGANISM: Mus musculus

<400> SEQUENCE: 14

```
atgtccacca gcctgaccac ttgtgagtgg aagaaggtct tctacgagaa gatggaggtg      60
gccaagccag cggacagctg ggagctcatc atagacccca ccctcaagcc caatgagctg     120
ggccctggct ggaagcagta cctggagcaa catgcctcag gcaggttcca ctgttcctgg     180
tgttggcaca catggcaatc tgccaatgtc gtcattctct tccacatgca cctggaccgt     240
gcccagcgtg ttggctcagt gcgcatgcgc gtgttcaagc agctgtgcta tcagtgcggc     300
acgtcgcggc tggacgagtc cagcatgctg gaggagaata tcgagggcct ggtggacaac     360
ctcatcacca gtctgcgcga gcagtgttac gatgaggatg gtggccagta ccgcatccac     420
gtagccagcc ggccagacag cggattgcac cgcagtgagt tctgcgaggc ctgccaggaa     480
ggcatcgtgc actggaagcc agcgaaaag ctgctggagg aggatgccgc ctataccgat     540
gcctccaaga agaagggcca ggctggtttt atctccagct tcttctcatt tcgttggtgc     600
ctgttctggg gcaccctctg cctggtcatt gtctacctgc agttcttccg aggccgctct     660
ggcttccttt ag                                                         672
```

<210> SEQ ID NO 15
<211> LENGTH: 1425
<212> TYPE: DNA
<213> ORGANISM: Mus musculus

<400> SEQUENCE: 15

```
atgatggaag aagacatagg agacacagag caatggcgac atgtgttcca ggagctaatg      60
caagaggtga acctggca caatggacc ctcataccag acaagaacct tcttcccaac         120
gttttgaagc caggatggac gcaataccag caaaagacct tgctaggtt ccactgtcct      180
tcctgctctc gaagttgggc atctggccga gttctgatag tcttccacat gcggtggtgt     240
gagaagaagg ccaaggggtg ggtgaagatg agggtgtttg ctcagagatg taatcagtgc     300
cccgagcctc catttgcaac tccagaagtc acttgggaca acatctcaag gatcttgaac     360
aacctgctct tccaaattct gaagaagtgc tataaagaag gatttaagca aatgggtgag     420
attcctttgc tagggaacac cagtctcgaa gggccacatg acagcagcaa ctgtgaggcc     480
tgtctcctgg gcttttgtgc tcagaatgac ttaggccaag cctcaaaacc accagcaccc     540
ccattatctc ctacctcctc aaagtcagcc agggagccca aggtcactgc cacctgtagc     600
aacatttcct cctcacagcc ctcctctaaa gtacagatgc cccaagcatc aaaagcgaac     660
ccccaagcca gtaaccctac caaaaatgac cccaaagtta gctgcacctc aaaaccacca     720
gcaccccat tatctcctac ctccttaaag tcagccaggg agcctaaggt cactgtcacc      780
tgtagcaaca tttcctcctc gcggtcctcc tctaaagtac agatgcccca agcatcaaaa     840
gtgaaccccc aaaccagtaa tcctaccaaa aatgacccca agattagctg tacctcaaaa     900
ccatcaacta ctccaagact gacaatacaa cagctgtcag tagtaagccc acctgcccct     960
gcccctacat gtgtcattca aatgccttct cccactccca tcgacggcag cagagcagca    1020
gatgtagcaa aggagaacac cagatccaag accccaaagg cattgctctc atcccctta    1080
tacgtcccac ccacttcctc ctatgtccca cccacttcct cctatgtccc acccacttcc    1140
```

```
tcctatgtcc cgcccacttc ctcttatgtc ccacccactt cctcctcagt tattgtgccc    1200
atttcctcct cgtggagact accagaaaac actatttgcc aagtagagag aaacagtcat    1260
atccacccgc aaagccagtc ttcctgctgt ggggcctgct gcgagtcctg gtgtgagatc    1320
ttcaggtact catgctgtga ggccgcctgt aattgcatgt cacagagtcc actgtgttgc    1380
ttggcctttc taatcttgtt cttattgctg tggtatttat tataa                   1425

<210> SEQ ID NO 16
<211> LENGTH: 750
<212> TYPE: DNA
<213> ORGANISM: Mus musculus

<400> SEQUENCE: 16
atgctgttcc ccgatgactt cagtacttgg gagcagacat tcaagaact gatgcaggag     60 gagaagcccg ggccaagtg agcctgcat ttggataaga acattgtacc agatggtgca     120
gccctgggat ggaggcagca ccagcagaca gtgcttggca ggttccagtg ttccagatgc    180
tgcagaagtt ggacctctgc tcaggtgatg atcttgtgcc acatgtaccc ggacactttg    240
aaatcgcagg gccaggcacg catgaggatc tttggtcaga agtgccagaa gtgttttgga    300
tgtcaatttg agactcccaa gttctccaca gagatcatca aaagaattct gaataaccta    360
gttaattata ttctgcagag atactatgga cacaggaaga tagcattgac ctcgaatgca    420
tctttgggtg agaaggtgac tttggatggg ccccacgaca cacgcaattg tgaggcatgc    480
agtctaaact ctcatggaag atgtgcccct gcacacaaag taaaaccacc cagatctcca    540
tctccattac caaatagttc ctccccatca aagagctgcc ctcctccgcc tcagacccgg    600
aatacggatt tgggaataaa aactcttcag gattttggga atagaacttt tcagggatgc    660
agagagcccc cccaacgtga aatagagcca ccactatttc tgtttttgtc tattgctgca    720
tttgcccttt ttagtctttt cactagataa                                    750

<210> SEQ ID NO 17
<211> LENGTH: 684
<212> TYPE: DNA
<213> ORGANISM: Homo sapiens

<400> SEQUENCE: 17
atgtgtaaaa gcgtgaccac agatgagtgg aagaaagtct tctatgagaa gatggaggag    60
gcaaagccgg ctgacagctg ggacctcatc atagacccca acctcaagca caatgtgctg    120
agccctggtt ggaagcagta cctggaattg catgcttcag gcaggttcca ctgctcctgg    180
tgctggcaca cctggcagtc gccctacgtg gtcatcctct ccacatgtt cctggaccgc    240 gcccagcggg cgggctcggt gcgcatgcgc gtcttcaagc agctgtgcta tgagtgcggc    300
acggcgcggc tggacgagtc cagcatgctg gaggagaaca tcgagggcct ggtggacaac    360
ctcatcacca gcctgcgcga gcagtgctac ggcgagcgtg gcggccagta ccgcatccac    420
gtggccagcc gccaggacaa ccggcggcac gcgcggagagt tctgcgaggc ctgccaggag    480
ggcatcgtgc actggaagcc cagcgagaag ctgctggagg aggaggcgac cacctacacc    540
ttctcccggg cgcccagccc caccaagtcg caggaccaga cgggctcagg ctggaacttc    600
tgctctatcc cctggtgctt gttttgggcc acggtcctgc tgctgatcat ctacctgcag    660
ttctctttcc gtagctccgt ataa                                          684

<210> SEQ ID NO 18
<211> LENGTH: 678
```

```
<212> TYPE: DNA
<213> ORGANISM: Homo sapiens

<400> SEQUENCE: 18
atgtgtacca gcttgaccac ttgtgagtgg aagaaagtct tctatgagaa gatggaggtg      60
gcaaagccag cggacagctg ggagctcatc atagacccca acctcaagcc cagtgagctg     120
gcccctggct ggaagcagta cctggagcag cacgcctcag gcaggttcca ctgctcctgg     180
tgctggcaca cctggcagtc tgcccatgtg gtcatcctct tccacatgtt cctggaccgc     240
gcccagcggg cgggctcggt gcgcatgcgc gtcttcaagc agctgtgcta tgagtgcggc     300
acggcgcggc tggacgagtc cagcatgctg gaggagaaca tcgagggcct ggtggacaac     360
ctcatcacca gcctgcgcga gcagtgctac gaggaggatg gtggccagta ccgcatccac     420
gtggccagcc gcccggacag cgggccgcat cgtgcagagt tctgtgaggc ctgccaggag     480
ggcatcgttc actggaagcc cagcgagaag ctgctggagg aggaggtgac cacctacacc     540
tctgaagcct ccaagccgag ggcccaggcg ggatccggct acaacttctt gtctcttcgc     600
tggtgcctct tctgggcctc tctctgcctg ctcgttgttt acctgcagtt ctccttcctc     660
agtcctgcct tcttttag                                                  678

<210> SEQ ID NO 19
<211> LENGTH: 699
<212> TYPE: DNA
<213> ORGANISM: Homo sapiens

<400> SEQUENCE: 19
atggctgggg acacagaagt gtggaagcaa atgtttcagg agttaatgcg ggaggtgaag      60
ccatggcaca ggtggaccct gagaccagac aagggccttc ttcccaacgt cctgaagcca     120
ggctggatgc aataccagca gtggaccttc gccaggttcc agtgctcctc ctgctctcgt     180
aactgggcct ctgcccaagt tctggtcctt ttccacatga actggagtga ggagaagtcc     240
aggggccagg tgaagatgag ggtgtttacc cagagatgta agaagtgccc ccaacctctg     300
tttgaggacc ctgagttcac acaagagaac atctcaagga tcctgaaaaa cctggtgttc     360
cgaattctga gaaatgctag gaggaaga tttcagttga tagaggaggt tcctatgatc     420
aaggacatct ctcttgaagg gccacacaat agtgacaact gtgaggcatg tctgcagggc     480
ttctgtgctg ggcccataca ggttacaagc ctccccccat ctcagacccc aagagtacac     540
tccatttaca aggtggagga ggtagttaag ccctgggcct caggagagaa tgtctattcc     600
tacgcatgcc aaaaccacat ctgtaggaac ttaagcattt tctgctgttg tgtcattctc     660
attgttatcg tggtgattgt tgtaaaaact gctatatga                           699

<210> SEQ ID NO 20
<211> LENGTH: 741
<212> TYPE: DNA
<213> ORGANISM: Homo sapiens

<400> SEQUENCE: 20
atggttgtag atttctggac ttgggagcag acatttcaag aactaatcca agaggcaaaa      60 cccgggcca catggacgct gaagttggat ggcaaccttc agctagactg cctggctcaa     120
gggtggaagc aataccaaca gagagcattt ggctggttcc ggtgttcctc ctgccagcga     180
agttgggctt ccgccaagtt gcagattctg tgccacacgt actgggagca ctggacatcc     240
cagggtcagg tgcgtatgag gctctttggc caaaggtgcc agaagtgctc ctggtcccaa     300
```

```
tatgagatgc tgagttctc ctcggatagc accatgagga ttctgagcaa cctggtgcag    360
catatactga agaaatacta tggaaatggc atgaggaagt ctccagaaat gccagtaatc    420
ctggaagtgt ccctggaagg atcccatgac acagccaatt gtgaggcatg cactttgggc    480
atatgtggac agggcttaaa aagctacatg acaaagccgt ccaaatccct actcccccac    540
ctaaagactg ggaattcctc acctggaatt ggtgctgtgt acctcgcaaa ccaagccaag    600
aaccagtcag atgaggcaaa agaggctaag gggagtgggt atgagaaatt agggcccagt    660
cgagacccag atccactgaa catctgtgtc tttatttttgc tgcttgtatt tattgtagtc    720 aaatgctttta catcagaatg a                                              741
```

```
<210> SEQ ID NO 21
<211> LENGTH: 201
<212> TYPE: PRT
<213> ORGANISM: Mus musculus

<400> SEQUENCE: 21

Met Val Ser Trp Ile Ile Ser Arg Leu Val Val Leu Ile Phe Gly Thr
1               5                   10                  15

Leu Tyr Pro Ala Tyr Tyr Ser Tyr Lys Ala Val Lys Ser Lys Asp Ile
                20                  25                  30

Lys Glu Tyr Val Lys Trp Met Met Tyr Trp Ile Ile Phe Ala Leu Phe
            35                  40                  45

Thr Thr Ala Glu Thr Phe Thr Asp Ile Phe Leu Cys Trp Phe Pro Phe
        50                  55                  60

Tyr Tyr Glu Leu Lys Ile Ala Phe Val Ala Trp Leu Leu Ser Pro Tyr
65                  70                  75                  80

Thr Lys Gly Ser Ser Leu Leu Tyr Arg Lys Phe Val His Pro Thr Leu
                85                  90                  95

Ser Ser Lys Glu Lys Glu Ile Asp Asp Cys Leu Val Gln Ala Lys Asp
            100                 105                 110

Arg Ser Tyr Asp Ala Leu Val His Phe Gly Lys Arg Gly Leu Asn Val
        115                 120                 125

Ala Ala Thr Ala Ala Val Met Ala Ala Ser Lys Gly Gln Gly Ala Leu
    130                 135                 140

Ser Glu Arg Leu Arg Ser Phe Ser Met Gln Asp Leu Thr Thr Ile Arg
145                 150                 155                 160

Gly Asp Gly Ala Pro Ala Pro Ser Gly Pro Pro Pro Gly Thr Gly
                165                 170                 175

Arg Ser Ser Gly Lys His Ser Gln Pro Lys Met Ser Arg Ser Ala Ser
            180                 185                 190

Glu Ser Ala Gly Ser Ser Gly Thr Ala
        195                 200

<210> SEQ ID NO 22
<211> LENGTH: 254
<212> TYPE: PRT
<213> ORGANISM: Mus musculus

<400> SEQUENCE: 22

Met Val Ser Trp Ile Ile Ser Arg Leu Val Val Leu Ile Phe Gly Thr
1               5                   10                  15

Leu Tyr Pro Ala Tyr Ser Ser Tyr Lys Ala Val Lys Thr Lys Asn Val
                20                  25                  30

Lys Glu Tyr Val Lys Trp Met Met Tyr Trp Ile Val Phe Ala Phe Phe
            35                  40                  45
```

Thr Thr Ala Glu Thr Leu Thr Asp Ile Ile Leu Ser Trp Phe Pro Phe
 50                  55                  60

Tyr Phe Glu Leu Lys Ile Ala Phe Val Ile Trp Leu Leu Ser Pro Tyr
 65                  70                  75                  80

Thr Lys Gly Ser Ser Val Leu Tyr Arg Lys Phe Val His Pro Thr Leu
                 85                  90                  95

Ser Asn Lys Glu Lys Glu Ile Asp Glu Tyr Ile Thr Gln Ala Arg Asp
            100                 105                 110

Lys Ser Tyr Glu Thr Met Met Arg Val Gly Lys Arg Gly Leu Asn Leu
        115                 120                 125

Ala Ala Asn Ala Ala Val Thr Ala Ala Lys Gly Gln Gly Val Leu
    130                 135                 140

Ser Glu Lys Leu Arg Ser Phe Ser Met Gln Asp Leu Thr Leu Ile Arg
145                 150                 155                 160

Asp Glu Asp Ala Leu Pro Leu Gln Gly Pro Asp Gly Arg Leu Gln Pro
                165                 170                 175

Gly Pro Val Gly Leu Leu Asp Thr Ile Glu Asp Leu Gly Asp Glu Pro
            180                 185                 190

Ala Leu Ser Leu Arg Ser Ser Thr Ser Gln Pro Asp Pro Arg Thr Glu
        195                 200                 205

Thr Ser Glu Asp Asp Leu Gly Asp Lys Ala Pro Lys Arg Thr Lys Pro
210                 215                 220

Ile Lys Lys Val Pro Arg Ala Glu Pro Pro Ala Ser Lys Thr Leu Lys
225                 230                 235                 240

Thr Arg Pro Lys Lys Ser Ser Gly Gly Asp Ser Ala
                245                 250

<210> SEQ ID NO 23
<211> LENGTH: 254
<212> TYPE: PRT
<213> ORGANISM: Mus musculus

<400> SEQUENCE: 23

Met Val Ser Trp Met Ile Ser Arg Ala Val Val Leu Val Phe Gly Met
 1               5                  10                  15

Leu Tyr Pro Ala Tyr Tyr Ser Tyr Lys Ala Val Lys Thr Lys Asn Val
                 20                  25                  30

Lys Glu Tyr Val Arg Trp Met Met Tyr Trp Ile Val Phe Ala Leu Tyr
            35                  40                  45

Thr Val Ile Glu Thr Val Ala Asp Gln Thr Leu Ala Trp Phe Pro Leu
 50                  55                  60

Tyr Tyr Glu Leu Lys Ile Ala Phe Val Ile Trp Leu Leu Ser Pro Tyr
 65                  70                  75                  80

Thr Arg Gly Ala Ser Leu Ile Tyr Arg Lys Phe Leu His Pro Leu Leu
                 85                  90                  95

Ser Ser Lys Glu Arg Glu Ile Asp Asp Tyr Ile Val Gln Ala Lys Glu
            100                 105                 110

Arg Gly Tyr Glu Thr Met Val Asn Phe Gly Arg Gln Gly Leu Asn Leu
        115                 120                 125

Ala Ala Ala Ala Ala Val Thr Ala Ala Val Lys Ser Gln Gly Ala Ile
    130                 135                 140

Thr Glu Arg Leu Arg Ser Phe Ser Met His Asp Leu Thr Ala Ile Gln
145                 150                 155                 160

Gly Asp Glu Pro Val Gly His Arg Pro Tyr Gln Thr Leu Pro Glu Ala

```
                    165                 170                 175
Lys Arg Lys Gly Lys Gln Ala Thr Glu Ser Pro Ala Tyr Gly Ile Pro
            180                 185                 190

Leu Lys Asp Gly Ser Glu Gln Thr Asp Glu Glu Ala Glu Gly Pro Phe
        195                 200                 205

Ser Asp Asp Glu Met Val Thr His Lys Ala Leu Arg Arg Ser Gln Ser
    210                 215                 220

Met Lys Ser Val Lys Thr Ile Lys Gly Arg Lys Glu Val Arg Tyr Gly
225                 230                 235                 240

Ser Leu Lys Tyr Lys Val Lys Lys Arg Pro Gln Val Tyr Phe
                245                 250

<210> SEQ ID NO 24
<211> LENGTH: 257
<212> TYPE: PRT
<213> ORGANISM: Mus musculus

<400> SEQUENCE: 24

Met Val Ser Trp Met Ile Cys Arg Leu Val Val Leu Ile Phe Gly Met
1               5                   10                  15

Leu Tyr Pro Ala Tyr Ala Ser Tyr Lys Ala Val Lys Ser Lys Asn Ile
            20                  25                  30

Arg Glu Tyr Val Arg Trp Met Met Tyr Trp Ile Val Phe Ala Ile Phe
        35                  40                  45

Met Ala Ala Glu Thr Phe Thr Asp Ile Phe Ile Ser Trp Phe Pro Phe
    50                  55                  60

Tyr Tyr Glu Phe Lys Met Ala Phe Val Leu Trp Leu Leu Ser Pro Tyr
65                  70                  75                  80

Thr Lys Gly Ala Ser Leu Leu Tyr Arg Lys Phe Val His Pro Ser Leu
                85                  90                  95

Ser Arg His Glu Lys Glu Ile Asp Ala Cys Ile Val Gln Ala Lys Glu
            100                 105                 110

Arg Ser Tyr Glu Thr Met Leu Ser Phe Gly Lys Arg Ser Leu Asn Ile
        115                 120                 125

Ala Ala Ser Ala Ala Val Gln Ala Ala Thr Lys Ser Gln Gly Ala Leu
    130                 135                 140

Ala Gly Arg Leu Arg Ser Phe Ser Met Gln Asp Leu Arg Ser Ile Pro
145                 150                 155                 160

Asp Thr Pro Val Pro Thr Tyr Gln Asp Pro Leu Tyr Leu Glu Asp Gln
                165                 170                 175

Val Pro Arg Arg Arg Pro Ile Gly Tyr Arg Pro Gly Gly Leu Gln
            180                 185                 190

Gly Ser Asp Thr Glu Asp Glu Cys Trp Ser Asp Asn Glu Ile Val Pro
        195                 200                 205

Gln Pro Pro Val Arg Pro Arg Glu Lys Pro Leu Gly Arg Ser Gln Ser
    210                 215                 220

Leu Arg Val Val Lys Arg Lys Pro Leu Thr Arg Glu Gly Thr Ser Arg
225                 230                 235                 240

Ser Leu Lys Val Arg Thr Arg Lys Lys Ala Met Pro Ser Asp Met Asp
                245                 250                 255

Ser

<210> SEQ ID NO 25
<211> LENGTH: 185
<212> TYPE: PRT
```

<213> ORGANISM: Mus musculus

<400> SEQUENCE: 25

```
Met Arg Glu Arg Phe Asp Arg Phe Leu His Glu Lys Asn Cys Met Thr
1               5                   10                  15
Asp Leu Leu Ala Lys Leu Glu Ala Lys Thr Gly Val Asn Arg Ser Phe
            20                  25                  30
Ile Ala Leu Gly Val Ile Gly Leu Val Ala Leu Tyr Leu Val Phe Gly
        35                  40                  45
Tyr Gly Ala Ser Leu Leu Cys Asn Leu Ile Gly Phe Gly Tyr Pro Ala
    50                  55                  60
Tyr Ile Ser Met Lys Ala Ile Glu Ser Pro Asn Lys Asp Asp Asp Thr
65                  70                  75                  80
Gln Trp Leu Thr Tyr Trp Val Val Tyr Gly Val Phe Ser Ile Ala Glu
                85                  90                  95
Phe Phe Ser Asp Leu Phe Leu Ser Trp Leu Pro Phe Tyr Tyr Met Leu
            100                 105                 110
Lys Cys Gly Phe Leu Leu Trp Cys Met Ala Pro Ser Pro Ala Asn Gly
        115                 120                 125
Ala Glu Met Leu Tyr Arg Arg Ile Ile Arg Pro Ile Phe Leu Arg His
    130                 135                 140
Glu Ser Gln Val Asp Ser Val Val Lys Asp Val Lys Lys Ala Lys
145                 150                 155                 160
Glu Thr Ala Asp Ala Ile Ser Lys Glu Val Lys Lys Ala Thr Val Asn
                165                 170                 175
Leu Leu Gly Asp Val Lys Lys Ser Thr
            180                 185
```

<210> SEQ ID NO 26
<211> LENGTH: 201
<212> TYPE: PRT
<213> ORGANISM: Mus musculus

<400> SEQUENCE: 26

```
Met Asp Gly Leu Arg Gln Arg Phe Glu Arg Phe Leu Glu Gln Lys Asn
1               5                   10                  15
Val Ala Thr Glu Ala Leu Gly Ala Leu Glu Ala Arg Thr Gly Val Glu
            20                  25                  30
Lys Arg Tyr Leu Ala Ala Gly Ala Leu Ala Leu Leu Gly Leu Tyr Leu
        35                  40                  45
Leu Phe Gly Tyr Gly Ala Ser Leu Leu Cys Asn Val Ile Gly Phe Val
    50                  55                  60
Tyr Pro Ala Tyr Ala Ser Val Lys Ala Ile Glu Ser Pro Ser Lys Glu
65                  70                  75                  80
Asp Asp Thr Val Trp Leu Thr Tyr Trp Val Val Tyr Ala Leu Phe Gly
                85                  90                  95
Leu Val Glu Phe Phe Ser Asp Leu Leu Leu Phe Trp Phe Pro Phe Tyr
            100                 105                 110
Tyr Ala Gly Lys Cys Ala Phe Leu Leu Phe Cys Met Thr Pro Gly Pro
        115                 120                 125
Trp Asn Gly Ala Leu Leu Leu Tyr His Arg Val Ile Arg Pro Leu Phe
    130                 135                 140
Leu Lys His His Met Ala Leu Asp Ser Ala Ala Ser Gln Leu Ser Gly
145                 150                 155                 160
Arg Ala Leu Asp Leu Ala Ala Gly Ile Thr Arg Asp Val Leu Gln Ala
```

```
                    165                 170                 175
Leu Ala Arg Gly Arg Ala Leu Val Thr Pro Ala Ser Thr Ser Glu Pro
                180                 185                 190

Pro Ala Ala Leu Glu Leu Asp Pro Lys
        195                 200

<210> SEQ ID NO 27
<211> LENGTH: 201
<212> TYPE: PRT
<213> ORGANISM: Homo sapiens

<400> SEQUENCE: 27

Met Val Ser Trp Ile Ile Ser Arg Leu Val Val Leu Ile Phe Gly Thr
1               5                   10                  15

Leu Tyr Pro Ala Tyr Ser Tyr Lys Ala Val Lys Ser Lys Asp Ile
            20                  25                  30

Lys Glu Tyr Val Lys Trp Met Met Tyr Trp Ile Ile Phe Ala Leu Phe
            35                  40                  45

Thr Thr Ala Glu Thr Phe Thr Asp Ile Phe Leu Cys Trp Phe Pro Phe
    50                  55                  60

Tyr Tyr Glu Leu Lys Ile Ala Phe Val Ala Trp Leu Leu Ser Pro Tyr
65                  70                  75                  80

Thr Lys Gly Ser Ser Leu Leu Tyr Arg Lys Phe Val His Pro Thr Leu
                85                  90                  95

Ser Ser Lys Glu Lys Glu Ile Asp Asp Cys Leu Val Gln Ala Lys Asp
            100                 105                 110

Arg Ser Tyr Asp Ala Leu Val His Phe Gly Lys Arg Gly Leu Asn Val
        115                 120                 125

Ala Ala Thr Ala Ala Val Met Ala Ala Ser Lys Gly Gln Gly Ala Leu
    130                 135                 140

Ser Glu Arg Leu Arg Ser Phe Ser Met Gln Asp Leu Thr Thr Ile Arg
145                 150                 155                 160

Gly Asp Gly Ala Pro Ala Pro Ser Gly Pro Pro Pro Gly Ser Gly
                165                 170                 175

Arg Ala Ser Gly Lys His Gly Gln Pro Lys Met Ser Arg Ser Ala Ser
                180                 185                 190

Glu Ser Ala Ser Ser Gly Thr Ala
            195                 200

<210> SEQ ID NO 28
<211> LENGTH: 252
<212> TYPE: PRT
<213> ORGANISM: Homo sapiens

<400> SEQUENCE: 28

Met Val Ser Trp Ile Ile Ser Arg Leu Val Val Leu Ile Phe Gly Thr
1               5                   10                  15

Leu Tyr Pro Ala Tyr Ser Ser Tyr Lys Ala Val Lys Thr Lys Asn Val
            20                  25                  30

Lys Glu Tyr Val Lys Trp Met Met Tyr Trp Ile Val Phe Ala Phe Phe
            35                  40                  45

Thr Thr Ala Glu Thr Leu Thr Asp Ile Val Leu Ser Trp Phe Pro Phe
    50                  55                  60

Tyr Phe Glu Leu Lys Ile Ala Phe Val Ile Trp Leu Leu Ser Pro Tyr
65                  70                  75                  80

Thr Lys Gly Ser Ser Val Leu Tyr Arg Lys Phe Val His Pro Thr Leu
```

```
                85                  90                  95
Ser Asn Lys Glu Lys Glu Ile Asp Glu Tyr Ile Thr Gln Ala Arg Asp
            100                 105                 110

Lys Ser Tyr Glu Thr Met Met Arg Val Gly Lys Arg Gly Leu Asn Leu
            115                 120                 125

Ala Ala Asn Ala Ala Val Thr Ala Ala Lys Gly Val Leu Ser Glu
            130                 135                 140

Lys Leu Arg Ser Phe Ser Met Gln Asp Leu Thr Leu Ile Arg Asp Glu
145                 150                 155                 160

Asp Ala Leu Pro Leu Gln Arg Pro Asp Gly Arg Leu Arg Pro Ser Pro
                165                 170                 175

Gly Ser Leu Leu Asp Thr Ile Glu Asp Leu Gly Asp Pro Ala Leu
                180                 185                 190

Ser Leu Arg Ser Ser Thr Asn Pro Ala Asp Ser Arg Thr Glu Ala Ser
                195                 200                 205

Glu Asp Asp Met Gly Asp Lys Ala Pro Lys Arg Ala Lys Pro Ile Lys
            210                 215                 220

Lys Ala Pro Lys Ala Glu Pro Leu Ala Ser Lys Thr Leu Lys Thr Arg
225                 230                 235                 240

Pro Lys Lys Lys Thr Ser Gly Gly Asp Ser Ala
                245                 250
```

<210> SEQ ID NO 29
<211> LENGTH: 146
<212> TYPE: PRT
<213> ORGANISM: Homo sapiens

<400> SEQUENCE: 29

```
Met Val Ser Trp Met Ile Ser Arg Ala Val Leu Val Phe Gly Met
1               5                  10                  15

Leu Tyr Pro Ala Tyr Tyr Ser Tyr Lys Ala Val Lys Thr Lys Asn Val
                20                  25                  30

Lys Glu Tyr Val Arg Trp Met Met Tyr Trp Ile Val Phe Ala Leu Tyr
            35                  40                  45

Thr Val Ile Glu Thr Val Ala Asp Gln Thr Val Ala Trp Phe Pro Leu
    50                  55                  60

Tyr Tyr Glu Leu Lys Ile Ala Phe Val Ile Trp Leu Leu Ser Pro Tyr
65                  70                  75                  80

Thr Lys Gly Ala Ser Leu Ile Tyr Arg Lys Phe Leu His Pro Leu Leu
                85                  90                  95

Ser Ser Lys Glu Arg Glu Ile Asp Asp Tyr Ile Val Gln Ala Lys Glu
            100                 105                 110

Arg Gly Tyr Glu Thr Met Val Asn Phe Gly Arg Gln Gly Leu Asn Leu
            115                 120                 125

Ala Ala Thr Ala Ala Val Thr Ala Ala Val Lys Val Ile His Leu
                130                 135                 140

Pro Phe
145
```

<210> SEQ ID NO 30
<211> LENGTH: 257
<212> TYPE: PRT
<213> ORGANISM: Homo sapiens

<400> SEQUENCE: 30

Met Val Ser Trp Met Ile Cys Arg Leu Val Val Leu Val Phe Gly Met

```
                1               5                   10                  15
Leu Cys Pro Ala Tyr Ala Ser Tyr Lys Ala Val Lys Thr Lys Asn Ile
                20                  25                  30

Arg Glu Tyr Val Arg Trp Met Met Tyr Trp Ile Val Phe Ala Leu Phe
                35                  40                  45

Met Ala Ala Glu Ile Val Thr Asp Ile Phe Ile Ser Trp Phe Pro Phe
                50                  55                  60

Tyr Tyr Glu Ile Lys Met Ala Phe Val Leu Trp Leu Leu Ser Pro Tyr
65                  70                  75                  80

Thr Lys Gly Ala Ser Leu Leu Tyr Arg Lys Phe Val His Pro Ser Leu
                85                  90                  95

Ser Arg His Glu Lys Glu Ile Asp Ala Tyr Ile Val Gln Ala Lys Glu
                100                 105                 110

Arg Ser Tyr Glu Thr Val Leu Ser Phe Gly Lys Arg Gly Leu Asn Ile
                115                 120                 125

Ala Ala Ser Ala Ala Val Gln Ala Ala Thr Lys Ser Gln Gly Ala Leu
                130                 135                 140

Ala Gly Arg Leu Arg Ser Phe Ser Met Gln Asp Leu Arg Ser Ile Ser
145                 150                 155                 160

Asp Ala Pro Ala Pro Ala Tyr His Asp Pro Leu Tyr Leu Glu Asp Gln
                165                 170                 175

Val Ser His Arg Arg Pro Ile Gly Tyr Arg Ala Gly Gly Leu Gln
                180                 185                 190

Asp Ser Asp Thr Glu Asp Glu Cys Trp Ser Asp Thr Glu Ala Val Pro
                195                 200                 205

Arg Ala Pro Ala Arg Pro Arg Glu Lys Pro Leu Ile Arg Ser Gln Ser
                210                 215                 220

Leu Arg Val Val Lys Arg Lys Pro Pro Val Arg Glu Gly Thr Ser Arg
225                 230                 235                 240

Ser Leu Lys Val Arg Thr Arg Lys Lys Thr Val Pro Ser Asp Val Asp
                245                 250                 255

Ser

<210> SEQ ID NO 31
<211> LENGTH: 189
<212> TYPE: PRT
<213> ORGANISM: Homo sapiens

<400> SEQUENCE: 31

Met Ser Ala Ala Met Arg Glu Arg Phe Asp Arg Phe Leu His Glu Lys
1               5                   10                  15

Asn Cys Met Thr Asp Leu Leu Ala Lys Leu Glu Ala Lys Thr Gly Val
                20                  25                  30

Asn Arg Ser Phe Ile Ala Leu Gly Val Ile Gly Leu Val Ala Leu Tyr
                35                  40                  45

Leu Val Phe Gly Tyr Gly Ala Ser Leu Leu Cys Asn Leu Ile Gly Phe
                50                  55                  60

Gly Tyr Pro Ala Tyr Ile Ser Ile Lys Ala Ile Glu Ser Pro Asn Lys
65                  70                  75                  80

Glu Asp Asp Thr Gln Trp Leu Thr Tyr Trp Val Val Tyr Gly Val Phe
                85                  90                  95

Ser Ile Ala Glu Phe Phe Ser Asp Ile Phe Leu Ser Trp Phe Pro Phe
                100                 105                 110

Tyr Tyr Met Leu Lys Cys Gly Phe Leu Leu Trp Cys Met Ala Pro Ser
```

115                 120                 125
Pro Ser Asn Gly Ala Glu Leu Leu Tyr Lys Arg Ile Ile Arg Pro Phe
            130                 135                 140

Phe Leu Lys His Glu Ser Gln Met Asp Ser Val Val Lys Asp Leu Lys
145                 150                 155                 160

Asp Lys Ala Lys Glu Thr Ala Asp Ala Ile Thr Lys Glu Ala Lys Lys
                165                 170                 175

Ala Thr Val Asn Leu Leu Gly Glu Glu Lys Lys Ser Thr
            180                 185

<210> SEQ ID NO 32
<211> LENGTH: 184
<212> TYPE: PRT
<213> ORGANISM: Homo sapiens

<400> SEQUENCE: 32

Met Asp Gly Leu Arg Gln Arg Val Glu His Phe Leu Glu Gln Arg Asn
1               5                   10                  15

Leu Val Thr Glu Val Leu Gly Ala Leu Glu Ala Lys Thr Gly Val Glu
            20                  25                  30

Lys Arg Tyr Leu Ala Ala Gly Ala Val Thr Leu Leu Ser Leu Tyr Leu
        35                  40                  45

Leu Phe Gly Tyr Gly Ala Ser Leu Leu Cys Asn Leu Ile Gly Phe Val
    50                  55                  60

Tyr Pro Ala Tyr Ala Ser Ile Lys Ala Ile Glu Ser Pro Ser Lys Asp
65                  70                  75                  80

Asp Asp Thr Val Trp Leu Thr Tyr Trp Val Val Tyr Ala Leu Phe Gly
                85                  90                  95

Leu Ala Glu Phe Phe Ser Asp Leu Leu Leu Ser Trp Phe Pro Phe Tyr
            100                 105                 110

Tyr Val Gly Lys Cys Ala Phe Leu Leu Phe Cys Met Ala Pro Arg Pro
        115                 120                 125

Trp Asn Gly Ala Leu Met Leu Tyr Gln Arg Val Val Arg Pro Leu Phe
    130                 135                 140

Leu Arg His His Gly Ala Val Asp Arg Ile Met Asn Asp Leu Ser Gly
145                 150                 155                 160

Arg Ala Leu Asp Ala Ala Ala Gly Ile Thr Arg Asn Val Lys Pro Ser
                165                 170                 175

Gln Thr Pro Gln Pro Lys Asp Lys
            180

<210> SEQ ID NO 33
<211> LENGTH: 263
<212> TYPE: PRT
<213> ORGANISM: Mus musculus

<400> SEQUENCE: 33

Met Arg Ile Phe Arg Pro Trp Arg Leu Arg Cys Pro Ala Leu His Leu
1               5                   10                  15

Pro Ser Phe Pro Thr Phe Ser Ile Lys Cys Ser Leu Pro Leu Pro
            20                  25                  30

Thr Asp Glu Asp Met Cys Lys Ser Val Thr Thr Gly Glu Trp Lys Lys
        35                  40                  45

Val Phe Tyr Glu Lys Met Glu Glu Val Lys Pro Ala Asp Ser Trp Asp
    50                  55                  60

Phe Ile Ile Asp Pro Asn Leu Lys His Asn Val Leu Ala Pro Gly Trp

-continued

```
                65                  70                  75                  80
Lys Gln Tyr Leu Glu Leu His Ala Ser Gly Arg Phe His Cys Ser Trp
                        85                  90                  95

Cys Trp His Thr Trp Gln Ser Pro His Val Val Ile Leu Phe His Met
            100                 105                 110

Tyr Leu Asp Lys Ala Gln Arg Ala Gly Ser Val Arg Met Arg Val Phe
                115                 120                 125

Lys Gln Leu Cys Tyr Glu Cys Gly Thr Ala Arg Leu Asp Glu Ser Ser
130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly His Tyr Arg Ile His
                165                 170                 175

Val Ala Ser Arg Gln Asp Asn Arg Arg His Arg Gly Glu Phe Cys Glu
                180                 185                 190

Ala Cys Gln Glu Gly Ile Val His Trp Lys Pro Ser Glu Lys Leu Leu
                195                 200                 205

Glu Glu Glu Ala Thr Thr Tyr Thr Phe Ser Arg Ala Pro Ser Pro Thr
210                 215                 220

Lys Pro Gln Ala Glu Thr Gly Ser Gly Cys Asn Phe Cys Ser Ile Pro
225                 230                 235                 240

Trp Cys Leu Phe Trp Ala Thr Val Leu Met Leu Ile Ile Tyr Leu Gln
                245                 250                 255

Phe Ser Phe Arg Thr Ser Val
            260
```

<210> SEQ ID NO 34
<211> LENGTH: 223
<212> TYPE: PRT
<213> ORGANISM: Mus musculus

<400> SEQUENCE: 34

```
Met Ser Thr Ser Leu Thr Thr Cys Glu Trp Lys Lys Val Phe Tyr Glu
1               5                   10                  15

Lys Met Glu Val Ala Lys Pro Ala Asp Ser Trp Glu Leu Ile Ile Asp
                20                  25                  30

Pro Thr Leu Lys Pro Asn Glu Leu Gly Pro Gly Trp Lys Gln Tyr Leu
            35                  40                  45

Glu Gln His Ala Ser Gly Arg Phe His Cys Ser Trp Cys Trp His Thr
        50                  55                  60

Trp Gln Ser Ala Asn Val Val Ile Leu Phe His Met His Leu Asp Arg
65                  70                  75                  80

Ala Gln Arg Val Gly Ser Val Arg Met Arg Val Phe Lys Gln Leu Cys
                85                  90                  95

Tyr Gln Cys Gly Thr Ser Arg Leu Asp Glu Ser Ser Met Leu Glu Glu
            100                 105                 110

Asn Ile Glu Gly Leu Val Asp Asn Leu Ile Thr Ser Leu Arg Glu Gln
        115                 120                 125

Cys Tyr Asp Glu Asp Gly Gly Gln Tyr Arg Ile His Val Ala Ser Arg
    130                 135                 140

Pro Asp Ser Gly Leu His Arg Ser Glu Phe Cys Glu Ala Cys Gln Glu
145                 150                 155                 160

Gly Ile Val His Trp Lys Pro Ser Glu Lys Leu Leu Glu Glu Asp Ala
                165                 170                 175
```

Ala Tyr Thr Asp Ala Ser Lys Lys Gly Gln Ala Gly Phe Ile Ser
            180                 185                 190

Ser Phe Phe Ser Phe Arg Trp Cys Leu Phe Trp Gly Thr Leu Cys Leu
            195                 200                 205

Val Ile Val Tyr Leu Gln Phe Phe Arg Gly Arg Ser Gly Phe Leu
    210                 215                 220

<210> SEQ ID NO 35
<211> LENGTH: 281
<212> TYPE: PRT
<213> ORGANISM: Mus musculus

<400> SEQUENCE: 35

Met Met Glu Glu Asp Ile Gly Asp Thr Glu Gln Trp Arg His Val Phe
1               5                   10                  15

Gln Glu Leu Met Gln Glu Val Lys Pro Trp His Lys Trp Thr Leu Ile
            20                  25                  30

Pro Asp Lys Asn Leu Leu Pro Asn Val Leu Lys Pro Gly Trp Thr Gln
        35                  40                  45

Tyr Gln Gln Lys Thr Phe Ala Arg Phe His Cys Pro Ser Cys Ser Arg
    50                  55                  60

Ser Trp Ala Ser Gly Arg Val Leu Ile Val Phe His Met Arg Trp Cys
65                  70                  75                  80

Glu Lys Lys Ala Lys Gly Trp Val Lys Met Arg Val Phe Ala Gln Arg
                85                  90                  95

Cys Asn Gln Cys Pro Glu Pro Pro Phe Ala Thr Pro Glu Val Thr Trp
            100                 105                 110

Asp Asn Ile Ser Arg Ile Leu Asn Asn Leu Leu Phe Gln Ile Leu Lys
        115                 120                 125

Lys Cys Tyr Lys Glu Gly Phe Lys Gln Met Gly Glu Ile Pro Leu Leu
130                 135                 140

Gly Asn Thr Ser Leu Glu Gly Pro His Asp Ser Ser Asn Cys Glu Ala
145                 150                 155                 160

Cys Leu Leu Gly Phe Cys Ala Gln Asn Asp Leu Gly Gln Ala Ser Lys
                165                 170                 175

Pro Pro Ala Pro Pro Leu Ser Pro Thr Ser Ser Lys Ser Ala Arg Glu
            180                 185                 190

Pro Lys Val Thr Val Thr Cys Ser Asn Ile Ser Ser Ser Arg Pro Ser
        195                 200                 205

Ser Lys Val Gln Met Pro Gln Ala Ser Lys Val Asn Pro Gln Ala Ser
    210                 215                 220

Asn Pro Thr Lys Asn Asp Pro Lys Val Ser Cys Thr Ser Lys Pro Pro
225                 230                 235                 240

Ala Pro Pro Leu Ser Pro Thr Ser Leu Lys Ser Ala Arg Glu Pro Lys
                245                 250                 255

Val Thr Val Thr Cys Ser Asn Ile Ser Ser Ser Arg Pro Ser Ser Lys
            260                 265                 270

Val Gln Met Pro Gln Ala Ser Lys Val
        275                 280

<210> SEQ ID NO 36
<211> LENGTH: 248
<212> TYPE: PRT
<213> ORGANISM: Mus musculus

<400> SEQUENCE: 36

Met Leu Phe Pro Asp Asp Phe Ser Thr Trp Glu Gln Thr Phe Gln Glu
1               5                   10                  15

Leu Met Gln Glu Glu Lys Pro Gly Ala Lys Trp Ser Leu His Leu Asp
            20                  25                  30

Lys Asn Ile Val Pro Asp Gly Ala Leu Gly Trp Arg Gln His Gln
        35                  40                  45

Gln Thr Val Gly Arg Phe Gln Cys Ser Arg Cys Cys Arg Ser Trp Thr
    50                  55                  60

Ser Ala Gln Val Met Ile Leu Cys His Met Tyr Pro Asp Thr Leu Lys
65                  70                  75                  80

Ser Gln Gly Gln Ala Arg Met Arg Ile Phe Gly Gln Lys Cys Gln Lys
                85                  90                  95

Cys Phe Gly Cys Gln Phe Glu Thr Pro Lys Phe Ser Thr Glu Ile Ile
                100                 105                 110

Lys Arg Ile Leu Asn Asn Leu Val Asn Tyr Ile Leu Gln Arg Tyr Tyr
            115                 120                 125

Gly His Arg Lys Ile Ala Leu Thr Ser Asn Ala Ser Leu Gly Glu Lys
        130                 135                 140

Val Thr Leu Asp Gly Pro His Asp Thr Arg Asn Cys Glu Ala Cys Ser
145                 150                 155                 160

Leu Asn Ser His Gly Arg Cys Ala Leu Ala His Lys Val Lys Pro Pro
                165                 170                 175

Arg Ser Pro Ser Pro Leu Pro Asn Ser Ser Pro Ser Lys Ser Cys
                180                 185                 190

Pro Pro Pro Pro Gln Thr Arg Asn Thr Asp Phe Gly Asn Lys Thr Leu
                195                 200                 205

Gln Asp Phe Gly Asn Arg Thr Phe Gln Gly Cys Arg Glu Pro Pro Gln
        210                 215                 220

Arg Glu Ile Glu Pro Pro Leu Phe Leu Phe Leu Ser Ile Ala Ala Phe
225                 230                 235                 240

Ala Leu Phe Ser Leu Phe Thr Arg
                245

<210> SEQ ID NO 37
<211> LENGTH: 263
<212> TYPE: PRT
<213> ORGANISM: Homo sapiens

<400> SEQUENCE: 37

Met Arg Ile Phe Arg Pro Trp Arg Leu Arg Cys Pro Ala Leu His Leu
1               5                   10                  15

Pro Ser Leu Ser Val Phe Ser Leu Arg Trp Lys Leu Pro Ser Leu Thr
            20                  25                  30

Thr Asp Glu Thr Met Cys Lys Ser Val Thr Thr Asp Glu Trp Lys Lys
        35                  40                  45

Val Phe Tyr Glu Lys Met Glu Glu Ala Lys Pro Ala Asp Ser Trp Asp
    50                  55                  60

Leu Ile Ile Asp Pro Asn Leu Lys His Asn Val Leu Ser Pro Gly Trp
65                  70                  75                  80

Lys Gln Tyr Leu Glu Leu His Ala Ser Gly Arg Phe His Cys Ser Trp
                85                  90                  95

Cys Trp His Thr Trp Gln Ser Pro Tyr Val Val Ile Leu Phe His Met
                100                 105                 110

Phe Leu Asp Arg Ala Gln Arg Ala Gly Ser Val Arg Met Arg Val Phe
            115                 120                 125

```
Lys Gln Leu Cys Tyr Glu Cys Gly Thr Ala Arg Leu Asp Glu Ser Ser
    130                 135                 140
Met Leu Glu Glu Asn Ile Glu Gly Leu Val Asp Asn Leu Ile Thr Ser
145                 150                 155                 160
Leu Arg Glu Gln Cys Tyr Gly Glu Arg Gly Gln Tyr Arg Ile His
                165                 170                 175
Val Ala Ser Arg Gln Asp Asn Arg Arg His Arg Gly Glu Phe Cys Glu
            180                 185                 190
Ala Cys Gln Glu Gly Ile Val His Trp Lys Pro Ser Glu Lys Leu Leu
        195                 200                 205
Glu Glu Glu Ala Thr Thr Tyr Thr Phe Ser Arg Ala Pro Ser Pro Thr
    210                 215                 220
Lys Ser Gln Asp Gln Thr Gly Ser Gly Trp Asn Phe Cys Ser Ile Pro
225                 230                 235                 240
Trp Cys Leu Phe Trp Ala Thr Val Leu Leu Ile Ile Tyr Leu Gln
                245                 250                 255
Phe Ser Phe Arg Ser Ser Val
                260
```

<210> SEQ ID NO 38
<211> LENGTH: 225
<212> TYPE: PRT
<213> ORGANISM: Homo sapiens

<400> SEQUENCE: 38

```
Met Cys Thr Ser Leu Thr Thr Cys Glu Trp Lys Lys Val Phe Tyr Glu
1               5                   10                  15
Lys Met Glu Val Ala Lys Pro Ala Asp Ser Trp Glu Leu Ile Ile Asp
                20                  25                  30
Pro Asn Leu Lys Pro Ser Glu Leu Ala Pro Gly Trp Lys Gln Tyr Leu
            35                  40                  45
Glu Gln His Ala Ser Gly Arg Phe His Cys Ser Trp Cys Trp His Thr
    50                  55                  60
Trp Gln Ser Ala His Val Val Ile Leu Phe His Met Phe Leu Asp Arg
65                  70                  75                  80
Ala Gln Arg Ala Gly Ser Val Arg Met Arg Val Phe Lys Gln Leu Cys
                85                  90                  95
Tyr Glu Cys Gly Thr Ala Arg Leu Asp Glu Ser Ser Met Leu Glu Glu
                100                 105                 110
Asn Ile Glu Gly Leu Val Asp Asn Leu Ile Thr Ser Leu Arg Glu Gln
            115                 120                 125
Cys Tyr Glu Glu Asp Gly Gly Gln Tyr Arg Ile His Val Ala Ser Arg
    130                 135                 140
Pro Asp Ser Gly Pro His Arg Ala Glu Phe Cys Glu Ala Cys Gln Glu
145                 150                 155                 160
Gly Ile Val His Trp Lys Pro Ser Glu Lys Leu Leu Glu Glu Glu Val
                165                 170                 175
Thr Thr Tyr Thr Ser Glu Ala Ser Lys Pro Arg Ala Gln Ala Gly Ser
                180                 185                 190
Gly Tyr Asn Phe Leu Ser Leu Arg Trp Cys Leu Phe Trp Ala Ser Leu
            195                 200                 205
Cys Leu Leu Val Val Tyr Leu Gln Phe Ser Phe Leu Ser Pro Ala Phe
    210                 215                 220
Phe
```

<210> SEQ ID NO 39
<211> LENGTH: 232
<212> TYPE: PRT
<213> ORGANISM: Homo sapiens

<400> SEQUENCE: 39

```
Met Ala Gly Asp Thr Glu Val Trp Lys Gln Met Phe Gln Glu Leu Met
1               5                   10                  15

Arg Glu Val Lys Pro Trp His Arg Trp Thr Leu Arg Pro Asp Lys Gly
            20                  25                  30

Leu Leu Pro Asn Val Leu Lys Pro Gly Trp Met Gln Tyr Gln Gln Trp
        35                  40                  45

Thr Phe Ala Arg Phe Gln Cys Ser Ser Cys Ser Arg Asn Trp Ala Ser
    50                  55                  60

Ala Gln Val Leu Val Leu Phe His Met Asn Trp Ser Glu Glu Lys Ser
65                  70                  75                  80

Arg Gly Gln Val Lys Met Arg Val Phe Thr Gln Arg Cys Lys Lys Cys
                85                  90                  95

Pro Gln Pro Leu Phe Glu Asp Pro Glu Phe Thr Gln Glu Asn Ile Ser
            100                 105                 110

Arg Ile Leu Lys Asn Leu Val Phe Arg Ile Leu Lys Lys Cys Tyr Arg
        115                 120                 125

Gly Arg Phe Gln Leu Ile Glu Glu Val Pro Met Ile Lys Asp Ile Ser
    130                 135                 140

Leu Glu Gly Pro His Asn Ser Asp Asn Cys Glu Ala Cys Leu Gln Gly
145                 150                 155                 160

Phe Cys Ala Gly Pro Ile Gln Val Thr Ser Leu Pro Pro Ser Gln Thr
                165                 170                 175

Pro Arg Val His Ser Ile Tyr Lys Val Glu Glu Val Lys Pro Trp
            180                 185                 190

Ala Ser Gly Glu Asn Val Tyr Ser Tyr Ala Cys Gln Asn His Ile Cys
        195                 200                 205

Arg Asn Leu Ser Ile Phe Cys Cys Val Ile Leu Ile Val Ile Val
    210                 215                 220

Val Ile Val Val Lys Thr Ala Ile
225                 230
```

<210> SEQ ID NO 40
<211> LENGTH: 246
<212> TYPE: PRT
<213> ORGANISM: Homo sapiens

<400> SEQUENCE: 40

```
Met Val Val Asp Phe Trp Thr Trp Glu Gln Thr Phe Gln Glu Leu Ile
1               5                   10                  15

Gln Glu Ala Lys Pro Arg Ala Thr Trp Thr Leu Lys Leu Asp Gly Asn
            20                  25                  30

Leu Gln Leu Asp Cys Leu Ala Gln Gly Trp Lys Gln Tyr Gln Gln Arg
        35                  40                  45

Ala Phe Gly Trp Phe Arg Cys Ser Ser Cys Gln Arg Ser Trp Ala Ser
    50                  55                  60

Ala Lys Leu Gln Ile Leu Cys His Thr Tyr Trp Glu His Trp Thr Ser
65                  70                  75                  80

Gln Gly Gln Val Arg Met Arg Leu Phe Gly Gln Arg Cys Gln Lys Cys
```

```
                        85                  90                  95
Ser Trp Ser Gln Tyr Glu Met Pro Glu Phe Ser Ser Asp Ser Thr Met
                    100                 105                 110

Arg Ile Leu Ser Asn Leu Val Gln His Ile Leu Lys Lys Tyr Tyr Gly
                115                 120                 125

Asn Gly Met Arg Lys Ser Pro Glu Met Pro Val Ile Leu Glu Val Ser
            130                 135                 140

Leu Glu Gly Ser His Asp Thr Ala Asn Cys Glu Ala Cys Thr Leu Gly
145                 150                 155                 160

Ile Cys Gly Gln Gly Leu Lys Ser Tyr Met Thr Lys Pro Ser Lys Ser
                165                 170                 175

Leu Leu Pro His Leu Lys Thr Gly Asn Ser Ser Pro Gly Ile Gly Ala
            180                 185                 190

Val Tyr Leu Ala Asn Gln Ala Lys Asn Gln Ser Asp Glu Ala Lys Glu
        195                 200                 205

Ala Lys Gly Ser Gly Tyr Glu Lys Leu Gly Pro Ser Arg Asp Pro Asp
    210                 215                 220

Pro Leu Asn Ile Cys Val Phe Ile Leu Leu Val Phe Ile Val Val
225                 230                 235                 240

Lys Cys Phe Thr Ser Glu
                245

<210> SEQ ID NO 41
<211> LENGTH: 210
<212> TYPE: PRT
<213> ORGANISM: Mus musculus

<400> SEQUENCE: 41

Met Glu Glu Val Lys Pro Ala Asp Ser Trp Asp Phe Ile Ile Asp Pro
1               5                   10                  15

Asn Leu Lys His Asn Val Leu Ala Pro Gly Trp Lys Gln Tyr Leu Glu
            20                  25                  30

Leu His Ala Ser Gly Arg Phe His Cys Ser Trp Cys Trp His Thr Trp
        35                  40                  45

Gln Ser Pro His Val Val Ile Leu Phe His Met Tyr Leu Asp Lys Ala
    50                  55                  60

Gln Arg Ala Gly Ser Val Arg Met Arg Val Phe Lys Gln Leu Cys Tyr
65                  70                  75                  80

Glu Cys Gly Thr Ala Arg Leu Asp Glu Ser Ser Met Leu Glu Glu Asn
                85                  90                  95

Ile Glu Ser Leu Val Asp Asn Leu Ile Thr Ser Leu Arg Glu Gln Cys
            100                 105                 110

Tyr Gly Glu Arg Gly Gly His Tyr Arg Ile His Val Ala Ser Arg Gln
        115                 120                 125

Asp Asn Arg Arg His Arg Gly Glu Phe Cys Glu Ala Cys Gln Glu Gly
    130                 135                 140

Ile Val His Trp Lys Pro Ser Glu Lys Leu Leu Glu Glu Glu Ala Thr
145                 150                 155                 160

Thr Tyr Thr Phe Ser Arg Ala Pro Ser Pro Thr Lys Pro Gln Ala Glu
                165                 170                 175

Thr Gly Ser Gly Cys Asn Phe Cys Ser Ile Pro Trp Cys Leu Phe Trp
            180                 185                 190

Ala Thr Val Leu Met Leu Ile Ile Tyr Leu Gln Phe Ser Phe Arg Thr
        195                 200                 205
```

```
Ser Val
    210

<210> SEQ ID NO 42
<211> LENGTH: 152
<212> TYPE: PRT
<213> ORGANISM: Mus musculus

<400> SEQUENCE: 42

Met Tyr Leu Asp Lys Ala Gln Arg Ala Gly Ser Val Arg Met Arg Val
1               5                   10                  15

Phe Lys Gln Leu Cys Tyr Glu Cys Gly Thr Ala Arg Leu Asp Glu Ser
            20                  25                  30

Ser Met Leu Glu Glu Asn Ile Glu Ser Leu Val Asp Asn Leu Ile Thr
        35                  40                  45

Ser Leu Arg Glu Gln Cys Tyr Gly Glu Arg Gly His Tyr Arg Ile
    50                  55                  60

His Val Ala Ser Arg Gln Asp Asn Arg Arg His Arg Gly Glu Phe Cys
65                  70                  75                  80

Glu Ala Cys Gln Glu Gly Ile Val His Trp Lys Pro Ser Glu Lys Leu
                85                  90                  95

Leu Glu Glu Glu Ala Thr Thr Tyr Thr Phe Ser Arg Ala Pro Ser Pro
            100                 105                 110

Thr Lys Pro Gln Ala Glu Thr Gly Ser Gly Cys Asn Phe Cys Ser Ile
        115                 120                 125

Pro Trp Cys Leu Phe Trp Ala Thr Val Leu Met Leu Ile Ile Tyr Leu
    130                 135                 140

Gln Phe Ser Phe Arg Thr Ser Val
145                 150

<210> SEQ ID NO 43
<211> LENGTH: 119
<212> TYPE: PRT
<213> ORGANISM: Mus musculus

<400> SEQUENCE: 43

Met Leu Glu Glu Asn Ile Glu Ser Leu Val Asp Asn Leu Ile Thr Ser
1               5                   10                  15

Leu Arg Glu Gln Cys Tyr Gly Glu Arg Gly His Tyr Arg Ile His
            20                  25                  30

Val Ala Ser Arg Gln Asp Asn Arg Arg His Arg Gly Glu Phe Cys Glu
            35                  40                  45

Ala Cys Gln Glu Gly Ile Val His Trp Lys Pro Ser Glu Lys Leu Leu
    50                  55                  60

Glu Glu Glu Ala Thr Thr Tyr Thr Phe Ser Arg Ala Pro Ser Pro Thr
65                  70                  75                  80

Lys Pro Gln Ala Glu Thr Gly Ser Gly Cys Asn Phe Cys Ser Ile Pro
                85                  90                  95

Trp Cys Leu Phe Trp Ala Thr Val Leu Met Leu Ile Ile Tyr Leu Gln
            100                 105                 110

Phe Ser Phe Arg Thr Ser Val
        115

<210> SEQ ID NO 44
<211> LENGTH: 234
<212> TYPE: PRT
<213> ORGANISM: Mus musculus
```

<400> SEQUENCE: 44

```
Met Arg Ile Phe Arg Pro Trp Arg Leu Arg Cys Pro Ala Leu His Leu
1               5                   10                  15

Pro Ser Phe Pro Thr Phe Ser Ile Lys Cys Ser Leu Pro Pro Leu Pro
            20                  25                  30

Thr Asp Glu Asp Met Cys Lys Ser Val Thr Thr Gly Glu Trp Lys Lys
        35                  40                  45

Val Phe Tyr Glu Lys Met Glu Glu Val Lys Pro Ala Asp Ser Trp Asp
    50                  55                  60

Phe Ile Ile Asp Pro Asn Leu Lys His Asn Val Leu Ala Pro Gly Trp
65                  70                  75                  80

Lys Gln Tyr Leu Glu Leu His Ala Ser Gly Arg Phe His Cys Ser Trp
                85                  90                  95

Cys Trp His Thr Trp Gln Ser Pro His Val Val Ile Leu Phe His Met
            100                 105                 110

Tyr Leu Asp Lys Ala Gln Arg Ala Gly Ser Val Arg Met Arg Val Phe
        115                 120                 125

Lys Gln Leu Cys Tyr Glu Cys Gly Thr Ala Arg Leu Asp Glu Ser Ser
    130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly His Tyr Arg Ile His
                165                 170                 175

Val Ala Ser Arg Gln Asp Asn Arg Arg His Arg Gly Glu Phe Cys Glu
            180                 185                 190

Ala Cys Gln Glu Gly Ile Val His Trp Lys Pro Ser Glu Lys Leu Leu
        195                 200                 205

Glu Glu Glu Ala Thr Thr Tyr Thr Phe Ser Arg Ala Pro Ser Pro Thr
    210                 215                 220

Lys Pro Gln Ala Glu Thr Gly Ser Gly Cys
225                 230
```

<210> SEQ ID NO 45
<211> LENGTH: 172
<212> TYPE: PRT
<213> ORGANISM: Mus musculus

<400> SEQUENCE: 45

```
Met Arg Ile Phe Arg Pro Trp Arg Leu Arg Cys Pro Ala Leu His Leu
1               5                   10                  15

Pro Ser Phe Pro Thr Phe Ser Ile Lys Cys Ser Leu Pro Pro Leu Pro
            20                  25                  30

Thr Asp Glu Asp Met Cys Lys Ser Val Thr Thr Gly Glu Trp Lys Lys
        35                  40                  45

Val Phe Tyr Glu Lys Met Glu Glu Val Lys Pro Ala Asp Ser Trp Asp
    50                  55                  60

Phe Ile Ile Asp Pro Asn Leu Lys His Asn Val Leu Ala Pro Gly Trp
65                  70                  75                  80

Lys Gln Tyr Leu Glu Leu His Ala Ser Gly Arg Phe His Cys Ser Trp
                85                  90                  95

Cys Trp His Thr Trp Gln Ser Pro His Val Val Ile Leu Phe His Met
            100                 105                 110

Tyr Leu Asp Lys Ala Gln Arg Ala Gly Ser Val Arg Met Arg Val Phe
        115                 120                 125
```

```
Lys Gln Leu Cys Tyr Glu Cys Gly Thr Ala Arg Leu Asp Glu Ser Ser
    130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly His
                165                 170
```

<210> SEQ ID NO 46
<211> LENGTH: 227
<212> TYPE: PRT
<213> ORGANISM: Mus musculus

<400> SEQUENCE: 46

```
Met Cys Lys Ser Val Thr Thr Gly Glu Trp Lys Lys Val Phe Tyr Glu
1               5                   10                  15

Lys Met Glu Glu Val Lys Pro Ala Asp Ser Trp Asp Phe Ile Ile Asp
                20                  25                  30

Pro Asn Leu Lys His Asn Val Leu Ala Pro Gly Trp Lys Gln Tyr Leu
            35                  40                  45

Glu Leu His Ala Ser Gly Arg Phe His Cys Ser Trp Cys Trp His Thr
    50                  55                  60

Trp Gln Ser Pro His Val Val Ile Leu Phe His Met Tyr Leu Asp Lys
65                  70                  75                  80

Ala Gln Arg Ala Gly Ser Val Arg Met Arg Val Phe Lys Gln Leu Cys
                85                  90                  95

Tyr Glu Cys Gly Thr Ala Arg Leu Asp Glu Ser Ser Met Leu Glu Glu
            100                 105                 110

Asn Ile Glu Ser Leu Val Asp Asn Leu Ile Thr Ser Leu Arg Glu Gln
        115                 120                 125

Cys Tyr Gly Glu Arg Gly Gly His Tyr Arg Ile His Val Ala Ser Arg
    130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Glu Ala
                165                 170                 175

Thr Thr Tyr Thr Phe Ser Arg Ala Pro Ser Pro Thr Lys Pro Gln Ala
            180                 185                 190

Glu Thr Gly Ser Gly Cys Asn Phe Cys Ser Ile Pro Trp Cys Leu Phe
        195                 200                 205

Trp Ala Thr Val Leu Met Leu Ile Ile Tyr Leu Gln Phe Ser Phe Arg
    210                 215                 220

Thr Ser Val
225
```

<210> SEQ ID NO 47
<211> LENGTH: 227
<212> TYPE: PRT
<213> ORGANISM: Homo sapiens

<400> SEQUENCE: 47

```
Met Cys Lys Ser Val Thr Thr Asp Glu Trp Lys Lys Val Phe Tyr Glu
1               5                   10                  15

Lys Met Glu Glu Ala Lys Pro Ala Asp Ser Trp Asp Leu Ile Ile Asp
                20                  25                  30

Pro Asn Leu Lys His Asn Val Leu Ser Pro Gly Trp Lys Gln Tyr Leu
            35                  40                  45
```

```
Glu Leu His Ala Ser Gly Arg Phe His Cys Ser Trp Cys Trp His Thr
 50                  55                  60

Trp Gln Ser Pro Tyr Val Val Ile Leu Phe His Met Phe Leu Asp Arg
 65                  70                  75                  80

Ala Gln Arg Ala Gly Ser Val Arg Met Arg Val Phe Lys Gln Leu Cys
                 85                  90                  95

Tyr Glu Cys Gly Thr Ala Arg Leu Asp Glu Ser Ser Met Leu Glu Glu
                100                 105                 110

Asn Ile Glu Gly Leu Val Asp Asn Leu Ile Thr Ser Leu Arg Glu Gln
            115                 120                 125

Cys Tyr Gly Glu Arg Gly Gln Tyr Arg Ile His Val Ala Ser Arg
            130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Ala
                165                 170                 175

Thr Thr Tyr Thr Phe Ser Arg Ala Pro Ser Pro Thr Lys Ser Gln Asp
                180                 185                 190

Gln Thr Gly Ser Gly Trp Asn Phe Cys Ser Ile Pro Trp Cys Leu Phe
            195                 200                 205

Trp Ala Thr Val Leu Leu Ile Ile Tyr Leu Gln Phe Ser Phe Arg
210                 215                 220

Ser Ser Val
225

<210> SEQ ID NO 48
<211> LENGTH: 212
<212> TYPE: PRT
<213> ORGANISM: Mus musculus

<400> SEQUENCE: 48

Met Arg Ile Phe Arg Pro Trp Arg Leu Arg Cys Pro Ala Leu His Leu
 1               5                  10                  15

Pro Ser Phe Pro Thr Phe Ser Ile Lys Cys Ser Leu Pro Pro Leu Pro
                 20                  25                  30

Thr Asp Glu Asp Met Cys Lys Ser Val Thr Thr Gly Glu Trp Lys Lys
             35                  40                  45

Val Phe Tyr Glu Lys Met Glu Glu Val Lys Pro Ala Asp Ser Trp Asp
 50                  55                  60

Phe Ile Ile Asp Pro Asn Leu Lys His Asn Val Leu Ala Pro Gly Trp
 65                  70                  75                  80

Lys Gln Tyr Leu Glu Leu His Ala Ser Gly Arg Phe His Cys Ser Trp
                 85                  90                  95

Cys Trp His Thr Trp Gln Ser Pro His Val Val Ile Leu Phe His Met
                100                 105                 110

Tyr Leu Asp Lys Ala Gln Arg Ala Gly Ser Val Arg Met Arg Val Phe
            115                 120                 125

Lys Gln Leu Cys Tyr Glu Cys Gly Thr Ala Arg Leu Asp Glu Ser Ser
130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly His Tyr Arg Ile His
                165                 170                 175

Val Ala Ser Arg Gln Asp Asn Arg Arg His Arg Gly Glu Phe Cys Glu
            180                 185                 190
```

Ala Cys Gln Glu Gly Ile Val His Trp Lys Pro Ser Glu Lys Leu Leu
            195                 200                 205

Glu Glu Glu Ala
    210

<210> SEQ ID NO 49
<211> LENGTH: 193
<212> TYPE: PRT
<213> ORGANISM: Mus musculus

<400> SEQUENCE: 49

Met Arg Ile Phe Arg Pro Trp Arg Leu Arg Cys Pro Ala Leu His Leu
1               5                   10                  15

Pro Ser Phe Pro Thr Phe Ser Ile Lys Cys Ser Leu Pro Pro Leu Pro
            20                  25                  30

Thr Asp Glu Asp Met Cys Lys Ser Val Thr Thr Gly Glu Trp Lys Lys
        35                  40                  45

Val Phe Tyr Glu Lys Met Glu Glu Val Lys Pro Ala Asp Ser Trp Asp
    50                  55                  60

Phe Ile Ile Asp Pro Asn Leu Lys His Asn Val Leu Ala Pro Gly Trp
65                  70                  75                  80

Lys Gln Tyr Leu Glu Leu His Ala Ser Gly Arg Phe His Cys Ser Trp
                85                  90                  95

Cys Trp His Thr Trp Gln Ser Pro His Val Val Ile Leu Phe His Met
            100                 105                 110

Tyr Leu Asp Lys Ala Gln Arg Ala Gly Ser Val Arg Met Arg Val Phe
        115                 120                 125

Lys Gln Leu Cys Tyr Glu Cys Gly Thr Ala Arg Leu Asp Glu Ser Ser
    130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly Gly His Tyr Arg Ile His
                165                 170                 175

Val Ala Ser Arg Gln Asp Asn Arg Arg His Arg Gly Glu Phe Cys Glu
            180                 185                 190

Ala

<210> SEQ ID NO 50
<211> LENGTH: 253
<212> TYPE: PRT
<213> ORGANISM: Mus musculus

<400> SEQUENCE: 50

Met Arg Ile Phe Arg Pro Trp Arg Leu Arg Cys Pro Ala Leu His Leu
1               5                   10                  15

Pro Ser Phe Pro Thr Phe Ser Ile Lys Cys Ser Leu Pro Pro Leu Pro
            20                  25                  30

Thr Asp Glu Asp Met Cys Lys Ser Val Thr Thr Gly Glu Trp Lys Lys
        35                  40                  45

Val Phe Tyr Glu Lys Met Glu Glu Val Lys Pro Ala Asp Ser Trp Asp
    50                  55                  60

Phe Ile Ile Asp Pro Asn Leu Lys His Asn Val Leu Ala Pro Gly Trp
65                  70                  75                  80

Lys Gln Tyr Leu Glu Leu His Ala Ser Gly Arg Phe His Cys Ser Trp
                85                  90                  95

```
-continued

Cys Trp His Thr Trp Gln Ser Pro His Val Val Ile Leu Phe His Met
            100                 105                 110

Tyr Leu Asp Lys Ala Gln Arg Ala Gly Ser Val Arg Met Arg Val Phe
            115                 120                 125

Lys Gln Leu Cys Tyr Glu Cys Gly Thr Ala Arg Leu Asp Glu Ser Ser
    130                 135                 140

Met Leu Glu Glu Asn Ile Glu Ser Leu Val Asp Asn Leu Ile Thr Ser
145                 150                 155                 160

Leu Arg Glu Gln Cys Tyr Gly Glu Arg Gly Gly His Tyr Arg Ile His
                165                 170                 175

Val Ala Ser Arg Gln Asp Asn Arg Arg His Arg Gly Glu Phe Cys Glu
            180                 185                 190

Ala Cys Gln Glu Gly Ile Val His Trp Lys Pro Ser Glu Lys Leu Leu
            195                 200                 205

Glu Glu Glu Ala Thr Thr Tyr Thr Phe Ser Arg Ala Pro Ser Pro Thr
    210                 215                 220

Lys Pro Gln Ala Glu Thr Gly Ser Gly Cys Asn Phe Cys Ser Ile Pro
225                 230                 235                 240

Trp Cys Leu Phe Trp Ala Thr Val Leu Met Leu Ile Ile
                245                 250

<210> SEQ ID NO 51
<211> LENGTH: 48
<212> TYPE: DNA
<213> ORGANISM: Artificial
<220> FEATURE:
<223> OTHER INFORMATION: Synthetic

<400> SEQUENCE: 51
tatagaattc gcggccgctc gcgattttt ttttttttt ttttttt                    48
```